United States Patent
Rodriguez

(10) Patent No.: US 6,288,303 B1
(45) Date of Patent: Sep. 11, 2001

(54) RICE β-GLUCANASE ENZYMES AND GENES

(75) Inventor: Raymond L. Rodriguez, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/105,390

(22) Filed: Jun. 25, 1998

Related U.S. Application Data

(60) Provisional application No. 60/050,675, filed on Jun. 25, 1997.

(51) Int. Cl.$^7$ .......................... C12N 15/29; C12N 15/56; C12N 15/82; A01H 5/00; A01H 5/10

(52) U.S. Cl. .................. 800/287; 435/69.8; 435/320.1; 435/468; 536/23.6; 536/24.1; 800/298; 800/320; 800/320.2

(58) Field of Search .............................. 435/69.1, 320.1, 435/410, 419, 468, 69.8; 536/23.6, 24.1; 800/278, 287, 288, 295, 298, 320, 320.2

(56) References Cited

FOREIGN PATENT DOCUMENTS

WO 95/14099   5/1995 (WO) .............................. C12N/15/82

OTHER PUBLICATIONS

Akiyama, T., et al., "Purification and Properties of a Basic Endo–1,3–β–Glucanase from Rice (*Oryza sativa* L.)," Plant Cell Physiol. 37(5):702–705 (1996b).
Akiyama, T., et al., "Purification and Partial Characterization of an Endo–(1→3,1→4)–β–glucanase from Rice, *Oryza sativa* L.," Biotech. Biochem. 60:2078–2080 1996a).
Akiyama, T., et al., "Purification and characterization of a (1→3)–B–D–glucan endohydrolase from rice (*Oryza sativa*) bran," Carbohydr. Res. 297: 365–374 (1997).
Benhamou, N.,: Elicitor–induced plant defense pathways, Trends in Plant Science 1(7):233–240 (1996).
Chen, Z., et al., "Induction, modification and transduction of the salicylic acid signal in plant defense responses," Proc. Natl. Acad. Sci. USA 92:4134–4137 (1995).
Fincher, G.B., et al., "Primary structure of the (1→3,1→4)–β–D–glucan 4–glucohydrolase from barley aleurone," Proc. Natl. Acad. Sci. USA 83:2081–2085 (1986).
Høj, P.B., et al., "Purification of (1→3)–β–glucan endohydrolase isoenzyme II from germinated barley and determination of its primary structure from cDNA clone," Plant Mol. Biol. 13:31–42 (1989).
Huang, N., et al., "Structural organization and differential expression of rice α–amylase genes," Nuc. Acids Res. 18:7007–7014 (1990).
Linthorst, H., "Pathogenesis–Related Proteins of Plants," Crit Rev. Plant Sci. 10(2):123–150 (1991).

Litts, J.C., et al., "The isolation and characterization of a barley 1,3–1,4–β–glucanase gene," Eur. J. Biochem. 194:831–838 (1990).
Malehorm, D.E., et al, "Structure and expression of a barley acidic β–glucanase gene," Plant Mol. Biol. 22:347–360 (1993).
Masoud, S.A. et al., "Constitutive expression of an inducible β–1,3–glucanase in alfalfa reduces disease severity caused by the oomycete pathogen *Phytophthora megasperma* f.sp *medicaginis*, but does not reduce disease severity of chitin–containing fungi," Transgenic Res. 5:313–323 (1996).
Mueller, M.J., et al., "Signaling in the elicitation process is mediated through the octadecanoid pathway leading to jasmonic acid," Proc. Natl. Acad. Sci USA 90:7490–7494 (1993).
Sela–Buurlage, M.B., et al., "Only Specific Tobacco (*Nicotiana tabacum*) Chitinases and β–1,3–Glucanases Exhibit Antifungal Activity," Plant Physiol. 101:857–863 (1993).
Simmons, C.R., "The Physiology and Molecular Biology of Plant 1,3–β–D–Glucanases and 1,3;1,4–β–D–Glucanases," Crit. Rev. Pant Sci. 13(4);326–387 (1994).
Simmons, C.R., et al., "Structure of a rice β–glucanase gene regulated by ethylene, cytokinin, wounding, salicylic acid and fungal elicitors," Plant Mol. Biol. 18:33–45 (1992).
Slakeski, N., et al., "Structure and tissue–specific regulation of genes encoding barley (1→3, 1→4)–β–glucan endohydrolases," Mol. Gen. Genet. 224:437–449 (1990).
Varghese, J.N., et al., "Three–dimensional structures of two plant β–glucan endohydrolases with distinct substrate specificities," Proc. Natl. Acad. Sci. USA 91:2785–2789 (1994).
Wang, J., et al., "Purification characterization and gene structure of (1→3)–β–glucanase isoenzyme GIII from barley (*Hordeum vulgare*)." Eur. J. Biochem 209:103–109 (1992).
Wolf, N., "Complete Nucleotide Sequence of a *Hordeum vulgare* Gene Encoding (1→3,1→4β–Glucanase Isoenzyme II," Plant Physiol. 96:1382–1384 (1991).
Wu, S., et al., "Nucleotide Sequence of a Maise cDNA for a Class II, Acidic β–1,3–Glucanase," Plant Physiol. 106:1709–1710 (1994).
Xu, P., et al., "Evolution and differential expression of the (1→3)–β–glucan encohydrolase–encoding gene family in barley, *Hordeum vulgare*," Gene 120: 157–165 (1992).

(List continued on next page.)

*Primary Examiner*—Gary Benzion
*Assistant Examiner*—Ashwin D. Mehta
(74) *Attorney, Agent, or Firm*—Townsend and Townsend and Crew LLP

(57) ABSTRACT

A group of novel rice β-glucanase genes, identified as β-glucanases 2–9 (Gns 2–9), and the corresponding β-glucanase enzymes, are disclosed. The genes, and the gene promoters, are useful in a variety of transgenic monocot plants, for achieving increased plant resistance to fungal infection, improved growth characteristics, and high levels of expression of heterologous protein in various tissues obtained from the plants.

16 Claims, 2 Drawing Sheets

OTHER PUBLICATIONS

Yoshikawa, M., et al., "Resistance to Fungal Diseases in Transgenic Tobacco Plants Expressing the Phytoalxin Elicitor–Releasing Factor, β–1,3–Endoglucanase, from Soybean," Naturwissenschften 80:417–420 (1993).

Yun, S., et al., "Sequence of a (1–3,1–4)–β–Glucanase cDNA from Oat," Plant Physiol. 103:295–296 (1993).

Zhu, Q., et al., "Enhanced Protection Against Fungal Attack by Constitutive Co–expression of Chitinase and Glucanase Genes in Transgenic Tobacco," Bio/Technology 12:807–812 (1994).

Cornelissen et al., "Strategies For Control of Fungal Diseases with Transgenic Plants," Plant Physiol. 101:709–712 (1993).

Woloshuk et al., "Pathogen–Induced Proteins with Inhibitory Activity Toward Phytophthora Infestans," Plant Cell 3:619–628 (1991).

SEQUENCE LISTING (1) GENERAL INFORMATION:

(iii) NUMBER OF SEQUENCES: 66

(2) INFORMATION FOR SEQ ID NO:1:

(i) SEQUENCE CHARACTERISTICS:
       (A) LENGTH: 2230 base pairs
       (B) TYPE: nucleic acid
       (C) STRANDEDNESS: single
       (D) TOPOLOGY: linear (xi) SEQUENCE DESCRIPTION: SEQ ID NO:1:

```
ACTGTTATGA CATGAGGTAT GGATGACTGC CCCTATGAGC TTTGTTTGTT CAGTAAGATC      60

ACAGCTGTTG TATCATATAT TTATAGGATA TTTTTCTGCA ATGCAATTTG TTTTCCTCAG     120

CCTGTTGTAA TTTGACAAAT TTAAGCACA  TCGAGGGCCA TTCCCTCAAA CAACGATACT     180

TCAGTACAAC ATCGAGGGTC ATTCCCTCAA CTTTAAACTT TCATGAGCCT CACTGTACTG     240

AGTACTCTAT GCCGTGATGT GCCGGGTAGT CTTGGAGTTC CAAATTAGCG TGTGTACGTG     300

TGTGGTCAAG AAGGATTCAG AGGTTGGCAT TGGTAGATTT TTTTTTTGAA CAAAGCATTG     360

GAAGATTTTA GCCAGAACCG TCCAACAAGT AGCGGCTTAT TTTGACTTGA GCTCTTAAGT     420

CTGCAGAGGT GTATCTACTC TGCACTCACC CGTGTGCGAC GGGGTTGGCT AACCCAGGAG     480

GAAAGGAAAA AAAACACACG GAGCTTGTTT ATGTGGTGAC GAATGAACAG TAAATGAACG     540

TATGTCAATC CCATTTGTAT TGATCTTGTC CAGTCTTCGC CTGGAAATTC CGAGCAGCGT     600

GACTATAAAA GCAAGCTTGC AGCGTTGCAT TTTCTTACAT CCAGATCGAG TTCAAGTGCA     660

ACAGATCAAA CTAGTAGCAG CAGAAGATGT CTATGCAAGG CGTTGTTCCT GTGCTTGCAG     720

CGGCTTTGGC CATTGCAGCC TTCGCCTCCT TTCCTTCAGG TACACATATT GCTAAGCTTC     780

GTTATATGTA GGTCGTAAGT ACTAAGTTTT TTTTTAAAGA AATGTAAAT  GTATTCCTGC     840

TTGTGTTTTA TAAAGTTATA GCTTCCCTTA AAAAAGAAGT TATAGCCACT TATTATATAA     900

CTGGCTTAAA AGAGAGCTCA TAAAACCTAA GACATGAAGA TGAAAACTA  ATAATAGCAA     960

CACTAAAGAA GAAACTTTTA TTCAAGTCTA TTTGTAAATC TCCAACTGTA GTTAACAAAA    1020

TTATTCATAG CCGTTGACTC TAGATTTTGG CGTGCAGTAT GCATTAGCTC GTTTTTCTCG    1080

TCACACCTTT GTAAATCGTA AGTACTTGTC CTAAAATTAG TGGACATCAG TATGATAATG    1140

TCAAATTTAC GATTTAATTT GGATCTGGAT GAATTGAGTG CTTACCCGAA AAACTAGTCA    1200

TCTGGCCACA TATGTCAAGC CTACCGTGCG ATACTGTGCT CGTTGTCACT GAACCCGTAC    1260

GCTTGTGCGT GCGTATGCTG AGATTTGGTG CAGCATGCGA TCCATCGGCG TGTGCTACGG    1320

CATGAACGGC GACGGCCTCC CGTCGCGGAG CAACGTCGTG CAGCTCTACA AGTCCAACGG    1380

CATCGGCGCC ATGCGCATCT ACTCCGCCGA CCGCGAGGCC CTCGACGCCC TGCGCGGCTC    1440

GGGCATCGAC CTCGCCCTCG ACGTCGGCGA ACGGAACGAC GTCGGCCAGC TCGCGGCCAA    1500

CGCGGACTCC TGGGTCCAGG ACAACGTGAA GGCTTACTAC CCGGACGTCA AGATCAAGTA    1560

CATCGTCGTC GGCAACGAGC TCACCGGCAC CGCGACGGCG AGCATCCTCC CGGCCATGCA    1620

GAACGTCCAG GCCGCCCTCG CGTCCGCAGG CCTCGCGAAG ATCAAGGTGA CCACCGCCAT    1680

CAAGATGGAC ACGCTCGCCG CCTCATCGCC GCCGTCCGCC GTGTTCACCA ACCCATCCGT    1740

CATGGAGCCC ATCGTGAGGT TCCTCACCGG CAACGCGGCG CCGCTCCTGG CCAACGTGTA    1800

CCCCTACTTC GCGTACAGGG ACAGCCAGGA CATCGACCTC AGCTACGCGC TCTTCCAGCC    1860
```

```
GAGCTCGACC ACGGTGAGCG ACCCCAACGG CGGCGGGCTG AGCTACACGA ACCTCTTCGA    1920

CGCCATGGTC GACGCCGTCC GCGCCGCCGT GGAGAAGGTG AGCGGCGGCG GAAGCAGCGT    1980

CGTCGACGTC GTGGTGTCGG AGAGCGGGTG GCCGTCGGAC GGCGGGAAGG GGGCCACCGT    2040

GGAGAACGCG CGGGCGTACA ACCAGAATCT GATCGACCAC GTCGCCCAAG GCACGCCGAA    2100

GAAGCCCGGG CAGATGGAGG TGTACGTGTT CGCCTTGTTC AACGAGAACC GGAAGGAAGG    2160

CGACGCCACG GAGAAGAAGT TTGGGCTGTT CAATCCAGAC AAGACACCGG TTTACCCAAT    2220

CACTTTCTAG                                                          2230

(2) INFORMATION FOR SEQ ID NO:2:

(i) SEQUENCE CHARACTERISTICS:
        (A) LENGTH: 1949 base pairs
        (B) TYPE: nucleic acid
        (C) STRANDEDNESS: single
        (D) TOPOLOGY: linear (xi) SEQUENCE DESCRIPTION: SEQ ID NO:2:

CAACGTTGTC GGAATACTAG ATTAGGGTTT TCACCCCCAA AGAACATCAC CACAATCTGT      60

TGTTCACCCC CAAAGAACAT CACCACAATC TGTTGTTCGA ACGTCGATCC AATTTTCCGA     120

CCAAAATGAG GATGACCCAC AAACTCTATT TCAAAGTGGC AACTTTCCTG GAGCCACATA     180

TAACAAGATT AGTTCGCCAG CCACCACATA AGCAAGGAGA TAAAGGAAAA AATGAAAATA     240

AAATAATTAC ACCAGTCAAA TAAAGCAATA GAGGATTTGC TAATCAAATT CATCATGAAC     300

ATTGGTTGGA TTCCTTGAGA GGTCAGATTC ATCATCCCGT ATTTATGTCT TGACATTTGG     360

AATTTTGATT TTCTGGCACT ATGGTTTGCA GCTTATCGGG AACCTATTCA GTCTCATCTG     420

CATGCTGAGT GTTTATAGTT TATCCGGAAC AATTCACACA TTCATCTGCT TGCTGAGTAC     480

CAGTATAAAT CAAGCTGCTC TGCTTTGAAC TCTGTAAATT ACATCCAGAA ACCAAGTGAA     540

CTATAGGTGG TCTAGGTACA GAATACGCCA CATTTGTTAC ATCTCTCTAG GTTTGAGACC     600

ACAAGAGATG GTGAATATAC GAGGTTTCTC CCTGGTTTTT GCAGCTGCAT TGCTGCTTCT     660

TGGAGTTTTT ATCTCAATCC CTGTAGGTAC GTGATTCGCC TGTACTATTG AATATTGATA     720

TATGTATTGT TGATATTAAT CTATCTGATT GAATTTTTTA AATTTTTTAT AACTATTTAG     780

ATGACATGTA GACAATGAGG GTATGTCTCG TCAAAAGTTT AAAATAGTTT CCCATTGTTT     840

GAAACATAAG AATTTTGAAA AAAAAATTAT AAGGACTGAA CTATTTCCGA CGAAATTTCT     900

GCAAAAACTT TGTACTTGTC CAAAGAGATC TTAGGTCCAT TTGGGTAGGT AGAAACAAAT     960

TAAAGATCAG AGCTTGTACT GATGCTTTTC TGTCTGAATG AAATACATGT GGTGCAGGCG    1020

TGCAATCCGT TGGTGTGTGC TACGGCATGA TCGGCAACGA TCTCCCGTCG AAGAGCGACG    1080

TCGTGCAGCT CTACAAATCC AATGGCATCA CAGACATGCG CATCTACTTG CCCGACGTCG    1140

AGGCCATGAA CGCCCTGCGC GGCACAGGCA TCGGCCTCAT CGTCGGCGTC GCCAACGACA    1200

TCCTCATCGA CCTCGCCGCC AACCCGGCGT CCGCCGCGTC CTGGGTCGAC GCGAACGTCA    1260

AGCCGTTCGT CCCGGCGGTG AACATCAAGT ACATCGCAGT CGGCAACGAG ATCTCCGGCG    1320

AGCCCACGCA GAACATCCTC CCGGTCATGC AGAACATCAA CGCCGCCCTG GCCGCGGCGA    1380

GCATCACCGG CGTCAAGGCG TCCACGGCGG TGAAGCTAGA CGTCGTCACC AACACGTTCC    1440

CGCCCTCGGC CGGCGTGTTC GCGGCGCCCT ACATGACGGC CGTGGCCAAG CTCCTGCGAT    1500

GCACCGGCGC GCCGCTGCTC GCCAACATCT ACCCCTACTT CGCCTACATC GGCAACAAGA    1560

AGGACATCAG CCTCAACTAC GCCACGTTCC AGGCCGGCAC GACGGTGCCC GACCCCAACA    1620
```

```
CCGACCTGGT GTACGCCAAC CTGTTCGACG CCATGGTCGA CTCCGTCTAC GCCGCGCTGG    1680

ACAAGGCCGG CGCGGCGGGC GTCAGCATCG TCGTGTCGGA GAGCGGGTGG CCGTCGGCCG    1740

GCGGGGACTC GGCCACGATC GACATCGCGC GGACCTACGT GCAGAACCTG ATTAAGCATG    1800

CGAAGAAGGG GACGCCGAAG CCGGGGGTGA TCGAGACGTA CGTGTTCGCC ATGTTCAACG    1860

AGAACCAGAA GCCCGGGGAA GCCACGGAGC AAAACTTTGG AGCCTTCTAC CCTAACAAGA    1920

CAGCAGTCTA CCCTATCAAT TTCCAGTGA                                     1949
```

(2) INFORMATION FOR SEQ ID NO:3:

(i) SEQUENCE CHARACTERISTICS:
        (A) LENGTH: 2317 base pairs
        (B) TYPE: nucleic acid
        (C) STRANDEDNESS: single
        (D) TOPOLOGY: linear (xi) SEQUENCE DESCRIPTION: SEQ ID NO:3:

```
GAATTCCATG AAGCGGAAGA ATACATGCTG TGTCTAAGTA CGCCAAGAAA ACAGAGGCGA      60

GTTTCCACGT TTCATGGAAT TTTTTAGCTC CAACAAGCCG CTGTTTCTGT GGAAAAAATG    120

GGAGGAAGAT GGCTAGTTAG GCTGCAAATG CAACGTAGCA GCTAGCTGTA AGCACGCACT    180

TGGGCCGTGG ATGTGAGGAA ATTAATGTGC CTAACTGGCT AGACACTGAA ACTTGTATAT    240

AAAGGGGTGT GCATTGGCAC ATAGCATGCA TAACATTCAG GTTCAGGAGC AGCAGTTGGG    300

AGTAGCTAGC TGGGACAACA ATGGCCAGGA GACAGGGAGT TGCTTCTATG CTTACAATTG    360

CTCTGATCAT TGGAGCATTT GCTTCTGCTC CAACAAGTAC TGATCAGATT CTCTCTATGT    420

TTCTAGCAAA TAGCAATTCT CTGTTTTGCT TGCAATGCCC TGAGCACGTA CTGTAAGTGT    480

TTAGTGGCTA GTCAGAGATT TGAGGGGAAC AAAATTCTGA AGAGCACCAC AATGTTCTTT    540

ATAGAATAAA CCACATTTTA TCTATATGCA TCTTGTTGTC TTTTCATAAC TATGGAATTT    600

CCCCACGTAA TTTTACACGG GTCAGTTGAA TTGAATTTGA TATAGAACTC TTAGTTCCTA    660

TTTCCATATA TGCAATATTT TCTACACAAT ACATTACAAT TGCAATAGTA CTTTGTATAC    720

AAATATTGCT ATATACTCCC TCCGTTTCAA AATGTTTGAC ACCCTTGACT TTTTAGAACA    780

TGTTTGACCG TTTGTCTTAT TCAAAAAAAA TTGTGAAATA TGTAAAATTA TATGTGTACA    840

TGAAAGTTTA TTTAACAATG AATCAAATGA TATGAAAAGA ATAAATAATT ACTTAAATTT    900

TTTGAATAAG ACAAATGGTT CCAAACACGT ACTAAAAAGT TCCACGGTGT TCCAAACTTT    960

TGAAACGGAA GGAGTATTAA TCTACACCGT TAATTTGGTC CTAGATGATG TAATTAGCTT   1020

AGATCTTATT ATTTTATTAA TATGATAATG TATAGGTATA CATAGCGAAT ATGGTGACTT   1080

CGTTTCAAGT TATCATTATG TTACTATACA ATATATATAT AATAGATCAT GTCTGGTCTA   1140

GATAATATAA TAGATAATAT ATAGATAGAT ATATGGAAGA TAGATAAATA GATAGATGAA   1200

ACTAAATAAA ATGTCCGGAC CAGATAGACA CTATAGCTTT GGGTTAATTC TTTTTGGGCA   1260

AACAAAGTTT CACTTGAAAT TCAACTAGGC ATGCTCTGTA ATTCGAAGGT GCACGTTCAT   1320

GTGTACTCTG CTATGGTTTA TTGAAAACCT AACTTTATGC TGTCGGTGTC CATTATCCTG   1380

TCGTGCATAT GCAGCTGTGC AATCCATCGG CGTGTGCTAT GGCGTTCTCG GCAACAACCT   1440

CCCGTCGCGG AGCGAGGTGG TGCAGCTGTA CAAGTCCAAG GGCATCAACG GCATGCGCAT   1500

CTACTACCCC GACAAGGAGG CGCTCAACGC CCTGCGCAAC TCCGGTATCG CCCTCATCCT   1560

CGACGTCGGC GACCAGTTGT CCAACCTCGC CGCCAGCTCC TCCAAGCCGG CCGCGTGGGT   1620

CCGCGACAAC GTCAGGCCCT ACTACCCGGC CGTCAACATC AAGTACATCG CCGTCGGCAA   1680
```

| | |
|---|---|
| CGAGGTGGAA GGCGGCGCCA CGAGTAGCAT CCTCCCGGCC ATCCGCAACG TCAACTCCGC | 1740 |
| CCTGGGCTCG GTCGGCCTCG GGCGCATCAA GGCGTCCACC GCGGTGAAGT TCGACGTCAT | 1800 |
| CTCCAACTCC TACCCACCCT CCGCCGCGGT CTTCAGGGAC GCCTACATGA AGGACATCGC | 1860 |
| GCGCTACCGA TGCACCGGCG CGCCGCTGCT CGCCAACGTG TACCCGTACT TCGCCTACAG | 1920 |
| GGGGAACCCG CGCGACATCA GCCTCAACTA CGCCACGTTC CGGCCGGGCA CCACGGTGAG | 1980 |
| GGACCCAAAC AACGGGCTCA CCTACACCAA CCTGTTCGAC GCCATGATGG ACGCCGTGTA | 2040 |
| CGCCGCGCTG GAGAAGGCCG GCGCCGGGAA CGTGAGGGTG GTGGTGTCGG AGAGCGGGTG | 2100 |
| GCCGTCGGCG GGAGGGTTCG GGGCGAGCGT GGACAATGCG AGGGCGTACA ACCAGGGGCT | 2160 |
| GATCGACCAT GTGCGTGGCA CGCCCAAGAG GCGCGGGGCA CTGGAGGCGT ACATATTCGC | 2220 |
| CATGTTCAAT GAGAACCAGA GAACGGGGA TCCCACCGAG AGAAACTTTG GGCTCTTCTA | 2280 |
| CCCTAACAAG TCGCCCGTGT ATCCCATCCG GTTCTGA | 2317 |

(2) INFORMATION FOR SEQ ID NO:4:

(i) SEQUENCE CHARACTERISTICS:
        (A) LENGTH: 1834 base pairs
        (B) TYPE: nucleic acid
        (C) STRANDEDNESS: single
        (D) TOPOLOGY: linear (xi) SEQUENCE DESCRIPTION: SEQ ID NO:4:

| | |
|---|---|
| GAATTCCACG AACGCGGCCC CGGTCGACAG CTAACGAGCT TTTGTTTTTA CGGCCGCGAT | 60 |
| TGGTGGACGA CGACCTCGTT TCGCTGCAGT CTTGCGCGCG CGTGTACGCA TTTTCTATAG | 120 |
| CGAGATACCA CTACTATCTT GTAGAATTAG GCCGGTGCGG ATCGCGACCA CGCTTGTCTC | 180 |
| TACGCTCGAT ATCGTATACT AGCACGTAGC GGGTGGAAAC GGGCGCCAAC AATTGCATGG | 240 |
| TACATGCATG CCTGCCAGGA ACTTGTATAA ATAGGGGGTG AATGCTTTTG TTACATCGCA | 300 |
| TCGATCTGCA TGCGAAGTCC TGCAGCCTCC GTAGCAGACA CGTACAACGT ACCGAGCAAC | 360 |
| CTTAGCTAGT GGCGCCTGAA AATTATTAAG CGCTTCAAGA TGGCAAAGCA TGGCGTTGCT | 420 |
| TCCGTTTTAA CACTGGCATT GGTCCTTGGA GTTGCGGCCA TTCCTACAGG TAATAATTGT | 480 |
| ATATTGTCTT AATAAAATTC GGTTTGTCTA AAACTCTTAA TAAGGGATGT CCTCTCGTTT | 540 |
| GTTTAAAACC CATTCAAATA GTTATGGAAA TTTCTGAAAC AAATTGACCA CATTCATAGA | 600 |
| AAATATGTAT ATACTAATTC ACTAAATTTT AGATCCTAAC ACAACTCATC ACACATTATG | 660 |
| GTATAAAAAA AGATAAATAC GAACGAAATT TATCTTCTTT TTTTTCTTAA TGTGGATGGT | 720 |
| GAAATTTGAA CTTGATTTTT GGTGTAGTGG TACATGTTAC TGTACTCTAT ATTATTAATT | 780 |
| TGATTAAATT TTTTCTTAAC TATTTGTGTT GAATTTGGAA AAAAAAGTTA TAAGATGGAA | 840 |
| TATCCTCTAA AGGGATTAAT AATCCACTCC CAAACAAAAA GGAGTCTAAT ATATCAAATC | 900 |
| AAACACAGTG GTGCAATCTA TCGGCGTGTG CTACGGCGTG ATCGGGAACA ACCTGCCGTC | 960 |
| GCCGAGCGAC GTCGTGCAGC TCTACAAGTC CAACGGCATC GACTCCATGC GCATCTACTT | 1020 |
| CCCAAGAAGC GACATCCTCC AGGCCCTCAG CGGCTCAAGC ATCGCCCTCA CCATGGACGT | 1080 |
| CGGCAACGAT CAGCTCGGCT CCCTCGCCTC CGACCCCTCC GCCGCCGCCG CCTTCGTCCA | 1140 |
| GAACAACATC CAGGCGTTCC CGGGCGTCAA CTTCCGCTAC ATCACCGTCG GCAACGAGGT | 1200 |
| TTCCGGCGGC GACACGCAGA ACATCCTCCC GGCCATGCAG AACATGAACA GGGGCCTCTC | 1260 |
| CGCCGCCGGG CTCGGGAACA TCAAGGTGTC GACGTCGGTG TCCCAGGCGG AGGTTGGCAA | 1320 |
| CGGCTTCCCG CCGTCCGCCG GGACGTTCTC CGCCTCGGAC ATGGGGCCCA TAGGTCAGTA | 1380 |

```
CCTGGGGAGC ACCGGGGGGC CGCTGCTCGC CAACGTCTAC CCCTACTTCG CCTACGTGGC    1440

AACCAGGGCC CAGATCGACA TCAACTACGC GCTCTTCACG TCGCCGGGCA CGGTGGTGCA    1500

GGACGGCGGC AACGCGTACC AGAACCTGTT CGACGCCATC GTCGACACGT TCTACTCCGC    1560

GCTGGAGAGC GCCGGCGCCG GGAGCGTCCC GATCGTGGTG TCGGAGAGCG GGTGGCCGTC    1620

GGCGGGCGGC ACGGCCGCGA GCGCCGGCAA CGCGCAGACG TACAACCAGA ACCTGATCAA    1680

CCACGTCGGG CAGGGGACGC CCAAGAGGCC CGGGAGCATC GAGACCTACA TTTTCGCCAT    1740

GTTCAACGAG AACCAGAAGG GAGGCGACGA GACGGGGAGG CACTTCGGCC TCTTCAACCC    1800

GGACCAGTCG CCGGCATACT CCATCAATTT CTAA                               1834

(2) INFORMATION FOR SEQ ID NO:5:

(i) SEQUENCE CHARACTERISTICS:
        (A) LENGTH: 2169 base pairs
        (B) TYPE: nucleic acid
        (C) STRANDEDNESS: single
        (D) TOPOLOGY: linear (xi) SEQUENCE DESCRIPTION: SEQ ID NO:5:

GAATTCCACG AGCCGGACAA GCAACTGCTC GATTTTATCC CGTCGTGCAC GAACGCATGC      60

TCGCGCGCGG CTAACGGTGC ATGATGCGTG CGCGCGTCGT CCGGTTTTCC AAGCGAGCAC     120

GACTGGTCGA CGACTGGCCA GTGGTGGCCA TCGCTAGCTA GCGATTGAGT CGTCGTCGTC     180

GTATGTGCAA ATTGTGCATG CGTGGTTGCG AATTAGGCTT GACCAGACTG TGACACCGTC     240

CCGCGCACGT TAATCCAGTT GGCTTATTTA AAGCAGGTAC AATATTAGAC TATAAACCAG     300

CTATAAACAT ATTTTAAGAA GATAAAAGAA AAAAATAAGA GCAGCGGGCT ACAGATTTGT     360

AACCACCTAC AGCAAAGACT TTAAGATGCA TGTGTGTATA AATCTATGAC AGGTGGGACC     420

AGACGTTAAT AATATAATAC TCCCTCCGTT TCAGCTTATA AGACGTTTTG ACTTTGATGA     480

AAGTCAAATT ATTTCAAGTT TAACTAAGTT TATAATATTT ATAATACTAA ATTAGTTTCA     540

TCAAATCAAA TTGAATATAT TTTTATAATA AATTGTCTTG GTTAAAAATG GTACTACTTT     600

TTTTTTACAA ACTTAATTAA ATTTAAAGCA GTTTGATTTT GACTAAAGTC AAAACGTCTT     660

ATAACTTGAA ACGGAGGAAG TAAATGTTTA TAGATAACTA TTAATATTAT ATGAATTGAC     720

TATTAAATTG ACTATAAATG ATTTAGAGCC AATAGTGGGC TAAACTTGCT CTTAGCGTTA     780

ATTTAGTTGG GTTGGCTGCG TAGTGCGGTG GCGGACACTT GCTCCATCGG TAGTGGAGTA     840

CTACTGGTGG TGTGGAAATT GGAAATCGAT CAGCAAGCTG CTGGAGCTAG TGTCATGGAT     900

GTGAGAAGAA CGTGTGATGT ACCGAACTGG ATAATGCTAC GGACTTGTTG CATGCCTAAA     960

TCTCTCCATA TAAATAGAGA GTGATCGTGA CTAGAGATAC TTGCAGAAGC TGCAAAATAA    1020

GCGAAGATGA CTACGCAAGG ATTTGCTCCC GTGCTTGCAG TAGCATTGCT CCTTGCAGCA    1080

TTTCCTGCAG GTATACTGAG GCATATAGTA CATGCATGTT ATTCAGCAGT GTGCGAGTAC    1140

AGAGCATGTG TGCTCCACAT AATAATTAAG TGTACTAATT AACTAACTCT TGGTTCATGT    1200

TACATGTACG CTTGCTCTGT TGACAAATTA ACAGCGGTTC AGTCCATTGG CGTGTGCTAC    1260

GGCGTGATCG GCAACAACCT GCCGGCGGCG AGCGACGTCG TGAAGCTCTA CAAGTCCAAG    1320

GGGATCGACT CCATGCGCAT CTACTTCCCG AGGAGCGACA TCCTCCAGGC ACTCACCGGC    1380

TCGAACATCG CCCTCACCAT GGACGTCGCC AACGAGAACC TCGCCGGTTC GCCGCCGACG    1440

CCACCGGCCG CGGTCGGCTG GGTCAAGCAG AACGTCCAGG CCTACCCGGG CGTCTCCTTC    1500

CGCTACATCG CCGTCGGCAA CGAGGTCACC GGCGACGACA CGGGCAACAT CCTCCCGGCC    1560
```

-continued

| | |
|---|---|
| ATGAAGAACC TCAACGCCGC GCTCGGCGCG GCCGGCCTCG GCGGCGTCGG GGTGTCGACG | 1620 |
| TCGGTGTCCC AGGGCGTGAT CGCCAACTCC TACCCGCCTT CCAACGGCGT CTTCAACGAC | 1680 |
| GACTACATGT TTGACATCGT GGAGTACCTG GCGAGCACCG GAGCGCCGCT GCTGGTTAAC | 1740 |
| GTGTACCCCT ACTTCGCCTA CGTCGGCGAC ACGAAAGACA TCAGCCTCAA CTACGCCACG | 1800 |
| TTCCAGCCGG GCACGACGGT GACGGACGAC GGCAGCGGGC TGATCTACAC GAGCCTCTTC | 1860 |
| GACGCGATGG TGGATTCCGT CTACGCCGCG CTGGAGGACG CCGGCGCGCC GGACGTCGGC | 1920 |
| GTGGTGGTGT CGGAGACCGG GTGGCCGTCG GCCGGTGGGT TCGGGGCCAG CGTGAGCAAC | 1980 |
| GCGCAGACGT ACAACCAGAA GCTTATCAGC CATGTCCAAG GAGGCACTCC GAAGAGACCA | 2040 |
| GGGGTGGCGT TGGAGACGTA CGTGTTCGCC ATGTTCAACG AGAACCAGAA GACCGGGGCT | 2100 |
| GAGACCGAGA GGCACTTCGG GCTGTTCAAC CCCAACAAGT CGCCGTCCTA CAAAATTAGA | 2160 |
| TTCCACTAG | 2169 |

(2) INFORMATION FOR SEQ ID NO:6:

(i) SEQUENCE CHARACTERISTICS:
        (A) LENGTH: 2810 base pairs
        (B) TYPE: nucleic acid
        (C) STRANDEDNESS: single
        (D) TOPOLOGY: linear (xi) SEQUENCE DESCRIPTION: SEQ ID NO:6:

| | |
|---|---|
| CTGCAGGATC CTGTAAGCTC TGTGTGCTAT TATGCTTGCT GCTGCTGCTG TTGTTGTAAC | 60 |
| ACTAGTGAGT TCCAGCAAGG GACCAAGATC TCAGTTGATT GCTTCAAGAC TTGTTGAGCT | 120 |
| TGTTATGTAG TTTGATTTGT TAAACGCCTG AAATGTGTAC ATAGACGTTG TTTTGTGTGA | 180 |
| TCCAATAATA AAATATGCAA AAGGTAATGT TCAAAATATA TTTGTCCACG ATGCCTGTAC | 240 |
| AATGCATCAT TAATGTCCAC CTTATTACGT ACAGTACCGA TTTATGCAAA GAAATCTTCA | 300 |
| GTACTTAAAT TGATTTATCC TCCGAACTTC CAACCTACTC GAACAGACAG AACACCCATT | 360 |
| TCACTATTTC AGGCATCCAT TTCGACACTT GTAACACATG TTACTTTCTC ATCCACGAAC | 420 |
| CGACTCGTTT GAAATCCAAT CCACGGAAAC TGGGACATCG TGCCACTGAA TTCTCAACAG | 480 |
| CGACATCGCC AAGGTCGAGT AGATTGCGGT CAGAGCAGCG ATATATAGCG TCAGTTTCAG | 540 |
| AGGCGGTTCA TTCGTGGAAG AAGTCCACTA GTAGTACTGT ACCACCACCT GCCGTTACTG | 600 |
| AACGTGCAAA CACCATGTCC ATCGATCTCC CCATCAACCG TATCAAGGGT TTGACGTAAC | 660 |
| CACGTAAAAA CGCATCCCCA GGGGGTCGT GGGGCCCTCG GTAGTTGCTG CACGCTGCAA | 720 |
| AGCCTCCCCC TGTATATATA GACCGCCGCC GCACAGGAGG AGGAAGGAGA GGAGTCGGAA | 780 |
| AGGAGATACA GTTCTCAGAT AGTTTCTGCT ACCTTTGCTG CCGCGCGCTG CAGAAGATCG | 840 |
| GCGAGATGGA TGCTGTGTTG GTTACCGCCG CCATCTTCGG GTTGCTGCTC TGCGGCTGCT | 900 |
| CGGTTTCAGG TGAGTGAACG CATCGGTTGA TCTACTTCTC TGGTGATCAG TTAGTAGTAG | 960 |
| CTAGATTGGT TGTTAGTAGT AGCTACTAGA TTGGTGTTCT CTCTTGTGTT TATCAGTACT | 1020 |
| CCCCTTGCTG CGCCGTTAAT CAGTTTCGAG TATATTTGCG ATGCGTGAAA ACTTCTCTGA | 1080 |
| AACGCGGTTG ATTTCGATCG ATCTTAGTGG GAATGCTTCT TGGAAATTGT TCTTGTCATT | 1140 |
| ATCCGGTTCC TCTCTGTTTT GTTCATTGTG TTATTGGTTA GGATCTGCCA TAATCTTCTC | 1200 |
| TAAAAGCGGT ATCCTTGGAA TATCTTTGCA TGCATTCACG GGTGCACCGT TGGATCAAGC | 1260 |
| AGAGATATTT AGATGTGGTG TTTCTTTACC GGATGTTTTG TTATACCTAT TATGAGTAAA | 1320 |
| TTGGTTCCCG GCTCGGAATA AATCCCAGTC TCTCATTACT CTATCATAAA TTTGTTACTA | 1380 |

```
TACTCCTCAT TCCCGGTCCG GATTGAATCC GCGCGTAACC GAACAAGGCC TTACTGGGGA    1440

TACAATGGAA ATATCTTGGC ATCTTTGTTT CTCTGTCAAT TCAAACCACC GTCTTCAATT    1500

CGTTTCAAAT CTTTTGAAGT GTGGTCGATC TCTCATGGTC AAGTAGAACC GACGGGACCT    1560

AATGTTTGGT TGTAGTACAA TGCACTCCTT AATTATGGAT GGTAACTTTT GATCCACAAG    1620

AACTGTTTCT AGCTTGCCCT TTCCAATTTC AAAATGAGTG TTCCTTTCAT GAAAAGGGTA    1680

ATGTAATCAT ATGCGCATAT ATGCACCTTT GCAGCGATAG TTAGTAAGAA ATCTTTCATC    1740

AAAATGCCGT TAATTAACTA GTGAATCTGT GGAAAGATGA AATGGTAATG TAGTAGTACA    1800

AGCTAGGTTG AGTAGTTTCT TTGCTTGTTT ACCAGTACGT GTATGGCGTG TGTATTGATC    1860

GTGCAGGAGT GGAAGGTATC GGTGTGAACT ATGGCATGAT CGGCAACAAC CTCCCGTCGC    1920

CGGACAAGGT CATCGCCCTG TACAGAGCCA GCAACATCAC CGACATCCGC CTCTTCCACC    1980

CGGACACCAC CGTGCTCGCC GCGCTCCGCG GCTCGGGCCT CGGCGTCGTG CTCGGCACGC    2040

TCAACGAGGA CCTGGCACGC CTCGCCACCG ACGCCTCGTT CGCGGCGTCG TGGGTCCAGT    2100

CGTACGTGCA GCCCTTCGCC GGCGCCGTCC GCTTCCGCTA CATCAACGCC GGCAACGAGG    2160

TCATCCCTGG GGACGAGGCG GCGAGCGTCC TCCCGGCCAT GAGGAACCTC CAGTCGCTGC    2220

GGCCCGCGGG GCTCGGCGTG CCGGTCACGA CGGTCGTCGC GACGTCGGTG CTGGGCTCCT    2280

CGTACCCGCC GTCGCAGGGC GCGTTCTCCG AGGCCGCGCT GCCGACGGTG GCGCCGATCG    2340

TCTCCTTCCT GGCGTCGAGC GGGACGCCCC TGCTGGTGAA CGTGTACCCG TACTTCGCCT    2400

ACTCGGCCGA CCCGTCGTCG GTGCGGCTCG ACTACGCGCT GCTGCTGCCG TCGACGTCGG    2460

CGGCCGTGAC GGACGGCGGT GTCACGTACA CCAACATGTT CGACGCCATC CTGGACGCGG    2520

TGTACGCGGC GCTGGAGAAG GCGGGCGGGC AGGGCCTGGA GGTGGTGGTG TCGGAGACCG    2580

GGTGGCCGTC GGGCGGCGGC GGGGCCGGCG CCAGCGTGGA GAACGCGGCG GCGTACAGCA    2640

ACAACCTGGT GCGCCACGTC GGGCGCGGCA CGCCGCGGCG GCCCGGGAAG GCCGTGGAGA    2700

CGTACATCTT CGCCATGTTC AACGAGAACC AGAAGCCCCG AGGCGTGGAG AGAAACTTCG    2760

GCCTGTTCCA CCCGGACATG AGCGCGGTCT ACCACGTCGA CTTCTCGGCG              2810
```

(2) INFORMATION FOR SEQ ID NO:7:

(i) SEQUENCE CHARACTERISTICS:
        (A) LENGTH: 2612 base pairs
        (B) TYPE: nucleic acid
        (C) STRANDEDNESS: single
        (D) TOPOLOGY: linear (xi) SEQUENCE DESCRIPTION: SEQ ID NO:7:

```
GGATCCTTTG GGATAAAGAT GGCGCCAAAT GTCTGCTTCG ATAATTAATT ATCGATTGCA      60

GGTAGAGCCG TATAGGTGGT TGCCAGGCTT ATTCTTTGTG TTCTTGGTTA GGTTTCTTAA     120

AGAAAGAAAT CCATCCTGCT GAGGAAACAC TGCATGATTG GTTTCAGGAG GAATGCTGCG     180

ACTGTAGCTA TATTTATTTT GTGGGTTTTC AATTTTTTAA TTACCCATTT ATCGTACTGG     240

ACAAAACTTC GGTAATACTC CAGTATTTAG GAGAAGGAAA AGGATAACAA CAATATTGAC     300

ATCAGCATCC TGATTGGACA GATTTCGATT ACAGTACAAA TATATTTCGT ATGGTTCAGA     360

AAAATAACTG TATCTAGTCC ACTGGGCCTA TGATGCGTTC TTACTTCCTT AGACCAGTTC     420

TGTTCTTTCA GTAAAAGTTT GGCTAAACCT ACCTAAATAA TTTAAATAGG TCATATCTGC     480

CATTATTTAT TAGATGTTAC ATCTCAACCA AAATATATAT CTTATTCTGC CAATAGTTTT     540

TCTGATTGAC GAAATGAAAA AGGGTAACAC TTTTGCATTG ATGTTTAAAT CAAACTAAAC     600
```

```
TGATGTTGAT ATCGTTGTCA TCTCAATATG ACATAACACA CCGTCACTGG ATAGGATTAT      660

GTCTTTTCTT AATCTTGTAG TTTTTTTTTT CAACATCAGA CAACCTAAAC CACCATTTTT      720

GCTGTTATCT TTGATTCCAG TGCATCTTTG ACTCTTTGTA TATCTTATCC AGTGTGCTTT      780

GATGAAACAA CTATAATTAG GCAGACCTAG ATGATGCTGT AAACCTAGAT AAGATATAAT      840

CCATTACCAT ATGAACGTAT CTAAACAGCA TCACATTGTC TACAATTACA ACAAAAAAGA     900

CATTGCTGCG GTTTTAATAT CTTTGTTTAT TTCTGGTTGA AAGCGATGTA CTTGGATATA     960

TTTGACTCCA TGGACATTGA CGTTTACTGT TTGCTCCTTG ACGCCAAGTA GAAAATGGTT    1020

TGTGCATTTT GCATCTTATT TTTTGTAGTG TGAATGACGG AATTGGACCT GTGTAGTACG    1080

TTCTATAAGT CCTTAGGTTG GAAACTTGGA ATAGCCAGCA GAAAAGACGT ATAGTGATGT    1140

GGAGTTGTGC ACGGGCTTCA CTTGGAAAAT TTTATCTGGT CCCAACTCTT CTCCTGGGTT    1200

TGTTGGCTAA CCACTCGCCT AATCTAGCTA GGAGTTCAGT TTCTGCAAGT CAGGTTACAC    1260

ACCTAATTCA TTGTTCTTCA TTTCATAATG TTAACCTAAA CATGATAGGT TTGGCATTGC    1320

GGATGTGAAC AAGGCTAATG ATTGCAACTT CTCACAAGTC CACTTAATTT TCTCATCTCA    1380

AATATATATA TATATATATA TATATATATT GCTCCAAAG TTGAAACAAA TATAAATTGA     1440

TCATTTGACT AATGTAAATT GTATCATACA CCCTCCATCC CACAAAATAT GGCATCTTCT    1500

AGTACAACGA ATCTGAATAA AGATATTTAG ATTCGTTGTA CTTGTGTGAT CTCTTCTAGG    1560

TTGATTTTTT TTTATAGATG GAGTAGCTGT ATAATGAATG AAAATTACTG AAAAAAAAAG    1620

TTGTAAGTTG TAACTCATCC GTGTGGCAAA ATGATGCAGG AGCTGAAGGC GCCATTGGTG    1680

TGAACTACGG CATGCTGGGG AACAACCTGC CGTCGCCGGC GCAGGTGATC TCCATGTACA    1740

AGGCCAAGAA CATCAACTAC GTCCGCCTCT TCCACCCGGA CACCGCCGTC CTCGCCGCGC    1800

TCCGCAACTC CGGCATCGGC GTCGTCCTCG GCACGTACAA CGAGGACCTC GCCCGCCTCG    1860

CCTCCGACTC CTCGTTTGCC GCCTCCTGGG TCAGCTCCTA CGTCCAGCCC TTCGCCGGCG    1920

CCGTCACGTT CCGCTACATC AACGCCGGCA ACGAGGTCAT CCCCGGCGAC CCCGCCGCCA    1980

ACGTCCTCCC GGCCATGCGC AACCTCGACG CCGCGCTCAA GGCCGCCGGG ATCAGCGGCA    2040

TCCCGGTCAC CACCGCCGTC GCCACGTCCG TGCTCGGCGT CTCGTACCCG CCGTCGCAGG    2100

GCGCGTTCTC GGAGGGCGCG TCGCCGTACA CTGCGCCGAT CGTCGCCTAC CTCGCGTCCA    2160

GGGGCGCGCC GCTGCTGGTG AACGTGTACC CCTACTTTGC GTACGGCGCG GACCCGAGCA    2220

GCGTGCAGCT CGGGTACGCG CTGCTGTCGG GGTCGCAGTC GGCGTCGGTG ACCGACGGCG    2280

GCGTGACATA CACCAACATG TTCGACGCGA TCGTGGACGC GGGCTACGCG GCGGTGGAGA    2340

AGGCGACGGG CGGGCAGGCG GTGGAGCTGG TGGTGTCGGA GACCGGCTGG CCGTCCGGTG    2400

GCGGCGGCGT GGGCGCCACC GTGGAGAACG CGGCGGCGTA CAACAACAAC CTGATCCGCC    2460

ACGTCTCCGG CGGCGCCGGG ACGCCGCGGC GGCCGGGGAA GCCGGTGGAG ACGTACCTGT    2520

TCGCCATGTT CAACGAGAAC CAGAAGCCCG AGGGCGTGGA GCAGCATTTC GGCCTCTTCC    2580

AGCCCGACAT GACCGAAGTC TACCATGTCG AC                                  2612
```

(2) INFORMATION FOR SEQ ID NO:8:

(i) SEQUENCE CHARACTERISTICS:
        (A) LENGTH: 2184 base pairs
        (B) TYPE: nucleic acid
        (C) STRANDEDNESS: single
        (D) TOPOLOGY: linear (xi) SEQUENCE DESCRIPTION: SEQ ID NO:8:

-continued

```
GGATCCAGGG GACTTAACTT TAGTCCATAT ATTTAGACAC TAATTTAGAG TATTAAATAT      60

AAATTACTTA CAAAACTAAT TCAATAAATG AAAGCTAATT TGCGAGACAA ATTTTTTATG     120

TTTAATTAAT CCATAATTAG AGAATGTTTA CTGTAGCATC ACATAGACTA ATCATGGATT     180

AATTAGGCTC AATAGATTCG TCTCGTGAAT TAGTCCAAGA TTATGGATGG ATTTTATTAA     240

TAGTCTACGT TTAATATTTA TAATTAGTGT TCAAACATCC GATGTGATAG GGACTTAAAA     300

AGTTTAGTCC CATCTAAACA GGGCCACAGT CTATGTGGAG CATGTTCACC GAACACCGAT     360

AAATATTGCA AAGCCCAGAA TGATTTTGGT CCCACATGCC AGAAACTACC ACACCCACAT     420

TTCGGTTCAT TTTCAGCTCA GGAAAATCGT CCAACAATTT CAGCTCAGGA AATTAAATCG     480

TCCGAGAAAG GAACAAGTTT GGAGCCGTTG GGATGAGAGC AATTAGGTCA CGCTTAACTA     540

CAAGTACAGT CTCATTCATC GACATTGATT AGCCAGCAAC TAACCACTTA ACCCCGAGCC     600

AGCCCAAGCG CTCCGTACGT TCGTTGGGCC CCCGCCGCGC AGGCGGAGAC AACGGTCATC     660

CGGCGCGCCG GTCGCTCTCC CTCGCTCGCA CGGCCGCACC ACCCACTTCG CCACGAACCC     720

GACGCGAGCG CGACGTGCAT CTCCCAACAT CCCCGCCATT TCCTCCCCAC CCAAAACCAA     780

CCCGCCCGCG TGCGGCTGGC CCACTTTACA GCGCCTCACC TCCCCCAACC ATAAATCCCC     840

GCCCTTTTCC CCCCCTCTCC ACCACTCACC ACGCTCTCCA CTACACGACT CGTCGCCGTC     900

TTGCTCTGCT GCCTCTCGCG CCCGCGCAGC AGTGAGCAGC AGCAAGAGCA GCAAAATGGC     960

TCTACCCGGG GGCCTCCGCG CCCTCATCCT CGCCGTTGCA TTGCCGCTGC TCTTCCTGTC    1020

CGCTTCAGGT AACGAGAGAT TTGGCAATGC AGGTGGTTTA GTGGAGAGTA GTGTGGTTGA    1080

TTGGTGGAGA GTAGTGTGGT TGATTGTTGG GTTGGTTTGG TTACAGAGGC GGGCACGGTG    1140

GGGATCAACT ATGGGAGGGT GGCGAACGAC CTGCCCAACC CGGCGGCGGT GGTGCAGCTG    1200

ATGAAGCAGC AGGGCATCGC GCAGGTGAAG CTGTACGACA CCGAGCCGAC CGTGCTGCGG    1260

GCGCTGGCCA ACACCGGCAT CAAGGTGGTG GTCGCGCTGC CCAACGAGCA GCTGCTCGCC    1320

GCGGCGTCGC GCCCGTCGTA CGCGCTCGCC TGGGTGCGCC GCAACGTCGC AGCGTACTAC    1380

CCGGCCACGC AGATCCAGGG CATCGCCGTC GGGAACGAGG TGTTCGCCTC GGCCAAGAAC    1440

CTCACGGCGC AGCTCGTCCC GGCGATGACC AACGTGCACG CCGCGCTGGC GAGGCTCAGC    1500

CTTGACAAGC CCGTCAAGGT GTCGTCCCCC ATCGCGCTCA CCGCGCTCGC CGGCTCGTAC    1560

CCGCCGTCGG CCGGCGTGTT CCGGGAGGAC CTCGCCCAGG CGGTCATGAA GCCCATGCTC    1620

GACTTCCTCG CGCAGACCGG CTCGTACCTC ATGGTGAACG CGTACCCGTT CTTCGCGTAC    1680

TCTGGCAATA CTGACGTCAT CTCCCTCGAC TACGCGCTGT TCCGCCCCAA CGCCGGCGTG    1740

CTCGACTCCG GGAGCGGCCT CAAGTACTAC AGCCTCCTCG ACGCCCAGCT CGACGCCGTG    1800

TTCACCGCGG TGAGCAAGCT TGGGAACTAC AATGCCGTGC GCGTCGTGGT GTCGGAGACC    1860

GGGTGGCCGT CCAAGGGTGA CGCCAAGGAG ACCGGCGCCG CGGCGGCCAA CGCCGCGGCC    1920

TACAACGGCA ACCTGGTGCG CCGCGTCCTC TCCGGCAACG CCAGAACGCC GCGCCGCCCC    1980

GACGCCGACA TGGACGTGTA CCTCTTCGCT CTCTTCAACG AGAACCAGAA ACCCGGACCG    2040

ACCTCCGAGC GCAACTACGG CGTGTTCTAC CCGAACCAGC AGAAGGTCTA CGACGTCGAG    2100

TTCGTCCTCG GCGGCAACTC GCTGGCGGCG GCGGCAGCAG CGGCAAGGAC AACGGCGGGC    2160

TCGGCTGGCA GGACAACGGC GGGG                                          2184
```

(2) INFORMATION FOR SEQ ID NO:9:
    (i) SEQUENCE CHARACTERISTICS:

(A) LENGTH: 686 base pairs
        (B) TYPE: nucleic acid
        (C) STRANDEDNESS: single
        (D) TOPOLOGY: linear (xi) SEQUENCE DESCRIPTION: SEQ ID NO:9:

ACTGTTATGA CATGAGGTAT GGATGACTGC CCCTATGAGC TTTGTTTGTT CAGTAAGATC      60

ACAGCTGTTG TATCATATAT TTATAGGATA TTTTTCTGCA ATGCAATTTG TTTTCCTCAG     120

CCTGTTGTAA TTTGACAAAT TTTAAGCACA TCGAGGGCCA TTCCCTCAAA CAACGATACT     180

TCAGTACAAC ATCGAGGGTC ATTCCCTCAA CTTTAAACTT TCATGAGCCT CACTGTACTG     240

AGTACTCTAT GCCGTGATGT GCCGGGTAGT CTTGGAGTTC CAAATTAGCG TGTGTACGTG     300

TGTGGTCAAG AAGGATTCAG AGGTTGGCAT TGGTAGATTT TTTTTTTGAA CAAAGCATTG     360

GAAGATTTTA GCCAGAACCG TCCAACAAGT AGCGGCTTAT TTTGACTTGA GCTCTTAAGT     420

CTGCAGAGGT GTATCTACTC TGCACTCACC CGTGTGCGAC GGGGTTGGCT AACCCAGGAG     480

GAAAGGAAAA AAAACACACG GAGCTTGTTT ATGTGGTGAC GAATGAACAG TAAATGAACG     540

TATGTCAATC CCATTTGTAT TGATCTTGTC CAGTCTTCGC CTGGAAATTC CGAGCAGCGT     600

GACTATAAAA GCAAGCTTGC AGCGTTGCAT TTCTTACAT CCAGATCGAG TTCAAGTGCA     660

ACAGATCAAA CTAGTAGCAG CAGAAG                                          686

(2) INFORMATION FOR SEQ ID NO:10:

(i) SEQUENCE CHARACTERISTICS:
        (A) LENGTH: 607 base pairs
        (B) TYPE: nucleic acid
        (C) STRANDEDNESS: single
        (D) TOPOLOGY: linear (xi) SEQUENCE DESCRIPTION: SEQ ID NO:10:

CAACGTTGTC GGAATACTAG ATTAGGGTTT TCACCCCCAA AGAACATCAC CACAATCTGT      60

TGTTCACCCC CAAAGAACAT CACCACAATC TGTTGTTCGA ACGTCGATCC AATTTTCCGA     120

CCAAAATGAG GATGACCCAC AAACTCTATT TCAAAGTGGC AACTTTCCTG GAGCCACATA     180

TAACAAGATT AGTTCGCCAG CCACCACATA AGCAAGGAGA TAAAGGAAAA AATGAAAATA     240

AAATAATTAC ACCAGTCAAA TAAAGCAATA GAGGATTTGC TAATCAAATT CATCATGAAC     300

ATTGGTTGGA TTCCTTGAGA GGTCAGATTC ATCATCCCGT ATTTATGTCT TGACATTTGG     360

AATTTTGATT TTCTGGCACT ATGGTTTGCA GCTTATCGGG AACCTATTCA GTCTCATCTG     420

CATGCTGAGT GTTTATAGTT TATCCGGAAC AATTCACACA TTCATCTGCT TGCTGAGTAC     480

CAGTATAAAT CAAGCTGCTC TGCTTTGAAC TCTGTAAATT ACATCCAGAA ACCAAGTGAA     540

CTATAGGTGG TCTAGGTACA GAATACGCCA CATTTGTTAC ATCTCTCTAG GTTTGAGACC     600

ACAAGAG                                                               607

(2) INFORMATION FOR SEQ ID NO:11:

(i) SEQUENCE CHARACTERISTICS:
        (A) LENGTH: 320 base pairs
        (B) TYPE: nucleic acid
        (C) STRANDEDNESS: single
        (D) TOPOLOGY: linear (xi) SEQUENCE DESCRIPTION: SEQ ID NO:11:

GAATTCCATG AAGCGGAAGA ATACATGCTG TGTCTAAGTA CGCCAAGAAA ACAGAGGCGA      60

GTTTCCACGT TCATGGAAT TTTTTAGCTC CAACAAGCCG CTGTTTCTGT GGAAAAAATG     120

```
GGAGGAAGAT GGCTAGTTAG GCTGCAAATG CAACGTAGCA GCTAGCTGTA AGCACGCACT      180

TGGGCCGTGG ATGTGAGGAA ATTAATGTGC CTAACTGGCT AGACACTGAA ACTTGTATAT      240

AAAGGGGTGT GCATTGGCAC ATAGCATGCA TAACATTCAG GTTCAGGAGC AGCAGTTGGG      300

AGTAGCTAGC TGGGACAACA                                                  320

(2) INFORMATION FOR SEQ ID NO:12:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (xi) SEQUENCE DESCRIPTION: SEQ ID NO:12:

GAATTCCACG AACGCGGCCC CGGTCGACAG CTAACGAGCT TTTGTTTTTA CGGCCGCGAT       60

TGGTGGACGA CGACCTCGTT TCGCTGCAGT CTTGCGCGCG CGTGTACGCA TTTTCTATAG      120

CGAGATACCA CTACTATCTT GTAGAATTAG GCCGGTGCGG ATCGCGACCA CGCTTGTCTC      180

TACGCTCGAT ATCGTATACT AGCACGTAGC GGGTGGAAAC GGGCGCCAAC AATTGCATGG      240

TACATGCATG CCTGCCAGGA ACTTGTATAA ATAGGGGGTG AATGCTTTTG TTACATCGCA      300

TCGATCTGCA TGCGAAGTCC TGCAGCCTCC GTAGCAGACA CGTACAACGT ACCGAGCAAC      360

CTTAGCTAGT GGCGCCTGAA AATTATTAAG CGCTTCAAG                             399

(2) INFORMATION FOR SEQ ID NO:13:

(i) SEQUENCE CHARACTERISTICS:
        (A) LENGTH: 1026 base pairs
        (B) TYPE: nucleic acid
        (C) STRANDEDNESS: single
        (D) TOPOLOGY: linear (xi) SEQUENCE DESCRIPTION: SEQ ID NO:13:

GAATTCCACG AGCCGGACAA GCAACTGCTC GATTTTATCC CGTCGTGCAC GAACGCATGC       60

TCGCGCGCGG CTAACGGTGC ATGATGCGTG CGCGCGTCGT CCGGTTTTCC AAGCGAGCAC      120

GACTGGTCGA CGACTGGCCA GTGGTGGCCA TCGCTAGCTA GCGATTGAGT CGTCGTCGTC      180

GTATGTGCAA ATTGTGCATG CGTGGTTGCG AATTAGGCTT GACCAGACTG TGACACCGTC      240

CCGCGCACGT TAATCCAGTT GGCTTATTTA AAGCAGGTAC AATATTAGAC TATAAACCAG      300

CTATAAACAT ATTTTAAGAA GATAAAAGAA AAAAATAAGA GCAGCGGGCT ACAGATTTGT      360

AACCACCTAC AGCAAAGACT TTAAGATGCA TGTGTGTATA AATCTATGAC AGGTGGGACC      420

AGACGTTAAT AATATAATAC TCCCTCCGTT TCAGCTTATA AGACGTTTTG ACTTTGATGA      480

AAGTCAAATT ATTTCAAGTT TAACTAAGTT TATAATATTT ATAATACTAA ATTAGTTTCA      540

TCAAATCAAA TTGAATATAT TTTTATAATA AATTGTCTTG GTTAAAAATG GTACTACTTT      600

TTTTTTACAA ACTTAATTAA ATTTAAAGCA GTTTGATTTT GACTAAAGTC AAAACGTCTT      660

ATAACTTGAA ACGGAGGAAG TAAATGTTTA TAGATAACTA TTAATATTAT ATGAATTGAC      720

TATTAAATTG ACTATAAATG ATTTAGAGCC AATAGTGGGC TAAACTTGCT CTTAGCGTTA      780

ATTTAGTTGG GTTGGCTGCG TAGTGCGGTG GCGGACACTT GCTCCATCGG TAGTGGAGTA      840

CTACTGGTGG TGTGGAAATT GGAAATCGAT CAGCAAGCTG CTGGAGCTAG TGTCATGGAT      900

GTGAGAAGAA CGTGTGATGT ACCGAACTGG ATAATGCTAC GGACTTGTTG CATGCCTAAA      960

TCTCTCCATA TAAATAGAGA GTGATCGTGA CTAGAGATAC TTGCAGAAGC TGCAAAATAA     1020

GCGAAG                                                                1026
```

(2) INFORMATION FOR SEQ ID NO:14:

(i) SEQUENCE CHARACTERISTICS:
        (A) LENGTH: 845 base pairs
        (B) TYPE: nucleic acid
        (C) STRANDEDNESS: single
        (D) TOPOLOGY: linear (xi) SEQUENCE DESCRIPTION: SEQ ID NO:14:

```
CTGCAGGATC CTGTAAGCTC TGTGTGCTAT TATGCTTGCT GCTGCTGCTG TTGTTGTAAC      60
ACTAGTGAGT TCCAGCAAGG GACCAAGATC TCAGTTGATT GCTTCAAGAC TTGTTGAGCT     120
TGTTATGTAG TTTGATTTGT TAAACGCCTG AAATGTGTAC ATAGACGTTG TTTTGTGTGA     180
TCCAATAATA AAATATGCAA AAGGTAATGT TCAAAATATA TTTGTCCACG ATGCCTGTAC     240
AATGCATCAT TAATGTCCAC CTTATTACGT ACAGTACCGA TTTATGCAAA GAAATCTTCA     300
GTACTTAAAT TGATTTATCC TCCGAACTTC CAACCTACTC GAACAGACAG AACACCCATT     360
TCACTATTTC AGGCATCCAT TTCGACACTT GTAACACATG TTACTTTCTC ATCCACGAAC     420
CGACTCGTTT GAAATCCAAT CCACGGAAAC TGGGACATCG TGCCACTGAA TTCTCAACAG     480
CGACATCGCC AAGGTCGAGT AGATTGCGGT CAGAGCAGCG ATATATAGCG TCAGTTTCAG     540
AGGCGGTTCA TTCGTGGAAG AAGTCCACTA GTAGTACTGT ACCACCACCT GCCGTTACTG     600
AACGTGCAAA CACCATGTCC ATCGATCTCC CCATCAACCG TATCAAGGGT TTGACGTAAC     660
CACGTAAAAA CGCATCCCCA GGGGGGTCGT GGGGCCCTCG GTAGTTGCTG CACGCTGCAA     720
AGCCTCCCCC TGTATATATA GACCGCCGCC GCACAGGAGG AGGAAGGAGA GGAGTCGGAA     780
AGGAGATACA GTTCTCAGAT AGTTTCTGCT ACCTTTGCTG CCGCGCGCTG CAGAAGATCG     840
GCGAG                                                                 845
```

(2) INFORMATION FOR SEQ ID NO:15:

(i) SEQUENCE CHARACTERISTICS:
        (A) LENGTH: 493 base pairs
        (B) TYPE: nucleic acid
        (C) STRANDEDNESS: single
        (D) TOPOLOGY: linear (xi) SEQUENCE DESCRIPTION: SEQ ID NO:15:

```
GGATCCTTTG GGATAAAGAT GGCGCCAAAT GTCTGCTTCG ATAATTAATT ATCGATTGCA      60
GGTAGAGCCG TATAGGTGGT TGCCAGGCTT ATTCTTTGTG TTCTTGGTTA GGTTTCTTAA     120
AGAAAGAAAT CCATCCTGCT GAGGAAACAC TGCATGATTG GTTTCAGGAG GAATGCTGCG     180
ACTGTAGCTA TATTTATTTT GTGGGTTTTC AATTTTTTAA TTACCCATTT ATCGTACTGG     240
ACAAAACTTC GGTAATACTC CAGTATTTAG GAGAAGGAAA AGGATAACAA CAATATTGAC     300
ATCAGCATCC TGATTGGACA GATTTCGATT ACAGTACAAA TATATTTCGT ATGGTTCAGA     360
AAAATAACTG TATCTAGTCC ACTGGGCCTA TGATGCGTTC TTACTTCCTT AGACCAGTTC     420
TGTTCTTTCA GTAAAAGTTT GGCTAAACCT ACCTAAATAA TTTAAATAGG TCATATCTGC     480
CATTATTTAT TAG                                                         493
```

(2) INFORMATION FOR SEQ ID NO:16:

(i) SEQUENCE CHARACTERISTICS:
        (A) LENGTH: 955 base pairs
        (B) TYPE: nucleic acid
        (C) STRANDEDNESS: single
        (D) TOPOLOGY: linear (xi) SEQUENCE DESCRIPTION: SEQ ID NO:16:

```
GGATCCAGGG GACTTAACTT TAGTCCATAT ATTTAGACAC TAATTTAGAG TATTAAATAT      60
AAATTACTTA CAAAACTAAT TCAATAAATG AAAGCTAATT TGCGAGACAA ATTTTTTATG     120
TTTAATTAAT CCATAATTAG AGAATGTTTA CTGTAGCATC ACATAGACTA ATCATGGATT     180
AATTAGGCTC AATAGATTCG TCTCGTGAAT TAGTCCAAGA TTATGGATGG ATTTTATTAA     240
TAGTCTACGT TTAATATTTA TAATTAGTGT TCAAACATCC GATGTGATAG GGACTTAAAA     300
AGTTTAGTCC CATCTAAACA GGGCCACAGT CTATGTGGAG CATGTTCACC GAACACCGAT     360
AAATATTGCA AAGCCCAGAA TGATTTTGGT CCCACATGCC AGAAACTACC ACACCCACAT     420
TTCGGTTCAT TTTCAGCTCA GGAAAATCGT CCAACAATTT CAGCTCAGGA AATTAAATCG     480
TCCGAGAAAG GAACAAGTTT GGAGCCGTTG GGATGAGAGC AATTAGGTCA CGCTTAACTA     540
CAAGTACAGT CTCATTCATC GACATTGATT AGCCAGCAAC TAACCACTTA ACCCCGAGCC     600
AGCCCAAGCG CTCCGTACGT TCGTTGGGCC CCCGCCGCGC AGGCGGAGAC AACGGTCATC     660
CGGCGCGCCG GTCGCTCTCC CTCGCTCGCA CGGCCGCACC ACCCACTTCG CCACGAACCC     720
GACGCGAGCG CGACGTGCAT CTCCCAACAT CCCCGCCATT TCCTCCCCAC CCAAAACCAA     780
CCCGCCCGCG TGCGGCTGGC CCACTTTACA GCGCCTCACC TCCCCCAACC ATAAATCCCC     840
GCCCTTTTCC CCCCCTCTCC ACCACTCACC ACGCTCTCCA CTACACGACT CGTCGCCGTC     900
TTGCTCTGCT GCCTCTCGCG CCCGCGCAGC AGTGAGCAGC AGCAAGAGCA GCAAA         955
```

(2) INFORMATION FOR SEQ ID NO:17:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...111
        (D) OTHER INFORMATION:

(xi) SEQUENCE DESCRIPTION: SEQ ID NO:17:

```
ATG TCT ATG CAA GGC GTT GTT CCT GTG CTT GCA GCG GCT TTG GCC ATT       48
Met Ser Met Gln Gly Val Val Pro Val Leu Ala Ala Ala Leu Ala Ile
  1               5                  10                  15

GCA GCC TTC GCC TCC TTT CCT TCA GGT ACA CAT ATT GCT AAG CTT CGT       96
Ala Ala Phe Ala Ser Phe Pro Ser Gly Thr His Ile Ala Lys Leu Arg
             20                  25                  30

TAT ATC ATG CGA TCC                                                  111
Tyr Ile Met Arg Ser
         35
```

(2) INFORMATION FOR SEQ ID NO:18:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:18:

Met Ser Met Gln Gly Val Val Pro Val Leu Ala Ala Ala Leu Ala Ile

```
            1               5                  10                 15
Ala Ala Phe Ala Ser Phe Pro Ser Gly Thr His Ile Ala Lys Leu Arg
                20                  25                 30

Tyr Ile Met Arg Ser
        35
```

(2) INFORMATION FOR SEQ ID NO:19:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...90
        (D) OTHER INFORMATION:

(xi) SEQUENCE DESCRIPTION: SEQ ID NO:19:

```
ATG GTG AAT ATA CGA GGT TTC TCC CTG GTT TTT GCA GCT GCA TTG CTG     48
Met Val Asn Ile Arg Gly Phe Ser Leu Val Phe Ala Ala Ala Leu Leu
1               5                  10                 15

CTT CTT GGA GTT TTT ATC TCA ATC CCT GTA GGC GTG CAA TCC             90
Leu Leu Gly Val Phe Ile Ser Ile Pro Val Gly Val Gln Ser
                20                  25                 30
```

(2) INFORMATION FOR SEQ ID NO:20:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:20:

```
Met Val Asn Ile Arg Gly Phe Ser Leu Val Phe Ala Ala Ala Leu Leu
1               5                  10                 15

Leu Leu Gly Val Phe Ile Ser Ile Pro Val Gly Val Gln Ser
                20                  25                 30
```

(2) INFORMATION FOR SEQ ID NO:21:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...88
        (D) OTHER INFORMATION:

(xi) SEQUENCE DESCRIPTION: SEQ ID NO:21:

```
ATG GCC AGG AGA CAG GGA GTT GCT TCT ATG CTT ACA ATT GCT CTG ATC     48
Met Ala Arg Arg Gln Gly Val Ala Ser Met Leu Thr Ile Ala Leu Ile
1               5                  10                 15

ATT GGA GCA TTT GCT TCT GCT CCA ACA AGC TGT GCA ATC C               88
Ile Gly Ala Phe Ala Ser Ala Pro Thr Ser Cys Ala Ile Il
                20                  25                 3
```

(2) INFORMATION FOR SEQ ID NO:22:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: protein (v) FRAGMENT TYPE: internal (xi) SEQUENCE DESCRIPTION: SEQ ID NO:22:

Met Ala Arg Arg Gln Gly Val Ala Ser Met Leu Thr Ile Ala Leu Ile
1               5                  10                  15

Ile Gly Ala Phe Ala Ser Ala Pro Thr Ser Cys Ala Ile Ile
                20                  25                  30

(2) INFORMATION FOR SEQ ID NO:23:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ix) FEATURE:
            (A) NAME/KEY: Coding Sequence
            (B) LOCATION: 1...81
            (D) OTHER INFORMATION:

(xi) SEQUENCE DESCRIPTION: SEQ ID NO:23:

ATG GCA AAG CAT GGC GTT GCT TCC GTT TTA ACA CTG GCA TTG GTC CTT        48
Met Ala Lys His Gly Val Ala Ser Val Leu Thr Leu Ala Leu Val Leu
1               5                  10                  15

GGA GTT GCG GCC ATT CCT ACA GTG GTG CAA TCT                            81
Gly Val Ala Ala Ile Pro Thr Val Val Gln Ser
                20                  25

(2) INFORMATION FOR SEQ ID NO:24:

(i) SEQUENCE CHARACTERISTICS:
            (A) LENGTH: 27 amino acids
            (B) TYPE: amino acid
            (C) STRANDEDNESS: single
            (D) TOPOLOGY: linear (ii) MOLECULE TYPE: protein (v) FRAGMENT TYPE: internal (xi) SEQUENCE DESCRIPTION: SEQ ID NO:24:

Met Ala Lys His Gly Val Ala Ser Val Leu Thr Leu Ala Leu Val Leu
1               5                  10                  15

Gly Val Ala Ala Ile Pro Thr Val Val Gln Ser
                20                  25

(2) INFORMATION FOR SEQ ID NO:25:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ix) FEATURE:
            (A) NAME/KEY: Coding Sequence
            (B) LOCATION: 1...75
            (D) OTHER INFORMATION:

(xi) SEQUENCE DESCRIPTION: SEQ ID NO:25:

```
ATG ACT ACG CAA GGA TTT GCT CCC GTG CTT GCA GTA GCA TTG CTC CTT    48
Met Thr Thr Gln Gly Phe Ala Pro Val Leu Ala Val Ala Leu Leu Leu
 1               5                  10                  15

GCA GCA TTT CCT GCA GCG GTT CAG TCC                                75
Ala Ala Phe Pro Ala Ala Val Gln Ser
             20                  25
```

(2) INFORMATION FOR SEQ ID NO:26:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:26:

```
Met Thr Thr Gln Gly Phe Ala Pro Val Leu Ala Val Ala Leu Leu Leu
 1               5                  10                  15

Ala Ala Phe Pro Ala Ala Val Gln Ser
             20                  25
```

(2) INFORMATION FOR SEQ ID NO:27:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...75
        (D) OTHER INFORMATION:

(xi) SEQUENCE DESCRIPTION: SEQ ID NO:27:

```
ATG GAT GCT GTG TTG GTT ACC GCC GCC ATC TTC GGG TTG CTG CTC TGC    48
Met Asp Ala Val Leu Val Thr Ala Ala Ile Phe Gly Leu Leu Leu Cys
 1               5                  10                  15

GGC TGC TCG GTT TCA GGA GTG GAA GGT                                75
Gly Cys Ser Val Ser Gly Val Glu Gly
             20                  25
```

(2) INFORMATION FOR SEQ ID NO:28:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:28:

```
Met Asp Ala Val Leu Val Thr Ala Ala Ile Phe Gly Leu Leu Leu Cys
 1               5                  10                  15

Gly Cys Ser Val Ser Gly Val Glu Gly
             20                  25
```

(2) INFORMATION FOR SEQ ID NO:29:

(i) SEQUENCE CHARACTERISTICS:

(A) LENGTH: 81 base pairs
(B) TYPE: nucleic acid
(C) STRANDEDNESS: single
(D) TOPOLOGY: linear (ix) FEATURE:
(A) NAME/KEY: Coding Sequence
(B) LOCATION: 1...81
(D) OTHER INFORMATION:

(xi) SEQUENCE DESCRIPTION: SEQ ID NO:29:

```
ATG TTA CAT CTC AAC CAA AAT ATA TAT CTT ATT CTG CCA ATA GTT TTT      48
Met Leu His Leu Asn Gln Asn Ile Tyr Leu Ile Leu Pro Ile Val Phe
 1               5                  10                  15

CTG ATT GAC GAA ATG AAA AAG GCT GAA GGC GCC                          81
Leu Ile Asp Glu Met Lys Lys Ala Glu Gly Ala
                20                  25
```

(2) INFORMATION FOR SEQ ID NO:30:

(i) SEQUENCE CHARACTERISTICS:
(A) LENGTH: 27 amino acids
(B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:30:

```
Met Leu His Leu Asn Gln Asn Ile Tyr Leu Ile Leu Pro Ile Val Phe
 1               5                  10                  15

Leu Ile Asp Glu Met Lys Lys Ala Glu Gly Ala
                20                  25
```

(2) INFORMATION FOR SEQ ID NO:31:

(i) SEQUENCE CHARACTERISTICS:
(A) LENGTH: 84 base pairs
(B) TYPE: nucleic acid
(C) STRANDEDNESS: single
(D) TOPOLOGY: linear (ix) FEATURE:
(A) NAME/KEY: Coding Sequence
(B) LOCATION: 1...84
(D) OTHER INFORMATION:

(xi) SEQUENCE DESCRIPTION: SEQ ID NO:31:

```
ATG GCT CTA CCC GGG GGC CTC CGC GCC CTC ATC CTC GCC GTT GCA TTG      48
Met Ala Leu Pro Gly Gly Leu Arg Ala Leu Ile Leu Ala Val Ala Leu
 1               5                  10                  15

CCG CTG CTC TTC CTG TCC GCT TCA GAG GCG GGC ACG                      84
Pro Leu Leu Phe Leu Ser Ala Ser Glu Ala Gly Thr
                20                  25
```

(2) INFORMATION FOR SEQ ID NO:32:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:32:

```
Met Ala Leu Pro Gly Gly Leu Arg Ala Leu Ile Leu Ala Val Ala Leu
 1               5                  10                  15

Pro Leu Leu Phe Leu Ser Ala Ser Glu Ala Gly Thr
            20                  25
```

(2) INFORMATION FOR SEQ ID NO:33:

(i) SEQUENCE CHARACTERISTICS:
        (A) LENGTH: 924 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...924
        (D) OTHER INFORMATION:

(xi) SEQUENCE DESCRIPTION: SEQ ID NO:33:

```
ATC GGC GTG TGC TAC GGC ATG AAC GGC GAC GGC CTC CCG TCG CGG AGC      48
Ile Gly Val Cys Tyr Gly Met Asn Gly Asp Gly Leu Pro Ser Arg Ser
 1               5                  10                  15

AAC GTC GTG CAG CTC TAC AAG TCC AAC GGC ATC GGC GCC ATG CGC ATC      96
Asn Val Val Gln Leu Tyr Lys Ser Asn Gly Ile Gly Ala Met Arg Ile
                20                  25                  30

TAC TCC GCC GAC CGC GAG GCC CTC GAC GCC CTG CGC GGC TCG GGC ATC     144
Tyr Ser Ala Asp Arg Glu Ala Leu Asp Ala Leu Arg Gly Ser Gly Ile
            35                  40                  45

GAC CTC GCC CTC GAC GTC GGC GAA CGG AAC GAC GTC GGC CAG CTC GCG     192
Asp Leu Ala Leu Asp Val Gly Glu Arg Asn Asp Val Gly Gln Leu Ala
        50                  55                  60

GCC AAC GCG GAC TCC TGG GTC CAG GAC AAC GTG AAG GCT TAC TAC CCG     240
Ala Asn Ala Asp Ser Trp Val Gln Asp Asn Val Lys Ala Tyr Tyr Pro
 65                 70                  75                  80

GAC GTC AAG ATC AAG TAC ATC GTC GTC GGC AAC GAG CTC ACC GGC ACC     288
Asp Val Lys Ile Lys Tyr Ile Val Val Gly Asn Glu Leu Thr Gly Thr
                85                  90                  95

GCG ACG GCG AGC ATC CTC CCG GCC ATG CAG AAC GTC CAG GCC GCC CTC     336
Ala Thr Ala Ser Ile Leu Pro Ala Met Gln Asn Val Gln Ala Ala Leu
            100                 105                 110

GCG TCC GCA GGC CTC GCG AAG ATC AAG GTG ACC ACC GCC ATC AAG ATG     384
Ala Ser Ala Gly Leu Ala Lys Ile Lys Val Thr Thr Ala Ile Lys Met
        115                 120                 125

GAC ACG CTC GCC GCC TCA TCG CCG CCG TCC GCC GTG TTC ACC AAC CCA     432
Asp Thr Leu Ala Ala Ser Ser Pro Pro Ser Ala Val Phe Thr Asn Pro
130                 135                 140

TCC GTC ATG GAG CCC ATC GTG AGG TTC CTC ACC GGC AAC GCG GCG CCG     480
Ser Val Met Glu Pro Ile Val Arg Phe Leu Thr Gly Asn Ala Ala Pro
145                 150                 155                 160

CTC CTG GCC AAC GTG TAC CCC TAC TTC GCG TAC AGG GAC AGC CAG GAC     528
Leu Leu Ala Asn Val Tyr Pro Tyr Phe Ala Tyr Arg Asp Ser Gln Asp
                165                 170                 175

ATC GAC CTC AGC TAC GCG CTC TTC CAG CCG AGC TCG ACC ACG GTG AGC     576
Ile Asp Leu Ser Tyr Ala Leu Phe Gln Pro Ser Ser Thr Thr Val Ser
            180                 185                 190

GAC CCC AAC GGC GGC GGG CTG AGC TAC ACG AAC CTC TTC GAC GCC ATG     624
Asp Pro Asn Gly Gly Gly Leu Ser Tyr Thr Asn Leu Phe Asp Ala Met
        195                 200                 205

GTC GAC GCC GTC CGC GCC GCC GTG GAG AAG GTG AGC GGC GGC GGA AGC     672
Val Asp Ala Val Arg Ala Ala Val Glu Lys Val Ser Gly Gly Gly Ser
    210                 215                 220
```

-continued

```
AGC GTC GTC GAC GTC GTG GTG TCG GAG AGC GGG TGG CCG TCG GAC GGC         720
Ser Val Val Asp Val Val Val Ser Glu Ser Gly Trp Pro Ser Asp Gly
225                 230                 235                 240

GGG AAG GGG GCC ACC GTG GAG AAC GCG CGG GCG TAC AAC CAG AAT CTG         768
Gly Lys Gly Ala Thr Val Glu Asn Ala Arg Ala Tyr Asn Gln Asn Leu
                245                 250                 255

ATC GAC CAC GTC GCC CAA GGC ACG CCG AAG AAG CCC GGG CAG ATG GAG         816
Ile Asp His Val Ala Gln Gly Thr Pro Lys Lys Pro Gly Gln Met Glu
                260                 265                 270

GTG TAC GTG TTC GCC TTG TTC AAC GAG AAC CGG AAG GAA GGC GAC GCC         864
Val Tyr Val Phe Ala Leu Phe Asn Glu Asn Arg Lys Glu Gly Asp Ala
            275                 280                 285

ACG GAG AAG AAG TTT GGG CTG TTC AAT CCA GAC AAG ACA CCG GTT TAC         912
Thr Glu Lys Lys Phe Gly Leu Phe Asn Pro Asp Lys Thr Pro Val Tyr
        290                 295                 300

CCA ATC ACT TTC                                                         924
Pro Ile Thr Phe
305
```

(2) INFORMATION FOR SEQ ID NO:34:

(i) SEQUENCE CHARACTERISTICS:
      (A) LENGTH: 308 amino acids
      (B) TYPE: amino acid
      (C) STRANDEDNESS: single
      (D) TOPOLOGY: linear (ii) MOLECULE TYPE: protein (v) FRAGMENT TYPE: internal (xi) SEQUENCE DESCRIPTION: SEQ ID NO:34:

```
Ile Gly Val Cys Tyr Gly Met Asn Gly Asp Gly Leu Pro Ser Arg Ser
1               5                   10                  15

Asn Val Val Gln Leu Tyr Lys Ser Asn Gly Ile Gly Ala Met Arg Ile
            20                  25                  30

Tyr Ser Ala Asp Arg Glu Ala Leu Asp Ala Leu Arg Gly Ser Gly Ile
        35                  40                  45

Asp Leu Ala Leu Asp Val Gly Glu Arg Asn Asp Val Gly Gln Leu Ala
    50                  55                  60

Ala Asn Ala Asp Ser Trp Val Gln Asp Asn Val Lys Ala Tyr Tyr Pro
65                  70                  75                  80

Asp Val Lys Ile Lys Tyr Ile Val Val Gly Asn Glu Leu Thr Gly Thr
                85                  90                  95

Ala Thr Ala Ser Ile Leu Pro Ala Met Gln Asn Val Gln Ala Ala Leu
            100                 105                 110

Ala Ser Ala Gly Leu Ala Lys Ile Lys Val Thr Thr Ala Ile Lys Met
        115                 120                 125

Asp Thr Leu Ala Ala Ser Ser Pro Pro Ser Ala Val Phe Thr Asn Pro
    130                 135                 140

Ser Val Met Glu Pro Ile Val Arg Phe Leu Thr Gly Asn Ala Ala Pro
145                 150                 155                 160

Leu Leu Ala Asn Val Tyr Pro Tyr Phe Ala Tyr Arg Asp Ser Gln Asp
                165                 170                 175

Ile Asp Leu Ser Tyr Ala Leu Phe Gln Pro Ser Ser Thr Thr Val Ser
            180                 185                 190

Asp Pro Asn Gly Gly Leu Ser Tyr Thr Asn Leu Phe Asp Ala Met
        195                 200                 205

Val Asp Ala Val Arg Ala Ala Val Glu Lys Val Ser Gly Gly Gly Ser
```

```
            210                 215                 220
Ser Val Val Asp Val Val Ser Glu Ser Gly Trp Pro Ser Asp Gly
225                 230                 235                 240

Gly Lys Gly Ala Thr Val Glu Asn Ala Arg Ala Tyr Asn Gln Asn Leu
                245                 250                 255

Ile Asp His Val Ala Gln Gly Thr Pro Lys Lys Pro Gly Gln Met Glu
                260                 265                 270

Val Tyr Val Phe Ala Leu Phe Asn Glu Asn Arg Lys Glu Gly Asp Ala
                275                 280                 285

Thr Glu Lys Lys Phe Gly Leu Phe Asn Pro Asp Lys Thr Pro Val Tyr
290                 295                 300

Pro Ile Thr Phe
305

(2) INFORMATION FOR SEQ ID NO:35:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...918
        (D) OTHER INFORMATION:

(xi) SEQUENCE DESCRIPTION: SEQ ID NO:35:

GTT GGT GTG TGC TAC GGC ATG ATC GGC AAC GAT CTC CCG TCG AAG AGC       48
Val Gly Val Cys Tyr Gly Met Ile Gly Asn Asp Leu Pro Ser Lys Ser
1               5                   10                  15

GAC GTC GTG CAG CTC TAC AAA TCC AAT GGC ATC ACA GAC ATG CGC ATC       96
Asp Val Val Gln Leu Tyr Lys Ser Asn Gly Ile Thr Asp Met Arg Ile
                20                  25                  30

TAC TTG CCC GAC GTC GAG GCC ATG AAC GCC CTG CGC GGC ACA GGC ATC      144
Tyr Leu Pro Asp Val Glu Ala Met Asn Ala Leu Arg Gly Thr Gly Ile
            35                  40                  45

GGC CTC ATC GTC GGC GTC GCC AAC GAC ATC CTC ATC GAC CTC GCC GCC      192
Gly Leu Ile Val Gly Val Ala Asn Asp Ile Leu Ile Asp Leu Ala Ala
50                  55                  60

AAC CCG GCG TCC GCC GCG TCC TGG GTC GAC GCG AAC GTC AAG CCG TTC      240
Asn Pro Ala Ser Ala Ala Ser Trp Val Asp Ala Asn Val Lys Pro Phe
65                  70                  75                  80

GTC CCG GCG GTG AAC ATC AAG TAC ATC GCA GTC GGC AAC GAG ATC TCC      288
Val Pro Ala Val Asn Ile Lys Tyr Ile Ala Val Gly Asn Glu Ile Ser
                85                  90                  95

GGC GAG CCC ACG CAG AAC ATC CTC CCG GTC ATG CAG AAC ATC AAC GCC      336
Gly Glu Pro Thr Gln Asn Ile Leu Pro Val Met Gln Asn Ile Asn Ala
            100                 105                 110

GCC CTG GCC GCG GCG AGC ATC ACC GGC GTC AAG GCG TCC ACG GCG GTG      384
Ala Leu Ala Ala Ala Ser Ile Thr Gly Val Lys Ala Ser Thr Ala Val
        115                 120                 125

AAG CTA GAC GTC GTC ACC AAC ACG TTC CCG CCC TCG GCC GGC GTG TTC      432
Lys Leu Asp Val Val Thr Asn Thr Phe Pro Pro Ser Ala Gly Val Phe
    130                 135                 140

GCG GCG CCC TAC ATG ACG GCC GTG GCC AAG CTC CTG CGA TGC ACC GGC      480
Ala Ala Pro Tyr Met Thr Ala Val Ala Lys Leu Leu Arg Cys Thr Gly
145                 150                 155                 160

GCG CCG CTG CTC GCC AAC ATC TAC CCC TAC TTC GCC TAC ATC GGC AAC      528
Ala Pro Leu Leu Ala Asn Ile Tyr Pro Tyr Phe Ala Tyr Ile Gly Asn
                165                 170                 175
```

```
AAG AAG GAC ATC AGC CTC AAC TAC GCC ACG TTC CAG GCC GGC ACG ACG      576
Lys Lys Asp Ile Ser Leu Asn Tyr Ala Thr Phe Gln Ala Gly Thr Thr
            180                 185                 190

GTG CCC GAC CCC AAC ACC GAC CTG GTG TAC GCC AAC CTG TTC GAC GCC      624
Val Pro Asp Pro Asn Thr Asp Leu Val Tyr Ala Asn Leu Phe Asp Ala
        195                 200                 205

ATG GTC GAC TCC GTC TAC GCC GCG CTG GAC AAG GCC GGC GCG GCG GGC      672
Met Val Asp Ser Val Tyr Ala Ala Leu Asp Lys Ala Gly Ala Ala Gly
    210                 215                 220

GTC AGC ATC GTC GTG TCG GAG AGC GGG TGG CCG TCG GCC GGC GGG GAC      720
Val Ser Ile Val Val Ser Glu Ser Gly Trp Pro Ser Ala Gly Gly Asp
225                 230                 235                 240

TCG GCC ACG ATC GAC ATC GCG CGG ACC TAC GTG CAG AAC CTG ATT AAG      768
Ser Ala Thr Ile Asp Ile Ala Arg Thr Tyr Val Gln Asn Leu Ile Lys
                245                 250                 255

CAT GCG AAG AAG GGG ACG CCG AAG CCG GGG GTG ATC GAG ACG TAC GTG      816
His Ala Lys Lys Gly Thr Pro Lys Pro Gly Val Ile Glu Thr Tyr Val
            260                 265                 270

TTC GCC ATG TTC AAC GAG AAC CAG AAG CCC GGG GAA GCC ACG GAG CAA      864
Phe Ala Met Phe Asn Glu Asn Gln Lys Pro Gly Glu Ala Thr Glu Gln
        275                 280                 285

AAC TTT GGA GCC TTC TAC CCT AAC AAG ACA GCA GTC TAC CCT ATC AAT      912
Asn Phe Gly Ala Phe Tyr Pro Asn Lys Thr Ala Val Tyr Pro Ile Asn
    290                 295                 300

TTC CAG                                                              918
Phe Gln
305
```

(2) INFORMATION FOR SEQ ID NO:36:

(i) SEQUENCE CHARACTERISTICS:
        (A) LENGTH: 306 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:36:

```
Val Gly Val Cys Tyr Gly Met Ile Gly Asn Asp Leu Pro Ser Lys Ser
 1               5                  10                  15

Asp Val Val Gln Leu Tyr Lys Ser Asn Gly Ile Thr Asp Met Arg Ile
             20                  25                  30

Tyr Leu Pro Asp Val Glu Ala Met Asn Ala Leu Arg Gly Thr Gly Ile
         35                  40                  45

Gly Leu Ile Val Gly Val Ala Asn Asp Ile Leu Ile Asp Leu Ala Ala
     50                  55                  60

Asn Pro Ala Ser Ala Ala Ser Trp Val Asp Ala Asn Val Lys Pro Phe
65                  70                  75                  80

Val Pro Ala Val Asn Ile Lys Tyr Ile Ala Val Gly Asn Glu Ile Ser
                 85                  90                  95

Gly Glu Pro Thr Gln Asn Ile Leu Pro Val Met Gln Asn Ile Asn Ala
            100                 105                 110

Ala Leu Ala Ala Ala Ser Ile Thr Gly Val Lys Ala Ser Thr Ala Val
        115                 120                 125

Lys Leu Asp Val Val Thr Asn Thr Phe Pro Pro Ser Ala Gly Val Phe
    130                 135                 140
```

```
Ala Ala Pro Tyr Met Thr Ala Val Ala Lys Leu Leu Arg Cys Thr Gly
145                 150                 155                 160

Ala Pro Leu Leu Ala Asn Ile Tyr Pro Tyr Phe Ala Tyr Ile Gly Asn
                165                 170                 175

Lys Lys Asp Ile Ser Leu Asn Tyr Ala Thr Phe Gln Ala Gly Thr Thr
            180                 185                 190

Val Pro Asp Pro Asn Thr Asp Leu Val Tyr Ala Asn Leu Phe Asp Ala
            195                 200                 205

Met Val Asp Ser Val Tyr Ala Ala Leu Asp Lys Ala Gly Ala Ala Gly
        210                 215                 220

Val Ser Ile Val Val Ser Glu Ser Gly Trp Pro Ser Ala Gly Gly Asp
225                 230                 235                 240

Ser Ala Thr Ile Asp Ile Ala Arg Thr Tyr Val Gln Asn Leu Ile Lys
                245                 250                 255

His Ala Lys Lys Gly Thr Pro Lys Pro Gly Val Ile Glu Thr Tyr Val
            260                 265                 270

Phe Ala Met Phe Asn Glu Asn Gln Lys Pro Gly Glu Ala Thr Glu Gln
        275                 280                 285

Asn Phe Gly Ala Phe Tyr Pro Asn Lys Thr Ala Val Tyr Pro Ile Asn
290                 295                 300

Phe Gln
305
```

(2) INFORMATION FOR SEQ ID NO:37:

(i) SEQUENCE CHARACTERISTICS:
        (A) LENGTH: 909 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...909
        (D) OTHER INFORMATION:

(xi) SEQUENCE DESCRIPTION: SEQ ID NO:37:

```
ATC GGC GTG TGC TAT GGC GTT CTC GGC AAC AAC CTC CCG TCG CGG AGC        48
Ile Gly Val Cys Tyr Gly Val Leu Gly Asn Asn Leu Pro Ser Arg Ser
1               5                   10                  15

GAG GTG GTG CAG CTG TAC AAG TCC AAG GGC ATC AAC GGC ATG CGC ATC        96
Glu Val Val Gln Leu Tyr Lys Ser Lys Gly Ile Asn Gly Met Arg Ile
            20                  25                  30

TAC TAC CCC GAC AAG GAG GCG CTC AAC GCC CTG CGC AAC TCC GGT ATC       144
Tyr Tyr Pro Asp Lys Glu Ala Leu Asn Ala Leu Arg Asn Ser Gly Ile
        35                  40                  45

GCC CTC ATC CTC GAC GTC GGC GAC CAG TTG TCC AAC CTC GCC GCC AGC       192
Ala Leu Ile Leu Asp Val Gly Asp Gln Leu Ser Asn Leu Ala Ala Ser
    50                  55                  60

TCC TCC AAG CCG GCC GCG TGG GTC CGC GAC AAC GTC AGG CCC TAC TAC       240
Ser Ser Lys Pro Ala Ala Trp Val Arg Asp Asn Val Arg Pro Tyr Tyr
65                  70                  75                  80

CCG GCC GTC AAC ATC AAG TAC ATC GCC GTC GGC AAC GAG GTG GAA GGC       288
Pro Ala Val Asn Ile Lys Tyr Ile Ala Val Gly Asn Glu Val Glu Gly
                85                  90                  95

GGC GCC ACG AGT AGC ATC CTC CCG GCC ATC CGC AAC GTC AAC TCC GCC       336
Gly Ala Thr Ser Ser Ile Leu Pro Ala Ile Arg Asn Val Asn Ser Ala
            100                 105                 110

CTG GGC TCG GTC GGC CTC GGG CGC ATC AAG GCG TCC ACC GCG GTG AAG       384
Leu Gly Ser Val Gly Leu Gly Arg Ile Lys Ala Ser Thr Ala Val Lys
```

```
            115                 120                           125
TTC GAC GTC ATC TCC AAC TCC TAC CCA CCC TCC GCC GCG GTC TTC AGG       432
Phe Asp Val Ile Ser Asn Ser Tyr Pro Pro Ser Ala Ala Val Phe Arg
    130                 135                 140

GAC GCC TAC ATG AAG GAC ATC GCG CGC TAC CGA TGC ACC GGC GCG CCG       480
Asp Ala Tyr Met Lys Asp Ile Ala Arg Tyr Arg Cys Thr Gly Ala Pro
145                 150                 155                 160

CTG CTC GCC AAC GTG TAC CCG TAC TTC GCC TAC AGG GGG AAC CCG CGC       528
Leu Leu Ala Asn Val Tyr Pro Tyr Phe Ala Tyr Arg Gly Asn Pro Arg
                165                 170                 175

GAC ATC AGC CTC AAC TAC GCC ACG TTC CGG CCG GGC ACC ACG GTG AGG       576
Asp Ile Ser Leu Asn Tyr Ala Thr Phe Arg Pro Gly Thr Thr Val Arg
        180                 185                 190

GAC CCA AAC AAC GGG CTC ACC TAC ACC AAC CTG TTC GAC GCC ATG ATG       624
Asp Pro Asn Asn Gly Leu Thr Tyr Thr Asn Leu Phe Asp Ala Met Met
            195                 200                 205

GAC GCC GTG TAC GCC GCG CTG GAG AAG GCC GGC GCC GGG AAC GTG AGG       672
Asp Ala Val Tyr Ala Ala Leu Glu Lys Ala Gly Ala Gly Asn Val Arg
                210                 215                 220

GTG GTG GTG TCG GAG AGC GGG TGG CCG TCG GCG GGA GGG TTC GGG GCG       720
Val Val Val Ser Glu Ser Gly Trp Pro Ser Ala Gly Gly Phe Gly Ala
225                 230                 235                 240

AGC GTG GAC AAT GCG AGG GCG TAC AAC CAG GGG CTG ATC GAC CAT GTG       768
Ser Val Asp Asn Ala Arg Ala Tyr Asn Gln Gly Leu Ile Asp His Val
                245                 250                 255

CGT GGC ACG CCC AAG AGG CGC GGG GCA CTG GAG GCG TAC ATA TTC GCC       816
Arg Gly Thr Pro Lys Arg Arg Gly Ala Leu Glu Ala Tyr Ile Phe Ala
        260                 265                 270

ATG TTC AAT GAG AAC CAG AAG AAC GGG GAT CCC ACC GAG AGA AAC TTT       864
Met Phe Asn Glu Asn Gln Lys Asn Gly Asp Pro Thr Glu Arg Asn Phe
            275                 280                 285

GGG CTC TTC TAC CCT AAC AAG TCG CCC GTG TAT CCC ATC CGG TTC           909
Gly Leu Phe Tyr Pro Asn Lys Ser Pro Val Tyr Pro Ile Arg Phe
                290                 295                 300
```

(2) INFORMATION FOR SEQ ID NO:38:

(i) SEQUENCE CHARACTERISTICS:
        (A) LENGTH: 303 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:38:

```
Ile Gly Val Cys Tyr Gly Val Leu Gly Asn Asn Leu Pro Ser Arg Ser
1               5                   10                  15

Glu Val Val Gln Leu Tyr Lys Ser Lys Gly Ile Asn Gly Met Arg Ile
                20                  25                  30

Tyr Tyr Pro Asp Lys Glu Ala Leu Asn Ala Leu Arg Asn Ser Gly Ile
            35                  40                  45

Ala Leu Ile Leu Asp Val Gly Asp Gln Leu Ser Asn Leu Ala Ala Ser
        50                  55                  60

Ser Ser Lys Pro Ala Ala Trp Val Arg Asp Asn Val Arg Pro Tyr Tyr
65                  70                  75                  80

Pro Ala Val Asn Ile Lys Tyr Ile Ala Val Gly Asn Glu Val Glu Gly
                85                  90                  95
```

-continued

```
Gly Ala Thr Ser Ser Ile Leu Pro Ala Ile Arg Asn Val Asn Ser Ala
                100                 105                 110

Leu Gly Ser Val Gly Leu Gly Arg Ile Lys Ala Ser Thr Ala Val Lys
            115                 120                 125

Phe Asp Val Ile Ser Asn Ser Tyr Pro Pro Ser Ala Ala Val Phe Arg
        130                 135                 140

Asp Ala Tyr Met Lys Asp Ile Ala Arg Tyr Arg Cys Thr Gly Ala Pro
145                 150                 155                 160

Leu Leu Ala Asn Val Tyr Pro Tyr Phe Ala Tyr Arg Gly Asn Pro Arg
                165                 170                 175

Asp Ile Ser Leu Asn Tyr Ala Thr Phe Arg Pro Gly Thr Thr Val Arg
            180                 185                 190

Asp Pro Asn Asn Gly Leu Thr Tyr Thr Asn Leu Phe Asp Ala Met Met
        195                 200                 205

Asp Ala Val Tyr Ala Ala Leu Glu Lys Ala Gly Ala Gly Asn Val Arg
210                 215                 220

Val Val Val Ser Glu Ser Gly Trp Pro Ser Ala Gly Gly Phe Gly Ala
225                 230                 235                 240

Ser Val Asp Asn Ala Arg Ala Tyr Asn Gln Gly Leu Ile Asp His Val
                245                 250                 255

Arg Gly Thr Pro Lys Arg Arg Gly Ala Leu Glu Ala Tyr Ile Phe Ala
            260                 265                 270

Met Phe Asn Glu Asn Gln Lys Asn Gly Asp Pro Thr Glu Arg Asn Phe
        275                 280                 285

Gly Leu Phe Tyr Pro Asn Lys Ser Pro Val Tyr Pro Ile Arg Phe
    290                 295                 300

(2) INFORMATION FOR SEQ ID NO:39:

(i) SEQUENCE CHARACTERISTICS:
        (A) LENGTH: 912 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...912
        (D) OTHER INFORMATION:

(xi) SEQUENCE DESCRIPTION: SEQ ID NO:39:

ATC GGC GTG TGC TAC GGC GTG ATC GGG AAC AAC CTG CCG TCG CCG AGC        48
Ile Gly Val Cys Tyr Gly Val Ile Gly Asn Asn Leu Pro Ser Pro Ser
1               5                   10                  15

GAC GTC GTG CAG CTC TAC AAG TCC AAC GGC ATC GAC TCC ATG CGC ATC        96
Asp Val Val Gln Leu Tyr Lys Ser Asn Gly Ile Asp Ser Met Arg Ile
                20                  25                  30

TAC TTC CCA AGA AGC GAC ATC CTC CAG GCC CTC AGC GGC TCA AGC ATC       144
Tyr Phe Pro Arg Ser Asp Ile Leu Gln Ala Leu Ser Gly Ser Ser Ile
            35                  40                  45

GCC CTC ACC ATG GAC GTC GGC AAC GAT CAG CTC GGC TCC CTC GCC TCC       192
Ala Leu Thr Met Asp Val Gly Asn Asp Gln Leu Gly Ser Leu Ala Ser
        50                  55                  60

GAC CCC TCC GCC GCC GCC GCC TTC GTC CAG AAC AAC ATC CAG GCG TTC       240
Asp Pro Ser Ala Ala Ala Ala Phe Val Gln Asn Asn Ile Gln Ala Phe
65                  70                  75                  80

CCG GGC GTC AAC TTC CGC TAC ATC ACC GTC GGC AAC GAG GTT TCC GGC       288
Pro Gly Val Asn Phe Arg Tyr Ile Thr Val Gly Asn Glu Val Ser Gly
                85                  90                  95
```

-continued

```
GGC GAC ACG CAG AAC ATC CTC CCG GCC ATG CAG AAC ATG AAC AGG GGC     336
Gly Asp Thr Gln Asn Ile Leu Pro Ala Met Gln Asn Met Asn Arg Gly
        100                 105                 110

CTC TCC GCC GCC GGG CTC GGG AAC ATC AAG GTG TCG ACG TCG GTG TCC     384
Leu Ser Ala Ala Gly Leu Gly Asn Ile Lys Val Ser Thr Ser Val Ser
        115                 120                 125

CAG GCG GAG GTT GGC AAC GGC TTC CCG CCG TCC GCC GGG ACG TTC TCC     432
Gln Ala Glu Val Gly Asn Gly Phe Pro Pro Ser Ala Gly Thr Phe Ser
130                 135                 140

GCC TCG GAC ATG GGG CCC ATA GGT CAG TAC CTG GGG AGC ACC GGG GGG     480
Ala Ser Asp Met Gly Pro Ile Gly Gln Tyr Leu Gly Ser Thr Gly Gly
145                 150                 155                 160

CCG CTG CTC GCC AAC GTC TAC CCC TAC TTC GCC TAC GTG GCA ACC AGG     528
Pro Leu Leu Ala Asn Val Tyr Pro Tyr Phe Ala Tyr Val Ala Thr Arg
                165                 170                 175

GCC CAG ATC GAC ATC AAC TAC GCG CTC TTC ACG TCG CCG GGC ACG GTG     576
Ala Gln Ile Asp Ile Asn Tyr Ala Leu Phe Thr Ser Pro Gly Thr Val
                180                 185                 190

GTG CAG GAC GGC GGC AAC GCG TAC CAG AAC CTG TTC GAC GCC ATC GTC     624
Val Gln Asp Gly Gly Asn Ala Tyr Gln Asn Leu Phe Asp Ala Ile Val
            195                 200                 205

GAC ACG TTC TAC TCC GCG CTG GAG AGC GCC GGC GCC GGG AGC GTC CCG     672
Asp Thr Phe Tyr Ser Ala Leu Glu Ser Ala Gly Ala Gly Ser Val Pro
210                 215                 220

ATC GTG GTG TCG GAG AGC GGG TGG CCG TCG GCG GGC GGC ACG GCC GCG     720
Ile Val Val Ser Glu Ser Gly Trp Pro Ser Ala Gly Gly Thr Ala Ala
225                 230                 235                 240

AGC GCC GGC AAC GCG CAG ACG TAC AAC CAG AAC CTG ATC AAC CAC GTC     768
Ser Ala Gly Asn Ala Gln Thr Tyr Asn Gln Asn Leu Ile Asn His Val
                245                 250                 255

GGG CAG GGG ACG CCC AAG AGG CCC GGG AGC ATC GAG ACC TAC ATT TTC     816
Gly Gln Gly Thr Pro Lys Arg Pro Gly Ser Ile Glu Thr Tyr Ile Phe
                260                 265                 270

GCC ATG TTC AAC GAG AAC CAG AAG GGA GGC GAC GAG ACG GGG AGG CAC     864
Ala Met Phe Asn Glu Asn Gln Lys Gly Gly Asp Glu Thr Gly Arg His
            275                 280                 285

TTC GGC CTC TTC AAC CCG GAC CAG TCG CCG GCA TAC TCC ATC AAT TTC     912
Phe Gly Leu Phe Asn Pro Asp Gln Ser Pro Ala Tyr Ser Ile Asn Phe
290                 295                 300
```

(2) INFORMATION FOR SEQ ID NO:40:

(i) SEQUENCE CHARACTERISTICS:
  (A) LENGTH: 304 amino acids
  (B) TYPE: amino acid
  (C) STRANDEDNESS: single
  (D) TOPOLOGY: linear (ii) MOLECULE TYPE: protein (v) FRAGMENT TYPE: internal (xi) SEQUENCE DESCRIPTION: SEQ ID NO:40:

```
Ile Gly Val Cys Tyr Gly Val Ile Gly Asn Asn Leu Pro Ser Pro Ser
1               5                   10                  15

Asp Val Val Gln Leu Tyr Lys Ser Asn Gly Ile Asp Ser Met Arg Ile
            20                  25                  30

Tyr Phe Pro Arg Ser Asp Ile Leu Gln Ala Leu Ser Gly Ser Ser Ile
        35                  40                  45

Ala Leu Thr Met Asp Val Gly Asn Asp Gln Leu Gly Ser Leu Ala Ser
50                  55                  60
```

-continued

```
Asp Pro Ser Ala Ala Ala Phe Val Gln Asn Asn Ile Gln Ala Phe
 65                  70                  75                  80

Pro Gly Val Asn Phe Arg Tyr Ile Thr Val Gly Asn Glu Val Ser Gly
                 85                  90                  95

Gly Asp Thr Gln Asn Ile Leu Pro Ala Met Gln Asn Met Asn Arg Gly
            100                 105                 110

Leu Ser Ala Ala Gly Leu Gly Asn Ile Lys Val Ser Thr Ser Val Ser
        115                 120                 125

Gln Ala Glu Val Gly Asn Gly Phe Pro Pro Ser Ala Gly Thr Phe Ser
    130                 135                 140

Ala Ser Asp Met Gly Pro Ile Gly Gln Tyr Leu Gly Ser Thr Gly Gly
145                 150                 155                 160

Pro Leu Leu Ala Asn Val Tyr Pro Tyr Phe Ala Tyr Val Ala Thr Arg
                165                 170                 175

Ala Gln Ile Asp Ile Asn Tyr Ala Leu Phe Thr Ser Pro Gly Thr Val
            180                 185                 190

Val Gln Asp Gly Gly Asn Ala Tyr Gln Asn Leu Phe Asp Ala Ile Val
        195                 200                 205

Asp Thr Phe Tyr Ser Ala Leu Glu Ser Ala Gly Ala Gly Ser Val Pro
    210                 215                 220

Ile Val Val Ser Glu Ser Gly Trp Pro Ser Ala Gly Gly Thr Ala Ala
225                 230                 235                 240

Ser Ala Gly Asn Ala Gln Thr Tyr Asn Gln Asn Leu Ile Asn His Val
                245                 250                 255

Gly Gln Gly Thr Pro Lys Arg Pro Gly Ser Ile Glu Thr Tyr Ile Phe
            260                 265                 270

Ala Met Phe Asn Glu Asn Gln Lys Gly Gly Asp Glu Thr Gly Arg His
        275                 280                 285

Phe Gly Leu Phe Asn Pro Asp Gln Ser Pro Ala Tyr Ser Ile Asn Phe
    290                 295                 300
```

(2) INFORMATION FOR SEQ ID NO:41:

(i) SEQUENCE CHARACTERISTICS:
        (A) LENGTH: 921 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...921
        (D) OTHER INFORMATION:

(xi) SEQUENCE DESCRIPTION: SEQ ID NO:41:

```
ATT GGC GTG TGC TAC GGC GTG ATC GGC AAC AAC CTG CCG GCG GCG AGC      48
Ile Gly Val Cys Tyr Gly Val Ile Gly Asn Asn Leu Pro Ala Ala Ser
 1               5                  10                  15

GAC GTC GTG AAG CTC TAC AAG TCC AAG GGG ATC GAC TCC ATG CGC ATC      96
Asp Val Val Lys Leu Tyr Lys Ser Lys Gly Ile Asp Ser Met Arg Ile
                 20                  25                  30

TAC TTC CCG AGG AGC GAC ATC CTC CAG GCA CTC ACC GGC TCG AAC ATC     144
Tyr Phe Pro Arg Ser Asp Ile Leu Gln Ala Leu Thr Gly Ser Asn Ile
             35                  40                  45

GCC CTC ACC ATG GAC GTC GCC AAC GAG AAC CTC GCC GGT TCG CCG CCG     192
Ala Leu Thr Met Asp Val Ala Asn Glu Asn Leu Ala Gly Ser Pro Pro
         50                  55                  60

ACG CCA CCG GCC GCG GTC GGC TGG GTC AAG CAG AAC GTC CAG GCC TAC     240
Thr Pro Pro Ala Ala Val Gly Trp Val Lys Gln Asn Val Gln Ala Tyr
```

-continued

```
65                      70                      75                      80
CCG GGC GTC TCC TTC CGC TAC ATC GCC GTC GGC AAC GAG GTC ACC GGC        288
Pro Gly Val Ser Phe Arg Tyr Ile Ala Val Gly Asn Glu Val Thr Gly
                        85                      90                      95

GAC GAC ACG GGC AAC ATC CTC CCG GCC ATG AAG AAC CTC AAC GCC GCG        336
Asp Asp Thr Gly Asn Ile Leu Pro Ala Met Lys Asn Leu Asn Ala Ala
                100                     105                     110

CTC GGC GCG GCC GGC CTC GGC GGC GTC GGG GTG TCG ACG TCG GTG TCC        384
Leu Gly Ala Ala Gly Leu Gly Gly Val Gly Val Ser Thr Ser Val Ser
                115                     120                     125

CAG GGC GTG ATC GCC AAC TCC TAC CCG CCT TCC AAC GGC GTC TTC AAC        432
Gln Gly Val Ile Ala Asn Ser Tyr Pro Pro Ser Asn Gly Val Phe Asn
                130                     135                     140

GAC GAC TAC ATG TTT GAC ATC GTG GAG TAC CTG GCG AGC ACC GGA GCG        480
Asp Asp Tyr Met Phe Asp Ile Val Glu Tyr Leu Ala Ser Thr Gly Ala
145                     150                     155                     160

CCG CTG CTG GTT AAC GTG TAC CCC TAC TTC GCC TAC GTC GGC GAC ACG        528
Pro Leu Leu Val Asn Val Tyr Pro Tyr Phe Ala Tyr Val Gly Asp Thr
                165                     170                     175

AAA GAC ATC AGC CTC AAC TAC GCC ACG TTC CAG CCG GGC ACG ACG GTG        576
Lys Asp Ile Ser Leu Asn Tyr Ala Thr Phe Gln Pro Gly Thr Thr Val
                180                     185                     190

ACG GAC GAC GGC AGC GGG CTG ATC TAC ACG AGC CTC TTC GAC GCG ATG        624
Thr Asp Asp Gly Ser Gly Leu Ile Tyr Thr Ser Leu Phe Asp Ala Met
                195                     200                     205

GTG GAT TCC GTC TAC GCC GCG CTG GAG GAC GCC GGC GCG CCG GAC GTC        672
Val Asp Ser Val Tyr Ala Ala Leu Glu Asp Ala Gly Ala Pro Asp Val
                210                     215                     220

GGC GTG GTG GTG TCG GAG ACC GGG TGG CCG TCG GCC GGT GGG TTC GGG        720
Gly Val Val Val Ser Glu Thr Gly Trp Pro Ser Ala Gly Gly Phe Gly
225                     230                     235                     240

GCC AGC GTG AGC AAC GCG CAG ACG TAC AAC CAG AAG CTT ATC AGC CAT        768
Ala Ser Val Ser Asn Ala Gln Thr Tyr Asn Gln Lys Leu Ile Ser His
                        245                     250                     255

GTC CAA GGA GGC ACT CCG AAG AGA CCA GGG GTG GCG TTG GAG ACG TAC        816
Val Gln Gly Gly Thr Pro Lys Arg Pro Gly Val Ala Leu Glu Thr Tyr
                260                     265                     270

GTG TTC GCC ATG TTC AAC GAG AAC CAG AAG ACC GGG GCT GAG ACC GAG        864
Val Phe Ala Met Phe Asn Glu Asn Gln Lys Thr Gly Ala Glu Thr Glu
                275                     280                     285

AGG CAC TTC GGG CTG TTC AAC CCC AAC AAG TCG CCG TCC TAC AAA ATT        912
Arg His Phe Gly Leu Phe Asn Pro Asn Lys Ser Pro Ser Tyr Lys Ile
                290                     295                     300

AGA TTC CAC                                                            921
Arg Phe His
305
```

(2) INFORMATION FOR SEQ ID NO:42:

(i) SEQUENCE CHARACTERISTICS:
        (A) LENGTH: 307 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:42:

```
Ile Gly Val Cys Tyr Gly Val Ile Gly Asn Asn Leu Pro Ala Ala Ser
1               5                   10                  15
```

```
Asp Val Val Lys Leu Tyr Lys Ser Lys Gly Ile Asp Ser Met Arg Ile
                20                  25                  30

Tyr Phe Pro Arg Ser Asp Ile Leu Gln Ala Leu Thr Gly Ser Asn Ile
        35                  40                  45

Ala Leu Thr Met Asp Val Ala Asn Glu Asn Leu Ala Gly Ser Pro Pro
    50                  55                  60

Thr Pro Pro Ala Ala Val Gly Trp Val Lys Gln Asn Val Gln Ala Tyr
65                  70                  75                  80

Pro Gly Val Ser Phe Arg Tyr Ile Ala Val Gly Asn Glu Val Thr Gly
                85                  90                  95

Asp Asp Thr Gly Asn Ile Leu Pro Ala Met Lys Asn Leu Asn Ala Ala
            100                 105                 110

Leu Gly Ala Ala Gly Leu Gly Gly Val Gly Val Ser Thr Ser Val Ser
        115                 120                 125

Gln Gly Val Ile Ala Asn Ser Tyr Pro Pro Ser Asn Gly Val Phe Asn
    130                 135                 140

Asp Asp Tyr Met Phe Asp Ile Val Glu Tyr Leu Ala Ser Thr Gly Ala
145                 150                 155                 160

Pro Leu Leu Val Asn Val Tyr Pro Tyr Phe Ala Tyr Val Gly Asp Thr
                165                 170                 175

Lys Asp Ile Ser Leu Asn Tyr Ala Thr Phe Gln Pro Gly Thr Thr Val
            180                 185                 190

Thr Asp Asp Gly Ser Gly Leu Ile Tyr Thr Ser Leu Phe Asp Ala Met
        195                 200                 205

Val Asp Ser Val Tyr Ala Ala Leu Glu Asp Ala Gly Ala Pro Asp Val
    210                 215                 220

Gly Val Val Val Ser Glu Thr Gly Trp Pro Ser Ala Gly Gly Phe Gly
225                 230                 235                 240

Ala Ser Val Ser Asn Ala Gln Thr Tyr Asn Gln Lys Leu Ile Ser His
                245                 250                 255

Val Gln Gly Gly Thr Pro Lys Arg Pro Gly Val Ala Leu Glu Thr Tyr
            260                 265                 270

Val Phe Ala Met Phe Asn Glu Asn Gln Lys Thr Gly Ala Glu Thr Glu
        275                 280                 285

Arg His Phe Gly Leu Phe Asn Pro Asn Lys Ser Pro Ser Tyr Lys Ile
    290                 295                 300

Arg Phe His
305

(2) INFORMATION FOR SEQ ID NO:43:

(i) SEQUENCE CHARACTERISTICS:
        (A) LENGTH: 933 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...933
        (D) OTHER INFORMATION:

(xi) SEQUENCE DESCRIPTION: SEQ ID NO:43:

ATC GGT GTG AAC TAT GGC ATG ATC GGC AAC AAC CTC CCG TCG CCG GAC      48
Ile Gly Val Asn Tyr Gly Met Ile Gly Asn Asn Leu Pro Ser Pro Asp
 1               5                  10                  15

AAG GTC ATC GCC CTG TAC AGA GCC AGC AAC ATC ACC GAC ATC CGC CTC      96
```

```
                                                   -continued

Lys Val Ile Ala Leu Tyr Arg Ala Ser Asn Ile Thr Asp Ile Arg Leu
            20                  25                  30

TTC CAC CCG GAC ACC ACC GTG CTC GCC GCG CTC CGC GGC TCG GGC CTC    144
Phe His Pro Asp Thr Thr Val Leu Ala Ala Leu Arg Gly Ser Gly Leu
            35                  40                  45

GGC GTC GTG CTC GGC ACG CTC AAC GAG GAC CTG GCA CGC CTC GCC ACC    192
Gly Val Val Leu Gly Thr Leu Asn Glu Asp Leu Ala Arg Leu Ala Thr
 50                  55                  60

GAC GCC TCG TTC GCG GCG TCG TGG GTC CAG TCG TAC GTG CAG CCC TTC    240
Asp Ala Ser Phe Ala Ala Ser Trp Val Gln Ser Tyr Val Gln Pro Phe
 65                  70                  75                  80

GCC GGC GCC GTC CGC TTC CGC TAC ATC AAC GCC GGC AAC GAG GTC ATC    288
Ala Gly Ala Val Arg Phe Arg Tyr Ile Asn Ala Gly Asn Glu Val Ile
                 85                  90                  95

CCT GGG GAC GAG GCG GCG AGC GTC CTC CCG GCC ATG AGG AAC CTC CAG    336
Pro Gly Asp Glu Ala Ala Ser Val Leu Pro Ala Met Arg Asn Leu Gln
            100                 105                 110

TCG CTG CGG CCC GCG GGG CTC GGC GTG CCG GTC ACG ACG GTC GTC GCG    384
Ser Leu Arg Pro Ala Gly Leu Gly Val Pro Val Thr Thr Val Val Ala
            115                 120                 125

ACG TCG GTG CTG GGC TCC TCG TAC CCG CCG TCG CAG GGC GCG TTC TCC    432
Thr Ser Val Leu Gly Ser Ser Tyr Pro Pro Ser Gln Gly Ala Phe Ser
            130                 135                 140

GAG GCC GCG CTG CCG ACG GTG GCG CCG ATC GTC TCC TTC CTG GCG TCG    480
Glu Ala Ala Leu Pro Thr Val Ala Pro Ile Val Ser Phe Leu Ala Ser
145                 150                 155                 160

AGC GGG ACG CCC CTG CTG GTG AAC GTG TAC CCG TAC TTC GCC TAC TCG    528
Ser Gly Thr Pro Leu Leu Val Asn Val Tyr Pro Tyr Phe Ala Tyr Ser
            165                 170                 175

GCC GAC CCG TCG TCG GTG CGG CTC GAC TAC GCG CTG CTG CTG CCG TCG    576
Ala Asp Pro Ser Ser Val Arg Leu Asp Tyr Ala Leu Leu Leu Pro Ser
            180                 185                 190

ACG TCG GCG GCC GTG ACG GAC GGC GGT GTC ACG TAC ACC AAC ATG TTC    624
Thr Ser Ala Ala Val Thr Asp Gly Gly Val Thr Tyr Thr Asn Met Phe
            195                 200                 205

GAC GCC ATC CTG GAC GCG GTG TAC GCG GCG CTG GAG AAG GCG GGC GGG    672
Asp Ala Ile Leu Asp Ala Val Tyr Ala Ala Leu Glu Lys Ala Gly Gly
            210                 215                 220

CAG GGC CTG GAG GTG GTG GTG TCG GAG ACC GGG TGG CCG TCG GGC GGC    720
Gln Gly Leu Glu Val Val Val Ser Glu Thr Gly Trp Pro Ser Gly Gly
225                 230                 235                 240

GGC GGG GCC GGC GCC AGC GTG GAG AAC GCG GCG GCG TAC AGC AAC AAC    768
Gly Gly Ala Gly Ala Ser Val Glu Asn Ala Ala Ala Tyr Ser Asn Asn
            245                 250                 255

CTG GTG CGC CAC GTC GGG CGC GGC ACG CCG CGG CGG CCC GGG AAG GCC    816
Leu Val Arg His Val Gly Arg Gly Thr Pro Arg Arg Pro Gly Lys Ala
            260                 265                 270

GTG GAG ACG TAC ATC TTC GCC ATG TTC AAC GAG AAC CAG AAG CCC CGA    864
Val Glu Thr Tyr Ile Phe Ala Met Phe Asn Glu Asn Gln Lys Pro Arg
            275                 280                 285

GGC GTG GAG AGA AAC TTC GGC CTG TTC CAC CCG GAC ATG AGC GCG GTC    912
Gly Val Glu Arg Asn Phe Gly Leu Phe His Pro Asp Met Ser Ala Val
            290                 295                 300

TAC CAC GTC GAC TTC TCG GCG                                        933
Tyr His Val Asp Phe Ser Ala
305                 310

(2) INFORMATION FOR SEQ ID NO:44:

(i) SEQUENCE CHARACTERISTICS:
```

(A) LENGTH: 311 amino acids
    (B) TYPE: amino acid
    (C) STRANDEDNESS: single
    (D) TOPOLOGY: linear (ii) MOLECULE TYPE: protein (v) FRAGMENT TYPE: internal (xi) SEQUENCE DESCRIPTION: SEQ ID NO:44:

Ile Gly Val Asn Tyr Gly Met Ile Gly Asn Leu Pro Ser Pro Asp
1               5                   10                  15

Lys Val Ile Ala Leu Tyr Arg Ala Ser Asn Ile Thr Asp Ile Arg Leu
            20                  25                  30

Phe His Pro Asp Thr Thr Val Leu Ala Ala Leu Arg Gly Ser Gly Leu
            35                  40                  45

Gly Val Val Leu Gly Thr Leu Asn Glu Asp Leu Ala Arg Leu Ala Thr
        50                  55                  60

Asp Ala Ser Phe Ala Ala Ser Trp Val Gln Ser Tyr Val Gln Pro Phe
65                  70                  75                  80

Ala Gly Ala Val Arg Phe Arg Tyr Ile Asn Ala Gly Asn Glu Val Ile
                85                  90                  95

Pro Gly Asp Glu Ala Ala Ser Val Leu Pro Ala Met Arg Asn Leu Gln
            100                 105                 110

Ser Leu Arg Pro Ala Gly Leu Gly Val Pro Val Thr Thr Val Val Ala
            115                 120                 125

Thr Ser Val Leu Gly Ser Ser Tyr Pro Pro Ser Gln Gly Ala Phe Ser
        130                 135                 140

Glu Ala Ala Leu Pro Thr Val Ala Pro Ile Val Ser Phe Leu Ala Ser
145                 150                 155                 160

Ser Gly Thr Pro Leu Leu Val Asn Val Tyr Pro Tyr Phe Ala Tyr Ser
                165                 170                 175

Ala Asp Pro Ser Ser Val Arg Leu Asp Tyr Ala Leu Leu Leu Pro Ser
            180                 185                 190

Thr Ser Ala Ala Val Thr Asp Gly Gly Val Thr Tyr Thr Asn Met Phe
        195                 200                 205

Asp Ala Ile Leu Asp Ala Val Tyr Ala Ala Leu Glu Lys Ala Gly Gly
210                 215                 220

Gln Gly Leu Glu Val Val Ser Glu Thr Gly Trp Pro Ser Gly Gly
225                 230                 235                 240

Gly Gly Ala Gly Ala Ser Val Glu Asn Ala Ala Tyr Ser Asn Asn
                245                 250                 255

Leu Val Arg His Val Gly Arg Gly Thr Pro Arg Pro Gly Lys Ala
            260                 265                 270

Val Glu Thr Tyr Ile Phe Ala Met Phe Asn Glu Asn Gln Lys Pro Arg
        275                 280                 285

Gly Val Glu Arg Asn Phe Gly Leu Phe His Pro Asp Met Ser Ala Val
290                 295                 300

Tyr His Val Asp Phe Ser Ala
305                 310

(2) INFORMATION FOR SEQ ID NO:45:

(i) SEQUENCE CHARACTERISTICS:
        (A) LENGTH: 939 base pairs
        (B) TYPE: nucleic acid
        (C) STRANDEDNESS: single
        (D) TOPOLOGY: linear (ix) FEATURE:
    (A) NAME/KEY: Coding Sequence
    (B) LOCATION: 1...939
    (D) OTHER INFORMATION:

(xi) SEQUENCE DESCRIPTION: SEQ ID NO:45:

| | | | | | | | | | | | | | | | |
|---|---|---|---|---|---|---|---|---|---|---|---|---|---|---|---|
| ATT | GGT | GTG | AAC | TAC | GGC | ATG | CTG | GGG | AAC | AAC | CTG | CCG | TCG | CCG | GCG | 48 |
| Ile | Gly | Val | Asn | Tyr | Gly | Met | Leu | Gly | Asn | Asn | Leu | Pro | Ser | Pro | Ala | |
| 1 | | | | 5 | | | | | 10 | | | | | 15 | | |

```
ATT GGT GTG AAC TAC GGC ATG CTG GGG AAC AAC CTG CCG TCG CCG GCG      48
Ile Gly Val Asn Tyr Gly Met Leu Gly Asn Asn Leu Pro Ser Pro Ala
  1               5                  10                  15

CAG GTG ATC TCC ATG TAC AAG GCC AAG AAC ATC AAC TAC GTC CGC CTC      96
Gln Val Ile Ser Met Tyr Lys Ala Lys Asn Ile Asn Tyr Val Arg Leu
                 20                  25                  30

TTC CAC CCG GAC ACC GCC GTC CTC GCC GCG CTC CGC AAC TCC GGC ATC     144
Phe His Pro Asp Thr Ala Val Leu Ala Ala Leu Arg Asn Ser Gly Ile
             35                  40                  45

GGC GTC GTC CTC GGC ACG TAC AAC GAG GAC CTC GCC CGC CTC GCC TCC     192
Gly Val Val Leu Gly Thr Tyr Asn Glu Asp Leu Ala Arg Leu Ala Ser
         50                  55                  60

GAC TCC TCG TTT GCC GCC TCC TGG GTC AGC TCC TAC GTC CAG CCC TTC     240
Asp Ser Ser Phe Ala Ala Ser Trp Val Ser Ser Tyr Val Gln Pro Phe
 65                  70                  75                  80

GCC GGC GCC GTC ACG TTC CGC TAC ATC AAC GCC GGC AAC GAG GTC ATC     288
Ala Gly Ala Val Thr Phe Arg Tyr Ile Asn Ala Gly Asn Glu Val Ile
                     85                  90                  95

CCC GGC GAC CCC GCC GCC AAC GTC CTC CCG GCC ATG CGC AAC CTC GAC     336
Pro Gly Asp Pro Ala Ala Asn Val Leu Pro Ala Met Arg Asn Leu Asp
                100                 105                 110

GCC GCG CTC AAG GCC GCC GGG ATC AGC GGC ATC CCG GTC ACC ACC GCC     384
Ala Ala Leu Lys Ala Ala Gly Ile Ser Gly Ile Pro Val Thr Thr Ala
            115                 120                 125

GTC GCC ACG TCC GTG CTC GGC GTC TCG TAC CCG CCG TCG CAG GGC GCG     432
Val Ala Thr Ser Val Leu Gly Val Ser Tyr Pro Pro Ser Gln Gly Ala
        130                 135                 140

TTC TCG GAG GGC GCG TCG CCG TAC ACT GCG CCG ATC GTC GCC TAC CTC     480
Phe Ser Glu Gly Ala Ser Pro Tyr Thr Ala Pro Ile Val Ala Tyr Leu
145                 150                 155                 160

GCG TCC AGG GGC GCG CCG CTG CTG GTG AAC GTG TAC CCC TAC TTT GCG     528
Ala Ser Arg Gly Ala Pro Leu Leu Val Asn Val Tyr Pro Tyr Phe Ala
                165                 170                 175

TAC GGC GCG GAC CCG AGC AGC GTG CAG CTC GGG TAC GCG CTG CTG TCG     576
Tyr Gly Ala Asp Pro Ser Ser Val Gln Leu Gly Tyr Ala Leu Leu Ser
                180                 185                 190

GGG TCG CAG TCG GCG TCG GTG ACC GAC GGC GGC GTG ACA TAC ACC AAC     624
Gly Ser Gln Ser Ala Ser Val Thr Asp Gly Gly Val Thr Tyr Thr Asn
            195                 200                 205

ATG TTC GAC GCG ATC GTG GAC GCG GGC TAC GCG GCG GTG GAG AAG GCG     672
Met Phe Asp Ala Ile Val Asp Ala Gly Tyr Ala Ala Val Glu Lys Ala
210                 215                 220

ACG GGC GGG CAG GCG GTG GAG CTG GTG GTG TCG GAG ACC GGC TGG CCG     720
Thr Gly Gly Gln Ala Val Glu Leu Val Val Ser Glu Thr Gly Trp Pro
225                 230                 235                 240

TCC GGT GGC GGC GGC GTG GGC GCC ACC GTG GAG AAC GCG GCG GCG TAC     768
Ser Gly Gly Gly Gly Val Gly Ala Thr Val Glu Asn Ala Ala Ala Tyr
                245                 250                 255

AAC AAC AAC CTG ATC CGC CAC GTC TCC GGC GGC GCC GGG ACG CCG CGG     816
Asn Asn Asn Leu Ile Arg His Val Ser Gly Gly Ala Gly Thr Pro Arg
                260                 265                 270

CGG CCG GGG AAG CCG GTG GAG ACG TAC CTG TTC GCC ATG TTC AAC GAG     864
Arg Pro Gly Lys Pro Val Glu Thr Tyr Leu Phe Ala Met Phe Asn Glu
            275                 280                 285
```

```
AAC CAG AAG CCC GAG GGC GTG GAG CAG CAT TTC GGC CTC TTC CAG CCC    912
Asn Gln Lys Pro Glu Gly Val Glu Gln His Phe Gly Leu Phe Gln Pro
    290                 295                 300

GAC ATG ACC GAA GTC TAC CAT GTC GAC                                939
Asp Met Thr Glu Val Tyr His Val Asp
305                 310
```

(2) INFORMATION FOR SEQ ID NO:46:

(i) SEQUENCE CHARACTERISTICS:
        (A) LENGTH: 313 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:46:

```
Ile Gly Val Asn Tyr Gly Met Leu Gly Asn Asn Leu Pro Ser Pro Ala
1               5                   10                  15

Gln Val Ile Ser Met Tyr Lys Ala Lys Asn Ile Asn Tyr Val Arg Leu
            20                  25                  30

Phe His Pro Asp Thr Ala Val Leu Ala Ala Leu Arg Asn Ser Gly Ile
        35                  40                  45

Gly Val Val Leu Gly Thr Tyr Asn Glu Asp Leu Ala Arg Leu Ala Ser
    50                  55                  60

Asp Ser Ser Phe Ala Ala Ser Trp Val Ser Ser Tyr Val Gln Pro Phe
65                  70                  75                  80

Ala Gly Ala Val Thr Phe Arg Tyr Ile Asn Ala Gly Asn Glu Val Ile
                85                  90                  95

Pro Gly Asp Pro Ala Ala Asn Val Leu Pro Ala Met Arg Asn Leu Asp
                100                 105                 110

Ala Ala Leu Lys Ala Ala Gly Ile Ser Gly Ile Pro Val Thr Thr Ala
            115                 120                 125

Val Ala Thr Ser Val Leu Gly Val Ser Tyr Pro Pro Ser Gln Gly Ala
    130                 135                 140

Phe Ser Glu Gly Ala Ser Pro Tyr Thr Ala Pro Ile Val Ala Tyr Leu
145                 150                 155                 160

Ala Ser Arg Gly Ala Pro Leu Leu Val Asn Val Tyr Pro Tyr Phe Ala
                165                 170                 175

Tyr Gly Ala Asp Pro Ser Ser Val Gln Leu Gly Tyr Ala Leu Leu Ser
                180                 185                 190

Gly Ser Gln Ser Ala Ser Val Thr Asp Gly Gly Val Thr Tyr Thr Asn
            195                 200                 205

Met Phe Asp Ala Ile Val Asp Ala Gly Tyr Ala Ala Val Glu Lys Ala
        210                 215                 220

Thr Gly Gly Gln Ala Val Glu Leu Val Val Ser Glu Thr Gly Trp Pro
225                 230                 235                 240

Ser Gly Gly Gly Gly Val Gly Ala Thr Val Glu Asn Ala Ala Ala Tyr
                245                 250                 255

Asn Asn Asn Leu Ile Arg His Val Ser Gly Gly Ala Gly Thr Pro Arg
                260                 265                 270

Arg Pro Gly Lys Pro Val Glu Thr Tyr Leu Phe Ala Met Phe Asn Glu
            275                 280                 285

Asn Gln Lys Pro Glu Gly Val Glu Gln His Phe Gly Leu Phe Gln Pro
```

```
                 290                 295                 300
Asp Met Thr Glu Val Tyr His Val Asp
305                 310

(2) INFORMATION FOR SEQ ID NO:47:

(i) SEQUENCE CHARACTERISTICS:
        (A) LENGTH: 1047 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...1047
        (D) OTHER INFORMATION:

(xi) SEQUENCE DESCRIPTION: SEQ ID NO:47:

GTG GGG ATC AAC TAT GGG AGG GTG GCG AAC GAC CTG CCC AAC CCG GCG        48
Val Gly Ile Asn Tyr Gly Arg Val Ala Asn Asp Leu Pro Asn Pro Ala
1               5                   10                  15

GCG GTG GTG CAG CTG ATG AAG CAG CAG GGC ATC GCG CAG GTG AAG CTG        96
Ala Val Val Gln Leu Met Lys Gln Gln Gly Ile Ala Gln Val Lys Leu
            20                  25                  30

TAC GAC ACC GAG CCG ACC GTG CTG CGG GCG CTG GCC AAC ACC GGC ATC       144
Tyr Asp Thr Glu Pro Thr Val Leu Arg Ala Leu Ala Asn Thr Gly Ile
        35                  40                  45

AAG GTG GTG GTC GCG CTG CCC AAC GAG CAG CTG CTC GCC GCG GCG TCG       192
Lys Val Val Val Ala Leu Pro Asn Glu Gln Leu Leu Ala Ala Ala Ser
    50                  55                  60

CGC CCG TCG TAC GCG CTC GCC TGG GTG CGC CGC AAC GTC GCA GCG TAC       240
Arg Pro Ser Tyr Ala Leu Ala Trp Val Arg Arg Asn Val Ala Ala Tyr
65                  70                  75                  80

TAC CCG GCC ACG CAG ATC CAG GGC ATC GCC GTC GGG AAC GAG GTG TTC       288
Tyr Pro Ala Thr Gln Ile Gln Gly Ile Ala Val Gly Asn Glu Val Phe
                85                  90                  95

GCC TCG GCC AAG AAC CTC ACG GCG CAG CTC GTC CCG GCG ATG ACC AAC       336
Ala Ser Ala Lys Asn Leu Thr Ala Gln Leu Val Pro Ala Met Thr Asn
            100                 105                 110

GTG CAC GCC GCG CTG GCG AGG CTC AGC CTT GAC AAG CCC GTC AAG GTG       384
Val His Ala Ala Leu Ala Arg Leu Ser Leu Asp Lys Pro Val Lys Val
        115                 120                 125

TCG TCC CCC ATC GCG CTC ACC GCG CTC GCC GGC TCG TAC CCG CCG TCG       432
Ser Ser Pro Ile Ala Leu Thr Ala Leu Ala Gly Ser Tyr Pro Pro Ser
    130                 135                 140

GCC GGC GTG TTC CGG GAG GAC CTC GCC CAG GCG GTC ATG AAG CCC ATG       480
Ala Gly Val Phe Arg Glu Asp Leu Ala Gln Ala Val Met Lys Pro Met
145                 150                 155                 160

CTC GAC TTC CTC GCG CAG ACC GGC TCG TAC CTC ATG GTG AAC GCG TAC       528
Leu Asp Phe Leu Ala Gln Thr Gly Ser Tyr Leu Met Val Asn Ala Tyr
                165                 170                 175

CCG TTC TTC GCG TAC TCT GGC AAT ACT GAC GTC ATC TCC CTC GAC TAC       576
Pro Phe Phe Ala Tyr Ser Gly Asn Thr Asp Val Ile Ser Leu Asp Tyr
            180                 185                 190

GCG CTG TTC CGC CCC AAC GCC GGC GTG CTC GAC TCC GGG AGC GGC CTC       624
Ala Leu Phe Arg Pro Asn Ala Gly Val Leu Asp Ser Gly Ser Gly Leu
        195                 200                 205

AAG TAC TAC AGC CTC CTC GAC GCC CAG CTC GAC GCC GTG TTC ACC GCG       672
Lys Tyr Tyr Ser Leu Leu Asp Ala Gln Leu Asp Ala Val Phe Thr Ala
    210                 215                 220

GTG AGC AAG CTT GGG AAC TAC AAT GCC GTG CGC GTC GTG GTG TCG GAG       720
Val Ser Lys Leu Gly Asn Tyr Asn Ala Val Arg Val Val Val Ser Glu
```

```
                                                                768
ACC GGG TGG CCG TCC AAG GGT GAC GCC AAG GAG ACC GGC GCC GCG GCG
Thr Gly Trp Pro Ser Lys Gly Asp Ala Lys Glu Thr Gly Ala Ala Ala
225             245             250             255

816
GCC AAC GCC GCG GCC TAC AAC GGC AAC CTG GTG CGC CGC GTC CTC TCC
Ala Asn Ala Ala Ala Tyr Asn Gly Asn Leu Val Arg Arg Val Leu Ser
            260             265             270

864
GGC AAC GCC AGA ACG CCG CGC CGC CCC GAC GCC GAC ATG GAC GTG TAC
Gly Asn Ala Arg Thr Pro Arg Arg Pro Asp Ala Asp Met Asp Val Tyr
            275             280             285

912
CTC TTC GCT CTC TTC AAC GAG AAC CAG AAA CCC GGA CCG ACC TCC GAG
Leu Phe Ala Leu Phe Asn Glu Asn Gln Lys Pro Gly Pro Thr Ser Glu
        290             295             300

960
CGC AAC TAC GGC GTG TTC TAC CCG AAC CAG CAG AAG GTC TAC GAC GTC
Arg Asn Tyr Gly Val Phe Tyr Pro Asn Gln Gln Lys Val Tyr Asp Val
305             310             315             320

1008
GAG TTC GTC CTC GGC GGC AAC TCG CTG GCG GCG GCG GCA GCG GCA
Glu Phe Val Leu Gly Gly Asn Ser Leu Ala Ala Ala Ala Ala Ala
            325             330             335

1047
AGG ACA ACG GCG GGC TCG GCT GGC AGG ACA ACG GCG GGG
Arg Thr Thr Ala Gly Ser Ala Gly Arg Thr Thr Ala Gly
            340             345
```

(2) INFORMATION FOR SEQ ID NO:48:

(i) SEQUENCE CHARACTERISTICS:
        (A) LENGTH: 349 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:48:

```
Val Gly Ile Asn Tyr Gly Arg Val Ala Asn Asp Leu Pro Asn Pro Ala
1               5                   10                  15

Ala Val Val Gln Leu Met Lys Gln Gln Gly Ile Ala Gln Val Lys Leu
            20                  25                  30

Tyr Asp Thr Glu Pro Thr Val Leu Arg Ala Leu Ala Asn Thr Gly Ile
        35                  40                  45

Lys Val Val Ala Leu Pro Asn Glu Gln Leu Leu Ala Ala Ser
    50                  55                  60

Arg Pro Ser Tyr Ala Leu Ala Trp Val Arg Arg Asn Val Ala Ala Tyr
65                  70                  75                  80

Tyr Pro Ala Thr Gln Ile Gln Gly Ile Ala Val Gly Asn Glu Val Phe
            85                  90                  95

Ala Ser Ala Lys Asn Leu Thr Ala Gln Leu Val Pro Ala Met Thr Asn
            100                 105                 110

Val His Ala Ala Leu Ala Arg Leu Ser Leu Asp Lys Pro Val Lys Val
        115                 120                 125

Ser Ser Pro Ile Ala Leu Thr Ala Leu Ala Gly Ser Tyr Pro Pro Ser
    130                 135                 140

Ala Gly Val Phe Arg Glu Asp Leu Ala Gln Ala Val Met Lys Pro Met
145                 150                 155                 160

Leu Asp Phe Leu Ala Gln Thr Gly Ser Tyr Leu Met Val Asn Ala Tyr
            165                 170                 175

Pro Phe Phe Ala Tyr Ser Gly Asn Thr Asp Val Ile Ser Leu Asp Tyr
```

```
                        180               185               190
Ala Leu Phe Arg Pro Asn Ala Gly Val Leu Asp Ser Gly Ser Gly Leu
            195               200               205

Lys Tyr Tyr Ser Leu Leu Asp Ala Gln Leu Asp Ala Val Phe Thr Ala
    210               215               220

Val Ser Lys Leu Gly Asn Tyr Asn Ala Val Arg Val Val Ser Glu
225               230               235               240

Thr Gly Trp Pro Ser Lys Gly Asp Ala Lys Glu Thr Gly Ala Ala Ala
                245               250               255

Ala Asn Ala Ala Ala Tyr Asn Gly Asn Leu Val Arg Val Leu Ser
            260               265               270

Gly Asn Ala Arg Thr Pro Arg Arg Pro Asp Ala Asp Met Asp Val Tyr
            275               280               285

Leu Phe Ala Leu Phe Asn Glu Asn Gln Lys Pro Gly Pro Thr Ser Glu
            290               295               300

Arg Asn Tyr Gly Val Phe Tyr Pro Asn Gln Gln Lys Val Tyr Asp Val
305               310               315               320

Glu Phe Val Leu Gly Gly Asn Ser Leu Ala Ala Ala Ala Ala Ala
                325               330               335

Arg Thr Thr Ala Gly Ser Ala Gly Arg Thr Thr Ala Gly
            340               345

(2) INFORMATION FOR SEQ ID NO:49:

(i) SEQUENCE CHARACTERISTICS:
        (A) LENGTH: 1035 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...1035
        (D) OTHER INFORMATION:

(xi) SEQUENCE DESCRIPTION: SEQ ID NO:49:

ATG TCT ATG CAA GGC GTT GTT CCT GTG CTT GCA GCG GCT TTG GCC ATT        48
Met Ser Met Gln Gly Val Val Pro Val Leu Ala Ala Ala Leu Ala Ile
1               5                   10                  15

GCA GCC TTC GCC TCC TTT CCT TCA GGT ACA CAT ATT GCT AAG CTT CGT        96
Ala Ala Phe Ala Ser Phe Pro Ser Gly Thr His Ile Ala Lys Leu Arg
            20                  25                  30

TAT ATC ATG CGA TCC ATC GGC GTG TGC TAC GGC ATG AAC GGC GAC GGC       144
Tyr Ile Met Arg Ser Ile Gly Val Cys Tyr Gly Met Asn Gly Asp Gly
        35                  40                  45

CTC CCG TCG CGG AGC AAC GTC GTG CAG CTC TAC AAG TCC AAC GGC ATC       192
Leu Pro Ser Arg Ser Asn Val Val Gln Leu Tyr Lys Ser Asn Gly Ile
    50                  55                  60

GGC GCC ATG CGC ATC TAC TCC GCC GAC CGC GAG GCC CTC GAC GCC CTG       240
Gly Ala Met Arg Ile Tyr Ser Ala Asp Arg Glu Ala Leu Asp Ala Leu
65                  70                  75                  80

CGC GGC TCG GGC ATC GAC CTC GCC CTC GAC GTC GGC GAA CGG AAC GAC       288
Arg Gly Ser Gly Ile Asp Leu Ala Leu Asp Val Gly Glu Arg Asn Asp
                85                  90                  95

GTC GGC CAG CTC GCG GCC AAC GCG GAC TCC TGG GTC CAG GAC AAC GTG       336
Val Gly Gln Leu Ala Ala Asn Ala Asp Ser Trp Val Gln Asp Asn Val
            100                 105                 110

AAG GCT TAC TAC CCG GAC GTC AAG ATC AAG TAC ATC GTC GTC GGC AAC       384
Lys Ala Tyr Tyr Pro Asp Val Lys Ile Lys Tyr Ile Val Val Gly Asn
        115                 120                 125
```

```
GAG CTC ACC GGC ACC GCG ACG GCG AGC ATC CTC CCG GCC ATG CAG AAC      432
Glu Leu Thr Gly Thr Ala Thr Ala Ser Ile Leu Pro Ala Met Gln Asn
    130                 135                 140

GTC CAG GCC GCC CTC GCG TCC GCA GGC CTC GCG AAG ATC AAG GTG ACC      480
Val Gln Ala Ala Leu Ala Ser Ala Gly Leu Ala Lys Ile Lys Val Thr
145                 150                 155                 160

ACC GCC ATC AAG ATG GAC ACG CTC GCC GCC TCA TCG CCG CCG TCC GCC      528
Thr Ala Ile Lys Met Asp Thr Leu Ala Ala Ser Ser Pro Pro Ser Ala
                165                 170                 175

GTG TTC ACC AAC CCA TCC GTC ATG GAG CCC ATC GTG AGG TTC CTC ACC      576
Val Phe Thr Asn Pro Ser Val Met Glu Pro Ile Val Arg Phe Leu Thr
                180                 185                 190

GGC AAC GCG GCG CCG CTC CTG GCC AAC GTG TAC CCC TAC TTC GCG TAC      624
Gly Asn Ala Ala Pro Leu Leu Ala Asn Val Tyr Pro Tyr Phe Ala Tyr
            195                 200                 205

AGG GAC AGC CAG GAC ATC GAC CTC AGC TAC GCG CTC TTC CAG CCG AGC      672
Arg Asp Ser Gln Asp Ile Asp Leu Ser Tyr Ala Leu Phe Gln Pro Ser
    210                 215                 220

TCG ACC ACG GTG AGC GAC CCC AAC GGC GGC GGG CTG AGC TAC ACG AAC      720
Ser Thr Thr Val Ser Asp Pro Asn Gly Gly Gly Leu Ser Tyr Thr Asn
225                 230                 235                 240

CTC TTC GAC GCC ATG GTC GAC GCC GTC CGC GCC GCC GTG GAG AAG GTG      768
Leu Phe Asp Ala Met Val Asp Ala Val Arg Ala Ala Val Glu Lys Val
                245                 250                 255

AGC GGC GGC GGA AGC AGC GTC GTC GAC GTC GTG GTG TCG GAG AGC GGG      816
Ser Gly Gly Gly Ser Ser Val Val Asp Val Val Val Ser Glu Ser Gly
                260                 265                 270

TGG CCG TCG GAC GGC GGG AAG GGG GCC ACC GTG GAG AAC GCG CGG GCG      864
Trp Pro Ser Asp Gly Gly Lys Gly Ala Thr Val Glu Asn Ala Arg Ala
            275                 280                 285

TAC AAC CAG AAT CTG ATC GAC CAC GTC GCC CAA GGC ACG CCG AAG AAG      912
Tyr Asn Gln Asn Leu Ile Asp His Val Ala Gln Gly Thr Pro Lys Lys
    290                 295                 300

CCC GGG CAG ATG GAG GTG TAC GTG TTC GCC TTG TTC AAC GAG AAC CGG      960
Pro Gly Gln Met Glu Val Tyr Val Phe Ala Leu Phe Asn Glu Asn Arg
305                 310                 315                 320

AAG GAA GGC GAC GCC ACG GAG AAG AAG TTT GGG CTG TTC AAT CCA GAC     1008
Lys Glu Gly Asp Ala Thr Glu Lys Lys Phe Gly Leu Phe Asn Pro Asp
                325                 330                 335

AAG ACA CCG GTT TAC CCA ATC ACT TTC                                 1035
Lys Thr Pro Val Tyr Pro Ile Thr Phe
            340                 345
```

(2) INFORMATION FOR SEQ ID NO:50:

(i) SEQUENCE CHARACTERISTICS:
        (A) LENGTH: 345 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:50:

```
Met Ser Met Gln Gly Val Val Pro Val Leu Ala Ala Ala Leu Ala Ile
1               5                   10                  15

Ala Ala Phe Ala Ser Phe Pro Ser Gly Thr His Ile Ala Lys Leu Arg
            20                  25                  30

Tyr Ile Met Arg Ser Ile Gly Val Cys Tyr Gly Met Asn Gly Asp Gly
```

```
                35                  40                  45
Leu Pro Ser Arg Ser Asn Val Val Gln Leu Tyr Lys Ser Asn Gly Ile
 50                  55                  60
Gly Ala Met Arg Ile Tyr Ser Ala Asp Arg Glu Ala Leu Asp Ala Leu
 65                  70                  75                  80
Arg Gly Ser Gly Ile Asp Leu Ala Leu Asp Val Gly Glu Arg Asn Asp
                 85                  90                  95
Val Gly Gln Leu Ala Ala Asn Ala Asp Ser Trp Val Gln Asp Asn Val
                100                 105                 110
Lys Ala Tyr Tyr Pro Asp Val Lys Ile Lys Tyr Ile Val Val Gly Asn
                115                 120                 125
Glu Leu Thr Gly Thr Ala Thr Ala Ser Ile Leu Pro Ala Met Gln Asn
                130                 135                 140
Val Gln Ala Ala Leu Ala Ser Ala Gly Leu Ala Lys Ile Lys Val Thr
145                 150                 155                 160
Thr Ala Ile Lys Met Asp Thr Leu Ala Ala Ser Ser Pro Pro Ser Ala
                165                 170                 175
Val Phe Thr Asn Pro Ser Val Met Glu Pro Ile Val Arg Phe Leu Thr
                180                 185                 190
Gly Asn Ala Ala Pro Leu Leu Ala Asn Val Tyr Pro Tyr Phe Ala Tyr
                195                 200                 205
Arg Asp Ser Gln Asp Ile Asp Leu Ser Tyr Ala Leu Phe Gln Pro Ser
210                 215                 220
Ser Thr Thr Val Ser Asp Pro Asn Gly Gly Gly Leu Ser Tyr Thr Asn
225                 230                 235                 240
Leu Phe Asp Ala Met Val Asp Ala Val Arg Ala Ala Val Glu Lys Val
                245                 250                 255
Ser Gly Gly Ser Ser Val Val Asp Val Val Ser Glu Ser Gly
                260                 265                 270
Trp Pro Ser Asp Gly Gly Lys Gly Ala Thr Val Glu Asn Ala Arg Ala
                275                 280                 285
Tyr Asn Gln Asn Leu Ile Asp His Val Ala Gln Gly Thr Pro Lys Lys
                290                 295                 300
Pro Gly Gln Met Glu Val Tyr Val Phe Ala Leu Phe Asn Glu Asn Arg
305                 310                 315                 320
Lys Glu Gly Asp Ala Thr Glu Lys Lys Phe Gly Leu Phe Asn Pro Asp
                325                 330                 335
Lys Thr Pro Val Tyr Pro Ile Thr Phe
                340                 345

(2) INFORMATION FOR SEQ ID NO:51:

(i) SEQUENCE CHARACTERISTICS:
        (A) LENGTH: 1008 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...1008
        (D) OTHER INFORMATION:

(xi) SEQUENCE DESCRIPTION: SEQ ID NO:51:

ATG GTG AAT ATA CGA GGT TTC TCC CTG GTT TTT GCA GCT GCA TTG CTG      48
Met Val Asn Ile Arg Gly Phe Ser Leu Val Phe Ala Ala Ala Leu Leu
 1               5                  10                  15
```

-continued

| | |
|---|---|
| CTT CTT GGA GTT TTT ATC TCA ATC CCT GTA GGC GTG CAA TCC GTT GGT<br>Leu Leu Gly Val Phe Ile Ser Ile Pro Val Gly Val Gln Ser Val Gly<br>              20                    25                    30 | 96 |
| GTG TGC TAC GGC ATG ATC GGC AAC GAT CTC CCG TCG AAG AGC GAC GTC<br>Val Cys Tyr Gly Met Ile Gly Asn Asp Leu Pro Ser Lys Ser Asp Val<br>        35                    40                    45 | 144 |
| GTG CAG CTC TAC AAA TCC AAT GGC ATC ACA GAC ATG CGC ATC TAC TTG<br>Val Gln Leu Tyr Lys Ser Asn Gly Ile Thr Asp Met Arg Ile Tyr Leu<br>    50                    55                    60 | 192 |
| CCC GAC GTC GAG GCC ATG AAC GCC CTG CGC GGC ACA GGC ATC GGC CTC<br>Pro Asp Val Glu Ala Met Asn Ala Leu Arg Gly Thr Gly Ile Gly Leu<br>65                    70                    75                    80 | 240 |
| ATC GTC GGC GTC GCC AAC GAC ATC CTC ATC GAC CTC GCC GCC AAC CCG<br>Ile Val Gly Val Ala Asn Asp Ile Leu Ile Asp Leu Ala Ala Asn Pro<br>              85                    90                    95 | 288 |
| GCG TCC GCC GCG TCC TGG GTC GAC GCG AAC GTC AAG CCG TTC GTC CCG<br>Ala Ser Ala Ala Ser Trp Val Asp Ala Asn Val Lys Pro Phe Val Pro<br>        100                   105                 110 | 336 |
| GCG GTG AAC ATC AAG TAC ATC GCA GTC GGC AAC GAG ATC TCC GGC GAG<br>Ala Val Asn Ile Lys Tyr Ile Ala Val Gly Asn Glu Ile Ser Gly Glu<br>           115                   120                 125 | 384 |
| CCC ACG CAG AAC ATC CTC CCG GTC ATG CAG AAC ATC AAC GCC GCC CTG<br>Pro Thr Gln Asn Ile Leu Pro Val Met Gln Asn Ile Asn Ala Ala Leu<br>   130                     135                 140 | 432 |
| GCC GCG GCG AGC ATC ACC GGC GTC AAG GCG TCC ACG GCG GTG AAG CTA<br>Ala Ala Ala Ser Ile Thr Gly Val Lys Ala Ser Thr Ala Val Lys Leu<br>145                    150                 155               160 | 480 |
| GAC GTC GTC ACC AAC ACG TTC CCG CCC TCG GCC GGC GTG TTC GCG GCG<br>Asp Val Val Thr Asn Thr Phe Pro Pro Ser Ala Gly Val Phe Ala Ala<br>           165                   170                 175 | 528 |
| CCC TAC ATG ACG GCC GTG GCC AAG CTC CTG CGA TGC ACC GGC GCG CCG<br>Pro Tyr Met Thr Ala Val Ala Lys Leu Leu Arg Cys Thr Gly Ala Pro<br>           180                   185                 190 | 576 |
| CTG CTC GCC AAC ATC TAC CCC TAC TTC GCC TAC ATC GGC AAC AAG AAG<br>Leu Leu Ala Asn Ile Tyr Pro Tyr Phe Ala Tyr Ile Gly Asn Lys Lys<br>              195                   200                 205 | 624 |
| GAC ATC AGC CTC AAC TAC GCC ACG TTC CAG GCC GGC ACG ACG GTG CCC<br>Asp Ile Ser Leu Asn Tyr Ala Thr Phe Gln Ala Gly Thr Thr Val Pro<br>   210                     215                 220 | 672 |
| GAC CCC AAC ACC GAC CTG GTG TAC GCC AAC CTG TTC GAC GCC ATG GTC<br>Asp Pro Asn Thr Asp Leu Val Tyr Ala Asn Leu Phe Asp Ala Met Val<br>225                    230                 235               240 | 720 |
| GAC TCC GTC TAC GCC GCG CTG GAC AAG GCC GGC GCG GCG GGC GTC AGC<br>Asp Ser Val Tyr Ala Ala Leu Asp Lys Ala Gly Ala Ala Gly Val Ser<br>           245                   250                 255 | 768 |
| ATC GTC GTG TCG GAG AGC GGG TGG CCG TCG GCC GGC GGG GAC TCG GCC<br>Ile Val Val Ser Glu Ser Gly Trp Pro Ser Ala Gly Gly Asp Ser Ala<br>           260                   265                 270 | 816 |
| ACG ATC GAC ATC GCG CGG ACC TAC GTG CAG AAC CTG ATT AAG CAT GCG<br>Thr Ile Asp Ile Ala Arg Thr Tyr Val Gln Asn Leu Ile Lys His Ala<br>           275                   280                 285 | 864 |
| AAG AAG GGG ACG CCG AAG CCG GGG GTG ATC GAG ACG TAC GTG TTC GCC<br>Lys Lys Gly Thr Pro Lys Pro Gly Val Ile Glu Thr Tyr Val Phe Ala<br>   290                     295                 300 | 912 |
| ATG TTC AAC GAG AAC CAG AAG CCC GGG GAA GCC ACG GAG CAA AAC TTT<br>Met Phe Asn Glu Asn Gln Lys Pro Gly Glu Ala Thr Glu Gln Asn Phe<br>305                    310                 315               320 | 960 |
| GGA GCC TTC TAC CCT AAC AAG ACA GCA GTC TAC CCT ATC AAT TTC CAG<br>Gly Ala Phe Tyr Pro Asn Lys Thr Ala Val Tyr Pro Ile Asn Phe Gln<br>           325                   330                 335 | 1008 |

(2) INFORMATION FOR SEQ ID NO:52:

(i) SEQUENCE CHARACTERISTICS:
        (A) LENGTH: 336 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:52:

```
Met Val Asn Ile Arg Gly Phe Ser Leu Val Phe Ala Ala Ala Leu Leu
 1               5                  10                  15

Leu Leu Gly Val Phe Ile Ser Ile Pro Val Gly Val Gln Ser Val Gly
             20                  25                  30

Val Cys Tyr Gly Met Ile Gly Asn Asp Leu Pro Ser Lys Ser Asp Val
         35                  40                  45

Val Gln Leu Tyr Lys Ser Asn Gly Ile Thr Asp Met Arg Ile Tyr Leu
     50                  55                  60

Pro Asp Val Glu Ala Met Asn Ala Leu Arg Gly Thr Gly Ile Gly Leu
 65                  70                  75                  80

Ile Val Gly Val Ala Asn Asp Ile Leu Ile Asp Leu Ala Ala Asn Pro
                 85                  90                  95

Ala Ser Ala Ala Ser Trp Val Asp Ala Asn Val Lys Pro Phe Val Pro
            100                 105                 110

Ala Val Asn Ile Lys Tyr Ile Ala Val Gly Asn Glu Ile Ser Gly Glu
        115                 120                 125

Pro Thr Gln Asn Ile Leu Pro Val Met Gln Asn Ile Asn Ala Ala Leu
    130                 135                 140

Ala Ala Ala Ser Ile Thr Gly Val Lys Ala Ser Thr Ala Val Lys Leu
145                 150                 155                 160

Asp Val Val Thr Asn Thr Phe Pro Pro Ser Ala Gly Val Phe Ala Ala
                165                 170                 175

Pro Tyr Met Thr Ala Val Ala Lys Leu Leu Arg Cys Thr Gly Ala Pro
            180                 185                 190

Leu Leu Ala Asn Ile Tyr Pro Tyr Phe Ala Tyr Ile Gly Asn Lys Lys
        195                 200                 205

Asp Ile Ser Leu Asn Tyr Ala Thr Phe Gln Ala Gly Thr Thr Val Pro
    210                 215                 220

Asp Pro Asn Thr Asp Leu Val Tyr Ala Asn Leu Phe Asp Ala Met Val
225                 230                 235                 240

Asp Ser Val Tyr Ala Ala Leu Asp Lys Ala Gly Ala Ala Gly Val Ser
                245                 250                 255

Ile Val Val Ser Glu Ser Gly Trp Pro Ser Ala Gly Gly Asp Ser Ala
            260                 265                 270

Thr Ile Asp Ile Ala Arg Thr Tyr Val Gln Asn Leu Ile Lys His Ala
        275                 280                 285

Lys Lys Gly Thr Pro Lys Pro Gly Val Ile Glu Thr Tyr Val Phe Ala
    290                 295                 300

Met Phe Asn Glu Asn Gln Lys Pro Gly Glu Ala Thr Glu Gln Asn Phe
305                 310                 315                 320

Gly Ala Phe Tyr Pro Asn Lys Thr Ala Val Tyr Pro Ile Asn Phe Gln
                325                 330                 335
```

(2) INFORMATION FOR SEQ ID NO:53:

(i) SEQUENCE CHARACTERISTICS:
        (A) LENGTH: 996 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...996
        (D) OTHER INFORMATION:

(xi) SEQUENCE DESCRIPTION: SEQ ID NO:53:

```
ATG GCC AGG AGA CAG GGA GTT GCT TCT ATG CTT ACA ATT GCT CTG ATC        48
Met Ala Arg Arg Gln Gly Val Ala Ser Met Leu Thr Ile Ala Leu Ile
 1               5                  10                  15

ATT GGA GCA TTT GCT TCT GCT CCA ACA ACT GTG CAA TCC ATC GGC GTG        96
Ile Gly Ala Phe Ala Ser Ala Pro Thr Thr Val Gln Ser Ile Gly Val
                20                  25                  30

TGC TAT GGC GTT CTC GGC AAC AAC CTC CCG TCG CGG AGC GAG GTG GTG       144
Cys Tyr Gly Val Leu Gly Asn Asn Leu Pro Ser Arg Ser Glu Val Val
            35                  40                  45

CAG CTG TAC AAG TCC AAG GGC ATC AAC GGC ATG CGC ATC TAC TAC CCC       192
Gln Leu Tyr Lys Ser Lys Gly Ile Asn Gly Met Arg Ile Tyr Tyr Pro
        50                  55                  60

GAC AAG GAG GCG CTC AAC GCC CTG CGC AAC TCC GGT ATC GCC CTC ATC       240
Asp Lys Glu Ala Leu Asn Ala Leu Arg Asn Ser Gly Ile Ala Leu Ile
65                  70                  75                  80

CTC GAC GTC GGC GAC CAG TTG TCC AAC CTC GCC GCC AGC TCC TCC AAG       288
Leu Asp Val Gly Asp Gln Leu Ser Asn Leu Ala Ala Ser Ser Ser Lys
                85                  90                  95

CCG GCC GCG TGG GTC CGC GAC AAC GTC AGG CCC TAC TAC CCG GCC GTC       336
Pro Ala Ala Trp Val Arg Asp Asn Val Arg Pro Tyr Tyr Pro Ala Val
            100                 105                 110

AAC ATC AAG TAC ATC GCC GTC GGC AAC GAG GTG GAA GGC GGC GCC ACG       384
Asn Ile Lys Tyr Ile Ala Val Gly Asn Glu Val Glu Gly Gly Ala Thr
        115                 120                 125

AGT AGC ATC CTC CCG GCC ATC CGC AAC GTC AAC TCC GCC CTG GGC TCG       432
Ser Ser Ile Leu Pro Ala Ile Arg Asn Val Asn Ser Ala Leu Gly Ser
    130                 135                 140

GTC GGC CTC GGG CGC ATC AAG GCG TCC ACC GCG GTG AAG TTC GAC GTC       480
Val Gly Leu Gly Arg Ile Lys Ala Ser Thr Ala Val Lys Phe Asp Val
145                 150                 155                 160

ATC TCC AAC TCC TAC CCA CCC TCC GCC GCG GTC TTC AGG GAC GCC TAC       528
Ile Ser Asn Ser Tyr Pro Pro Ser Ala Ala Val Phe Arg Asp Ala Tyr
                165                 170                 175

ATG AAG GAC ATC GCG CGC TAC CGA TGC ACC GGC GCG CCG CTG CTC GCC       576
Met Lys Asp Ile Ala Arg Tyr Arg Cys Thr Gly Ala Pro Leu Leu Ala
            180                 185                 190

AAC GTG TAC CCG TAC TTC GCC TAC AGG GGG AAC CCG CGC GAC ATC AGC       624
Asn Val Tyr Pro Tyr Phe Ala Tyr Arg Gly Asn Pro Arg Asp Ile Ser
        195                 200                 205

CTC AAC TAC GCC ACG TTC CGG CCG GGC ACC ACG GTG AGG GAC CCA AAC       672
Leu Asn Tyr Ala Thr Phe Arg Pro Gly Thr Thr Val Arg Asp Pro Asn
    210                 215                 220

AAC GGG CTC ACC TAC ACC AAC CTG TTC GAC GCC ATG ATG GAC GCC GTG       720
Asn Gly Leu Thr Tyr Thr Asn Leu Phe Asp Ala Met Met Asp Ala Val
225                 230                 235                 240

TAC GCC GCG CTG GAG AAG GCC GGC GCC GGG AAC GTG AGG GTG GTG GTG       768
Tyr Ala Ala Leu Glu Lys Ala Gly Ala Gly Asn Val Arg Val Val Val
                245                 250                 255
```

```
TCG GAG AGC GGG TGG CCG TCG GCG GGA GGG TTC GGG GCG AGC GTG GAC    816
Ser Glu Ser Gly Trp Pro Ser Ala Gly Gly Phe Gly Ala Ser Val Asp
            260                 265                 270

AAT GCG AGG GCG TAC AAC CAG GGG CTG ATC GAC CAT GTG CGT GGC ACG    864
Asn Ala Arg Ala Tyr Asn Gln Gly Leu Ile Asp His Val Arg Gly Thr
                275                 280                 285

CCC AAG AGG CGC GGG GCA CTG GAG GCG TAC ATA TTC GCC ATG TTC AAT    912
Pro Lys Arg Arg Gly Ala Leu Glu Ala Tyr Ile Phe Ala Met Phe Asn
            290                 295                 300

GAG AAC CAG AAG AAC GGG GAT CCC ACC GAG AGA AAC TTT GGG CTC TTC    960
Glu Asn Gln Lys Asn Gly Asp Pro Thr Glu Arg Asn Phe Gly Leu Phe
305                 310                 315                 320

TAC CCT AAC AAG TCG CCC GTG TAT CCC ATC CGG TTC                    996
Tyr Pro Asn Lys Ser Pro Val Tyr Pro Ile Arg Phe
                325                 330
```

(2) INFORMATION FOR SEQ ID NO:54:

(i) SEQUENCE CHARACTERISTICS:
        (A) LENGTH: 332 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:54:

```
Met Ala Arg Arg Gln Gly Val Ala Ser Met Leu Thr Ile Ala Leu Ile
 1               5                  10                  15

Ile Gly Ala Phe Ala Ser Ala Pro Thr Thr Val Gln Ser Ile Gly Val
                20                  25                  30

Cys Tyr Gly Val Leu Gly Asn Asn Leu Pro Ser Arg Ser Glu Val Val
            35                  40                  45

Gln Leu Tyr Lys Ser Lys Gly Ile Asn Gly Met Arg Ile Tyr Tyr Pro
50                  55                  60

Asp Lys Glu Ala Leu Asn Ala Leu Arg Asn Ser Gly Ile Ala Leu Ile
65                  70                  75                  80

Leu Asp Val Gly Asp Gln Leu Ser Asn Leu Ala Ala Ser Ser Ser Lys
                85                  90                  95

Pro Ala Ala Trp Val Arg Asp Asn Val Arg Pro Tyr Tyr Pro Ala Val
                100                 105                 110

Asn Ile Lys Tyr Ile Ala Val Gly Asn Glu Val Glu Gly Gly Ala Thr
            115                 120                 125

Ser Ser Ile Leu Pro Ala Ile Arg Asn Val Asn Ser Ala Leu Gly Ser
            130                 135                 140

Val Gly Leu Gly Arg Ile Lys Ala Ser Thr Ala Val Lys Phe Asp Val
145                 150                 155                 160

Ile Ser Asn Ser Tyr Pro Pro Ser Ala Ala Val Phe Arg Asp Ala Tyr
                165                 170                 175

Met Lys Asp Ile Ala Arg Tyr Arg Cys Thr Gly Ala Pro Leu Leu Ala
                180                 185                 190

Asn Val Tyr Pro Tyr Phe Ala Tyr Arg Gly Asn Pro Arg Asp Ile Ser
            195                 200                 205

Leu Asn Tyr Ala Thr Phe Arg Pro Gly Thr Thr Val Arg Asp Pro Asn
            210                 215                 220

Asn Gly Leu Thr Tyr Thr Asn Leu Phe Asp Ala Met Met Asp Ala Val
```

```
                225                 230                 235                 240
          Tyr Ala Ala Leu Glu Lys Ala Gly Ala Gly Asn Val Arg Val Val Val
                              245                 250                 255
          Ser Glu Ser Gly Trp Pro Ser Ala Gly Gly Phe Gly Ala Ser Val Asp
                              260                 265                 270
          Asn Ala Arg Ala Tyr Asn Gln Gly Leu Ile Asp His Val Arg Gly Thr
                              275                 280                 285
          Pro Lys Arg Arg Gly Ala Leu Glu Ala Tyr Ile Phe Ala Met Phe Asn
                              290                 295                 300
          Glu Asn Gln Lys Asn Gly Asp Pro Thr Glu Arg Asn Phe Gly Leu Phe
          305                 310                 315                 320
          Tyr Pro Asn Lys Ser Pro Val Tyr Pro Ile Arg Phe
                              325                 330

(2) INFORMATION FOR SEQ ID NO:55:

(i) SEQUENCE CHARACTERISTICS:
        (A) LENGTH: 993 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...993
        (D) OTHER INFORMATION:

(xi) SEQUENCE DESCRIPTION: SEQ ID NO:55:

ATG GCA AAG CAT GGC GTT GCT TCC GTT TTA ACA CTG GCA TTG GTC CTT        48
Met Ala Lys His Gly Val Ala Ser Val Leu Thr Leu Ala Leu Val Leu
 1               5                  10                  15

GGA GTT GCG GCC ATT CCT ACA GTG GTG CAA TCT ATC GGC GTG TGC TAC        96
Gly Val Ala Ala Ile Pro Thr Val Val Gln Ser Ile Gly Val Cys Tyr
                20                  25                  30

GGC GTG ATC GGG AAC AAC CTG CCG TCG CCG AGC GAC GTC GTG CAG CTC       144
Gly Val Ile Gly Asn Asn Leu Pro Ser Pro Ser Asp Val Val Gln Leu
            35                  40                  45

TAC AAG TCC AAC GGC ATC GAC TCC ATG CGC ATC TAC TTC CCA AGA AGC       192
Tyr Lys Ser Asn Gly Ile Asp Ser Met Arg Ile Tyr Phe Pro Arg Ser
 50                  55                  60

GAC ATC CTC CAG GCC CTC AGC GGC TCA AGC ATC GCC CTC ACC ATG GAC       240
Asp Ile Leu Gln Ala Leu Ser Gly Ser Ser Ile Ala Leu Thr Met Asp
 65                  70                  75                  80

GTC GGC AAC GAT CAG CTC GGC TCC CTC GCC TCC GAC CCC TCC GCC GCC       288
Val Gly Asn Asp Gln Leu Gly Ser Leu Ala Ser Asp Pro Ser Ala Ala
                85                  90                  95

GCC GCC TTC GTC CAG AAC AAC ATC CAG GCG TTC CCG GGC GTC AAC TTC       336
Ala Ala Phe Val Gln Asn Asn Ile Gln Ala Phe Pro Gly Val Asn Phe
                100                 105                 110

CGC TAC ATC ACC GTC GGC AAC GAG GTT TCC GGC GGC GAC ACG CAG AAC       384
Arg Tyr Ile Thr Val Gly Asn Glu Val Ser Gly Gly Asp Thr Gln Asn
            115                 120                 125

ATC CTC CCG GCC ATG CAG AAC ATG AAC AGG GGC CTC TCC GCC GCC GGG       432
Ile Leu Pro Ala Met Gln Asn Met Asn Arg Gly Leu Ser Ala Ala Gly
130                 135                 140

CTC GGG AAC ATC AAG GTG TCG ACG TCG GTG TCC CAG GCG GAG GTT GGC       480
Leu Gly Asn Ile Lys Val Ser Thr Ser Val Ser Gln Ala Glu Val Gly
145                 150                 155                 160

AAC GGC TTC CCG CCG TCC GCC GGG ACG TTC TCC GCC TCG GAC ATG GGG       528
Asn Gly Phe Pro Pro Ser Ala Gly Thr Phe Ser Ala Ser Asp Met Gly
                165                 170                 175
```

```
CCC ATA GGT CAG TAC CTG GGG AGC ACC GGG GGG CCG CTC GCC AAC    576
Pro Ile Gly Gln Tyr Leu Gly Ser Thr Gly Gly Pro Leu Leu Ala Asn
            180                 185                 190

GTC TAC CCC TAC TTC GCC TAC GTG GCA ACC AGG GCC CAG ATC GAC ATC    624
Val Tyr Pro Tyr Phe Ala Tyr Val Ala Thr Arg Ala Gln Ile Asp Ile
            195                 200                 205

AAC TAC GCG CTC TTC ACG TCG CCG GGC ACG GTG GTG CAG GAC GGC GGC    672
Asn Tyr Ala Leu Phe Thr Ser Pro Gly Thr Val Val Gln Asp Gly Gly
            210                 215                 220

AAC GCG TAC CAG AAC CTG TTC GAC GCC ATC GTC GAC ACG TTC TAC TCC    720
Asn Ala Tyr Gln Asn Leu Phe Asp Ala Ile Val Asp Thr Phe Tyr Ser
225                 230                 235                 240

GCG CTG GAG AGC GCC GGC GCC GGG AGC GTC CCG ATC GTG GTG TCG GAG    768
Ala Leu Glu Ser Ala Gly Ala Gly Ser Val Pro Ile Val Val Ser Glu
                245                 250                 255

AGC GGG TGG CCG TCG GCG GGC GGC ACG GCC GCG AGC GCC GGC AAC GCG    816
Ser Gly Trp Pro Ser Ala Gly Gly Thr Ala Ala Ser Ala Gly Asn Ala
            260                 265                 270

CAG ACG TAC AAC CAG AAC CTG ATC AAC CAC GTC GGG CAG GGG ACG CCC    864
Gln Thr Tyr Asn Gln Asn Leu Ile Asn His Val Gly Gln Gly Thr Pro
            275                 280                 285

AAG AGG CCC GGG AGC ATC GAG ACC TAC ATT TTC GCC ATG TTC AAC GAG    912
Lys Arg Pro Gly Ser Ile Glu Thr Tyr Ile Phe Ala Met Phe Asn Glu
290                 295                 300

AAC CAG AAG GGA GGC GAC GAG ACG GGG AGG CAC TTC GGC CTC TTC AAC    960
Asn Gln Lys Gly Gly Asp Glu Thr Gly Arg His Phe Gly Leu Phe Asn
305                 310                 315                 320

CCG GAC CAG TCG CCG GCA TAC TCC ATC AAT TTC                        993
Pro Asp Gln Ser Pro Ala Tyr Ser Ile Asn Phe
                325                 330

(2) INFORMATION FOR SEQ ID NO:56:

(i) SEQUENCE CHARACTERISTICS:
        (A) LENGTH: 331 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:56:

Met Ala Lys His Gly Val Ala Ser Val Leu Thr Ala Leu Val Leu
1               5                   10                  15

Gly Val Ala Ala Ile Pro Thr Val Gln Ser Ile Gly Val Cys Tyr
                20                  25                  30

Gly Val Ile Gly Asn Asn Leu Pro Ser Pro Ser Asp Val Val Gln Leu
            35                  40                  45

Tyr Lys Ser Asn Gly Ile Asp Ser Met Arg Ile Tyr Phe Pro Arg Ser
    50                  55                  60

Asp Ile Leu Gln Ala Leu Ser Gly Ser Ser Ile Ala Leu Thr Met Asp
65                  70                  75                  80

Val Gly Asn Asp Gln Leu Gly Ser Leu Ala Ser Asp Pro Ser Ala Ala
                85                  90                  95

Ala Ala Phe Val Gln Asn Asn Ile Gln Ala Phe Pro Gly Val Asn Phe
                100                 105                 110

Arg Tyr Ile Thr Val Gly Asn Glu Val Ser Gly Gly Asp Thr Gln Asn
            115                 120                 125
```

```
Ile Leu Pro Ala Met Gln Asn Met Asn Arg Gly Leu Ser Ala Ala Gly
    130                 135                 140

Leu Gly Asn Ile Lys Val Ser Thr Ser Val Ser Gln Ala Glu Val Gly
145                 150                 155                 160

Asn Gly Phe Pro Pro Ser Ala Gly Thr Phe Ser Ala Ser Asp Met Gly
                165                 170                 175

Pro Ile Gly Gln Tyr Leu Gly Ser Thr Gly Gly Pro Leu Leu Ala Asn
                180                 185                 190

Val Tyr Pro Tyr Phe Ala Tyr Val Ala Thr Arg Ala Gln Ile Asp Ile
            195                 200                 205

Asn Tyr Ala Leu Phe Thr Ser Pro Gly Thr Val Val Gln Asp Gly Gly
    210                 215                 220

Asn Ala Tyr Gln Asn Leu Phe Asp Ala Ile Val Asp Thr Phe Tyr Ser
225                 230                 235                 240

Ala Leu Glu Ser Ala Gly Ala Gly Ser Val Pro Ile Val Val Ser Glu
                245                 250                 255

Ser Gly Trp Pro Ser Ala Gly Gly Thr Ala Ala Ser Ala Gly Asn Ala
                260                 265                 270

Gln Thr Tyr Asn Gln Asn Leu Ile Asn His Val Gly Gln Gly Thr Pro
            275                 280                 285

Lys Arg Pro Gly Ser Ile Glu Thr Tyr Ile Phe Ala Met Phe Asn Glu
    290                 295                 300

Asn Gln Lys Gly Gly Asp Glu Thr Gly Arg His Phe Gly Leu Phe Asn
305                 310                 315                 320

Pro Asp Gln Ser Pro Ala Tyr Ser Ile Asn Phe
                325                 330

(2) INFORMATION FOR SEQ ID NO:57:

(i) SEQUENCE CHARACTERISTICS:
        (A) LENGTH: 996 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...996
        (D) OTHER INFORMATION:

(xi) SEQUENCE DESCRIPTION: SEQ ID NO:57:

ATG ACT ACG CAA GGA TTT GCT CCC GTG CTT GCA GTA GCA TTG CTC CTT         48
Met Thr Thr Gln Gly Phe Ala Pro Val Leu Ala Val Ala Leu Leu Leu
 1               5                  10                  15

GCA GCA TTT CCT GCA GCG GTT CAG TCC ATT GGC GTG TGC TAC GGC GTG         96
Ala Ala Phe Pro Ala Ala Val Gln Ser Ile Gly Val Cys Tyr Gly Val
            20                  25                  30

ATC GGC AAC AAC CTG CCG GCG GCG AGC GAC GTC GTG AAG CTC TAC AAG        144
Ile Gly Asn Asn Leu Pro Ala Ala Ser Asp Val Val Lys Leu Tyr Lys
        35                  40                  45

TCC AAG GGG ATC GAC TCC ATG CGC ATC TAC TTC CCG AGG AGC GAC ATC        192
Ser Lys Gly Ile Asp Ser Met Arg Ile Tyr Phe Pro Arg Ser Asp Ile
    50                  55                  60

CTC CAG GCA CTC ACC GGC TCG AAC ATC GCC CTC ACC ATG GAC GTC GCC        240
Leu Gln Ala Leu Thr Gly Ser Asn Ile Ala Leu Thr Met Asp Val Ala
65                  70                  75                  80

AAC GAG AAC CTC GCC GGT TCG CCG CCG ACG CCA CCG GCC GCG GTC GGC        288
Asn Glu Asn Leu Ala Gly Ser Pro Pro Thr Pro Pro Ala Ala Val Gly
                85                  90                  95
```

```
TGG GTC AAG CAG AAC GTC CAG GCC TAC CCG GGC GTC TCC TTC CGC TAC      336
Trp Val Lys Gln Asn Val Gln Ala Tyr Pro Gly Val Ser Phe Arg Tyr
            100                 105                 110

ATC GCC GTC GGC AAC GAG GTC ACC GGC GAC GAC ACG GGC AAC ATC CTC      384
Ile Ala Val Gly Asn Glu Val Thr Gly Asp Asp Thr Gly Asn Ile Leu
        115                 120                 125

CCG GCC ATG AAG AAC CTC AAC GCC GCG CTC GGC GCG GCC GGC CTC GGC      432
Pro Ala Met Lys Asn Leu Asn Ala Ala Leu Gly Ala Ala Gly Leu Gly
    130                 135                 140

GGC GTC GGG GTG TCG ACG TCG GTG TCC CAG GGC GTG ATC GCC AAC TCC      480
Gly Val Gly Val Ser Thr Ser Val Ser Gln Gly Val Ile Ala Asn Ser
145                 150                 155                 160

TAC CCG CCT TCC AAC GGC GTC TTC AAC GAC GAC TAC ATG TTT GAC ATC      528
Tyr Pro Pro Ser Asn Gly Val Phe Asn Asp Asp Tyr Met Phe Asp Ile
                165                 170                 175

GTG GAG TAC CTG GCG AGC ACC GGA GCG CCG CTG CTG GTT AAC GTG TAC      576
Val Glu Tyr Leu Ala Ser Thr Gly Ala Pro Leu Leu Val Asn Val Tyr
            180                 185                 190

CCC TAC TTC GCC TAC GTC GGC GAC ACG AAA GAC ATC AGC CTC AAC TAC      624
Pro Tyr Phe Ala Tyr Val Gly Asp Thr Lys Asp Ile Ser Leu Asn Tyr
        195                 200                 205

GCC ACG TTC CAG CCG GGC ACG ACG GTG ACG GAC GAC GGC AGC GGG CTG      672
Ala Thr Phe Gln Pro Gly Thr Thr Val Thr Asp Asp Gly Ser Gly Leu
    210                 215                 220

ATC TAC ACG AGC CTC TTC GAC GCG ATG GTG GAT TCC GTC TAC GCC GCG      720
Ile Tyr Thr Ser Leu Phe Asp Ala Met Val Asp Ser Val Tyr Ala Ala
225                 230                 235                 240

CTG GAG GAC GCC GGC GCG CCG GAC GTC GGC GTG GTG GTG TCG GAG ACC      768
Leu Glu Asp Ala Gly Ala Pro Asp Val Gly Val Val Val Ser Glu Thr
                245                 250                 255

GGG TGG CCG TCG GCC GGT GGG TTC GGG GCC AGC GTG AGC AAC GCG CAG      816
Gly Trp Pro Ser Ala Gly Gly Phe Gly Ala Ser Val Ser Asn Ala Gln
            260                 265                 270

ACG TAC AAC CAG AAG CTT ATC AGC CAT GTC CAA GGA GGC ACT CCG AAG      864
Thr Tyr Asn Gln Lys Leu Ile Ser His Val Gln Gly Gly Thr Pro Lys
        275                 280                 285

AGA CCA GGG GTG GCG TTG GAG ACG TAC GTG TTC GCC ATG TTC AAC GAG      912
Arg Pro Gly Val Ala Leu Glu Thr Tyr Val Phe Ala Met Phe Asn Glu
    290                 295                 300

AAC CAG AAG ACC GGG GCT GAG ACC GAG AGG CAC TTC GGG CTG TTC AAC      960
Asn Gln Lys Thr Gly Ala Glu Thr Glu Arg His Phe Gly Leu Phe Asn
305                 310                 315                 320

CCC AAC AAG TCG CCG TCC TAC AAA ATT AGA TTC CAC                      996
Pro Asn Lys Ser Pro Ser Tyr Lys Ile Arg Phe His
                325                 330
```

(2) INFORMATION FOR SEQ ID NO:58:

(i) SEQUENCE CHARACTERISTICS:
        (A) LENGTH: 332 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:58:

```
Met Thr Thr Gln Gly Phe Ala Pro Val Leu Ala Val Ala Leu Leu Leu
1               5                   10                  15
```

```
Ala Ala Phe Pro Ala Ala Val Gln Ser Ile Gly Val Cys Tyr Gly Val
                20                  25                  30

Ile Gly Asn Asn Leu Pro Ala Ala Ser Asp Val Val Lys Leu Tyr Lys
                35                  40                  45

Ser Lys Gly Ile Asp Ser Met Arg Ile Tyr Phe Pro Arg Ser Asp Ile
 50                  55                  60

Leu Gln Ala Leu Thr Gly Ser Asn Ile Ala Leu Thr Met Asp Val Ala
 65                  70                  75                  80

Asn Glu Asn Leu Ala Gly Ser Pro Pro Thr Pro Pro Ala Ala Val Gly
                85                  90                  95

Trp Val Lys Gln Asn Val Gln Ala Tyr Pro Gly Val Ser Phe Arg Tyr
                100                 105                 110

Ile Ala Val Gly Asn Glu Val Thr Gly Asp Asp Thr Gly Asn Ile Leu
                115                 120                 125

Pro Ala Met Lys Asn Leu Asn Ala Ala Leu Gly Ala Ala Gly Leu Gly
                130                 135                 140

Gly Val Gly Val Ser Thr Ser Val Ser Gln Gly Val Ile Ala Asn Ser
145                 150                 155                 160

Tyr Pro Pro Ser Asn Gly Val Phe Asn Asp Asp Tyr Met Phe Asp Ile
                165                 170                 175

Val Glu Tyr Leu Ala Ser Thr Gly Ala Pro Leu Leu Val Asn Val Tyr
                180                 185                 190

Pro Tyr Phe Ala Tyr Val Gly Asp Thr Lys Asp Ile Ser Leu Asn Tyr
                195                 200                 205

Ala Thr Phe Gln Pro Gly Thr Thr Val Thr Asp Asp Gly Ser Gly Leu
                210                 215                 220

Ile Tyr Thr Ser Leu Phe Asp Ala Met Val Asp Ser Val Tyr Ala Ala
225                 230                 235                 240

Leu Glu Asp Ala Gly Ala Pro Asp Val Gly Val Val Ser Glu Thr
                245                 250                 255

Gly Trp Pro Ser Ala Gly Gly Phe Gly Ala Ser Val Ser Asn Ala Gln
                260                 265                 270

Thr Tyr Asn Gln Lys Leu Ile Ser His Val Gln Gly Gly Thr Pro Lys
                275                 280                 285

Arg Pro Gly Val Ala Leu Glu Thr Tyr Val Phe Ala Met Phe Asn Glu
                290                 295                 300

Asn Gln Lys Thr Gly Ala Glu Thr Glu Arg His Phe Gly Leu Phe Asn
305                 310                 315                 320

Pro Asn Lys Ser Pro Ser Tyr Lys Ile Arg Phe His
                325                 330
```

(2) INFORMATION FOR SEQ ID NO:59:

(i) SEQUENCE CHARACTERISTICS:
        (A) LENGTH: 1008 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...1008
        (D) OTHER INFORMATION:

(xi) SEQUENCE DESCRIPTION: SEQ ID NO:59:

```
ATG GAT GCT GTG TTG GTT ACC GCC GCC ATC TTC GGG TTG CTC CTC TGC     48
Met Asp Ala Val Leu Val Thr Ala Ala Ile Phe Gly Leu Leu Leu Cys
 1               5                  10                  15
```

```
GGC TGC TCG GTT TCA GGA GTG GAA GGT ATC GGT GTG AAC TAT GGC ATG      96
Gly Cys Ser Val Ser Gly Val Glu Gly Ile Gly Val Asn Tyr Gly Met
            20                  25                  30

ATC GGC AAC AAC CTC CCG TCG CCG GAC AAG GTC ATC GCC CTG TAC AGA     144
Ile Gly Asn Asn Leu Pro Ser Pro Asp Lys Val Ile Ala Leu Tyr Arg
            35                  40                  45

GCC AGC AAC ATC ACC GAC ATC CGC CTC TTC CAC CCG GAC ACC ACC GTG     192
Ala Ser Asn Ile Thr Asp Ile Arg Leu Phe His Pro Asp Thr Thr Val
        50                  55                  60

CTC GCC GCG CTC CGC GGC TCG GGC CTC GGC GTC GTG CTC GGC ACG CTC     240
Leu Ala Ala Leu Arg Gly Ser Gly Leu Gly Val Val Leu Gly Thr Leu
65                  70                  75                  80

AAC GAG GAC CTG GCA CGC CTC GCC ACC GAC GCC TCG TTC GCG GCG TCG     288
Asn Glu Asp Leu Ala Arg Leu Ala Thr Asp Ala Ser Phe Ala Ala Ser
                85                  90                  95

TGG GTC CAG TCG TAC GTG CAG CCC TTC GCC GGC GCC GTC CGC TTC CGC     336
Trp Val Gln Ser Tyr Val Gln Pro Phe Ala Gly Ala Val Arg Phe Arg
                100                 105                 110

TAC ATC AAC GCC GGC AAC GAG GTC ATC CCT GGG GAC GAG GCG GCG AGC     384
Tyr Ile Asn Ala Gly Asn Glu Val Ile Pro Gly Asp Glu Ala Ala Ser
            115                 120                 125

GTC CTC CCG GCC ATG AGG AAC CTC CAG TCG CTG CGG CCC GCG GGG CTC     432
Val Leu Pro Ala Met Arg Asn Leu Gln Ser Leu Arg Pro Ala Gly Leu
    130                 135                 140

GGC GTG CCG GTC ACG ACG GTC GTC GCG ACG TCG GTG CTG GGC TCC TCG     480
Gly Val Pro Val Thr Thr Val Val Ala Thr Ser Val Leu Gly Ser Ser
145                 150                 155                 160

TAC CCG CCG TCG CAG GGC GCG TTC TCC GAG GCC GCG CTG CCG ACG GTG     528
Tyr Pro Pro Ser Gln Gly Ala Phe Ser Glu Ala Ala Leu Pro Thr Val
                165                 170                 175

GCG CCG ATC GTC TCC TTC CTG GCG TCG AGC GGG ACG CCC CTG CTG GTG     576
Ala Pro Ile Val Ser Phe Leu Ala Ser Ser Gly Thr Pro Leu Leu Val
            180                 185                 190

AAC GTG TAC CCG TAC TTC GCC TAC TCG GCC GAC CCG TCG TCG GTG CGG     624
Asn Val Tyr Pro Tyr Phe Ala Tyr Ser Ala Asp Pro Ser Ser Val Arg
        195                 200                 205

CTC GAC TAC GCG CTG CTG CTG CCG TCG ACG TCG GCG GCC GTG ACG GAC     672
Leu Asp Tyr Ala Leu Leu Leu Pro Ser Thr Ser Ala Ala Val Thr Asp
210                 215                 220

GGC GGT GTC ACG TAC ACC AAC ATG TTC GAC GCC ATC CTG GAC GCG GTG     720
Gly Gly Val Thr Tyr Thr Asn Met Phe Asp Ala Ile Leu Asp Ala Val
225                 230                 235                 240

TAC GCG GCG CTG GAG AAG GCG GGC GGG CAG GGC CTG GAG GTG GTG GTG     768
Tyr Ala Ala Leu Glu Lys Ala Gly Gly Gln Gly Leu Glu Val Val Val
                245                 250                 255

TCG GAG ACC GGG TGG CCG TCG GGC GGC GGC GGG GCC GGC GCC AGC GTG     816
Ser Glu Thr Gly Trp Pro Ser Gly Gly Gly Gly Ala Gly Ala Ser Val
                260                 265                 270

GAG AAC GCG GCG GCG TAC AGC AAC AAC CTG GTG CGC CAC GTC GGG CGC     864
Glu Asn Ala Ala Ala Tyr Ser Asn Asn Leu Val Arg His Val Gly Arg
            275                 280                 285

GGC ACG CCG CGG CGG CCC GGG AAG GCC GTG GAG ACG TAC ATC TTC GCC     912
Gly Thr Pro Arg Arg Pro Gly Lys Ala Val Glu Thr Tyr Ile Phe Ala
        290                 295                 300

ATG TTC AAC GAG AAC CAG AAG CCC CGA GGC GTG GAG AGA AAC TTC GGC     960
Met Phe Asn Glu Asn Gln Lys Pro Arg Gly Val Glu Arg Asn Phe Gly
305                 310                 315                 320

CTG TTC CAC CCG GAC ATG AGC GCG GTC TAC CAC GTC GAC TTC TCG GCG    1008
Leu Phe His Pro Asp Met Ser Ala Val Tyr His Val Asp Phe Ser Ala
```

325 330 335

(2) INFORMATION FOR SEQ ID NO:60:

(i) SEQUENCE CHARACTERISTICS:
      (A) LENGTH: 336 amino acids
      (B) TYPE: amino acid
      (C) STRANDEDNESS: single
      (D) TOPOLOGY: linear (ii) MOLECULE TYPE: protein (v) FRAGMENT TYPE: internal (xi) SEQUENCE DESCRIPTION: SEQ ID NO:60:

```
Met Asp Ala Val Leu Val Thr Ala Ala Ile Phe Gly Leu Leu Leu Cys
  1               5                  10                  15

Gly Cys Ser Val Ser Gly Val Glu Gly Ile Gly Val Asn Tyr Gly Met
                 20                  25                  30

Ile Gly Asn Asn Leu Pro Ser Pro Asp Lys Val Ile Ala Leu Tyr Arg
             35                  40                  45

Ala Ser Asn Ile Thr Asp Ile Arg Leu Phe His Pro Asp Thr Thr Val
 50                  55                  60

Leu Ala Leu Arg Gly Ser Gly Leu Gly Val Val Leu Gly Thr Leu
 65                  70                  75                  80

Asn Glu Asp Leu Ala Arg Leu Ala Thr Asp Ala Ser Phe Ala Ala Ser
                 85                  90                  95

Trp Val Gln Ser Tyr Val Gln Pro Phe Ala Gly Ala Val Arg Phe Arg
                100                 105                 110

Tyr Ile Asn Ala Gly Asn Glu Val Ile Pro Gly Asp Glu Ala Ala Ser
            115                 120                 125

Val Leu Pro Ala Met Arg Asn Leu Gln Ser Leu Arg Pro Ala Gly Leu
130                 135                 140

Gly Val Pro Val Thr Thr Val Val Ala Thr Ser Val Leu Gly Ser Ser
145                 150                 155                 160

Tyr Pro Pro Ser Gln Gly Ala Phe Ser Glu Ala Ala Leu Pro Thr Val
                165                 170                 175

Ala Pro Ile Val Ser Phe Leu Ala Ser Ser Gly Thr Pro Leu Leu Val
            180                 185                 190

Asn Val Tyr Pro Tyr Phe Ala Tyr Ser Ala Asp Pro Ser Ser Val Arg
                195                 200                 205

Leu Asp Tyr Ala Leu Leu Pro Ser Thr Ser Ala Ala Val Thr Asp
    210                 215                 220

Gly Gly Val Thr Tyr Thr Asn Met Phe Asp Ala Ile Leu Asp Ala Val
225                 230                 235                 240

Tyr Ala Ala Leu Glu Lys Ala Gly Gly Gln Gly Leu Glu Val Val Val
                245                 250                 255

Ser Glu Thr Gly Trp Pro Ser Gly Gly Gly Ala Gly Ala Ser Val
                260                 265                 270

Glu Asn Ala Ala Ala Tyr Ser Asn Asn Leu Val Arg His Val Gly Arg
            275                 280                 285

Gly Thr Pro Arg Arg Pro Gly Lys Ala Val Glu Thr Tyr Ile Phe Ala
290                 295                 300

Met Phe Asn Glu Asn Gln Lys Pro Arg Gly Val Glu Arg Asn Phe Gly
305                 310                 315                 320

Leu Phe His Pro Asp Met Ser Ala Val Tyr His Val Asp Phe Ser Ala
                325                 330                 335
```

(2) INFORMATION FOR SEQ ID NO:61:

(i) SEQUENCE CHARACTERISTICS:
        (A) LENGTH: 1020 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...1020
        (D) OTHER INFORMATION:

(xi) SEQUENCE DESCRIPTION: SEQ ID NO:61:

```
ATG TTA CAT CTC AAC CAA AAT ATA TAT CTT ATT CTG CCA ATA GTT TTT      48
Met Leu His Leu Asn Gln Asn Ile Tyr Leu Ile Leu Pro Ile Val Phe
 1               5                  10                  15

CTG ATT GAC GAA ATG AAA AAG GCT GAA GGC GCC ATT GGT GTG AAC TAC      96
Leu Ile Asp Glu Met Lys Lys Ala Glu Gly Ala Ile Gly Val Asn Tyr
                20                  25                  30

GGC ATG CTG GGG AAC AAC CTG CCG TCG CCG GCG CAG GTG ATC TCC ATG     144
Gly Met Leu Gly Asn Asn Leu Pro Ser Pro Ala Gln Val Ile Ser Met
            35                  40                  45

TAC AAG GCC AAG AAC ATC AAC TAC GTC CGC CTC TTC CAC CCG GAC ACC     192
Tyr Lys Ala Lys Asn Ile Asn Tyr Val Arg Leu Phe His Pro Asp Thr
        50                  55                  60

GCC GTC CTC GCC GCG CTC CGC AAC TCC GGC ATC GGC GTC GTC CTC GGC     240
Ala Val Leu Ala Ala Leu Arg Asn Ser Gly Ile Gly Val Val Leu Gly
65                  70                  75                  80

ACG TAC AAC GAG GAC CTC GCC CGC CTC GCC TCC GAC TCC TCG TTT GCC     288
Thr Tyr Asn Glu Asp Leu Ala Arg Leu Ala Ser Asp Ser Ser Phe Ala
                85                  90                  95

GCC TCC TGG GTC AGC TCC TAC GTC CAG CCC TTC GCC GGC GCC GTC ACG     336
Ala Ser Trp Val Ser Ser Tyr Val Gln Pro Phe Ala Gly Ala Val Thr
            100                 105                 110

TTC CGC TAC ATC AAC GCC GGC AAC GAG GTC ATC CCC GGC GAC CCC GCC     384
Phe Arg Tyr Ile Asn Ala Gly Asn Glu Val Ile Pro Gly Asp Pro Ala
        115                 120                 125

GCC AAC GTC CTC CCG GCC ATG CGC AAC CTC GAC GCC GCG CTC AAG GCC     432
Ala Asn Val Leu Pro Ala Met Arg Asn Leu Asp Ala Ala Leu Lys Ala
    130                 135                 140

GCC GGG ATC AGC GGC ATC CCG GTC ACC ACC GCC GTC GCC ACG TCC GTG     480
Ala Gly Ile Ser Gly Ile Pro Val Thr Thr Ala Val Ala Thr Ser Val
145                 150                 155                 160

CTC GGC GTC TCG TAC CCG CCG TCG CAG GGC GCG TTC TCG GAG GGC GCG     528
Leu Gly Val Ser Tyr Pro Pro Ser Gln Gly Ala Phe Ser Glu Gly Ala
                165                 170                 175

TCG CCG TAC ACT GCG CCG ATC GTC GCC TAC CTC GCG TCC AGG GGC GCG     576
Ser Pro Tyr Thr Ala Pro Ile Val Ala Tyr Leu Ala Ser Arg Gly Ala
            180                 185                 190

CCG CTG CTG GTG AAC GTG TAC CCC TAC TTT GCG TAC GGC GCG GAC CCG     624
Pro Leu Leu Val Asn Val Tyr Pro Tyr Phe Ala Tyr Gly Ala Asp Pro
        195                 200                 205

AGC AGC GTG CAG CTC GGG TAC GCG CTG CTG TCG GGG TCG CAG TCG GCG     672
Ser Ser Val Gln Leu Gly Tyr Ala Leu Leu Ser Gly Ser Gln Ser Ala
    210                 215                 220

TCG GTG ACC GAC GGC GGC GTG ACA TAC ACC AAC ATG TTC GAC GCG ATC     720
Ser Val Thr Asp Gly Gly Val Thr Tyr Thr Asn Met Phe Asp Ala Ile
225                 230                 235                 240

GTG GAC GCG GGC TAC GCG GCG GTG GAG AAG GCG ACG GGC GGG CAG GCG     768
Val Asp Ala Gly Tyr Ala Ala Val Glu Lys Ala Thr Gly Gly Gln Ala
```

-continued

```
                        245                 250                 255
GTG GAG CTG GTG GTG TCG GAG ACC GGC TGG CCG TCC GGT GGC GGC GGC       816
Val Glu Leu Val Val Ser Glu Thr Gly Trp Pro Ser Gly Gly Gly Gly
            260                 265                 270

GTG GGC GCC ACC GTG GAG AAC GCG GCG GCG TAC AAC AAC AAC CTG ATC       864
Val Gly Ala Thr Val Glu Asn Ala Ala Ala Tyr Asn Asn Asn Leu Ile
            275                 280                 285

CGC CAC GTC TCC GGC GGC GCC GGG ACG CCG CGG CGG CCG GGG AAG CCG       912
Arg His Val Ser Gly Gly Ala Gly Thr Pro Arg Arg Pro Gly Lys Pro
            290                 295                 300

GTG GAG ACG TAC CTG TTC GCC ATG TTC AAC GAG AAC CAG AAG CCC GAG       960
Val Glu Thr Tyr Leu Phe Ala Met Phe Asn Glu Asn Gln Lys Pro Glu
305                 310                 315                 320

GGC GTG GAG CAG CAT TTC GGC CTC TTC CAG CCC GAC ATG ACC GAA GTC      1008
Gly Val Glu Gln His Phe Gly Leu Phe Gln Pro Asp Met Thr Glu Val
                325                 330                 335

TAC CAT GTC GAC                                                       1020
Tyr His Val Asp
            340
```

(2) INFORMATION FOR SEQ ID NO:62:

(i) SEQUENCE CHARACTERISTICS:
        (A) LENGTH: 340 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:62:

```
Met Leu His Leu Asn Gln Asn Ile Tyr Leu Ile Leu Pro Ile Val Phe
1               5                   10                  15

Leu Ile Asp Glu Met Lys Lys Ala Glu Gly Ala Ile Gly Val Asn Tyr
            20                  25                  30

Gly Met Leu Gly Asn Asn Leu Pro Ser Pro Ala Gln Val Ile Ser Met
        35                  40                  45

Tyr Lys Ala Lys Asn Ile Asn Tyr Val Arg Leu Phe His Pro Asp Thr
50                  55                  60

Ala Val Leu Ala Ala Leu Arg Asn Ser Gly Ile Gly Val Val Leu Gly
65                  70                  75                  80

Thr Tyr Asn Glu Asp Leu Ala Arg Leu Ala Ser Asp Ser Ser Phe Ala
            85                  90                  95

Ala Ser Trp Val Ser Ser Tyr Val Gln Pro Phe Ala Gly Ala Val Thr
        100                 105                 110

Phe Arg Tyr Ile Asn Ala Gly Asn Glu Val Ile Pro Gly Asp Pro Ala
    115                 120                 125

Ala Asn Val Leu Pro Ala Met Arg Asn Leu Asp Ala Ala Leu Lys Ala
130                 135                 140

Ala Gly Ile Ser Gly Ile Pro Val Thr Thr Ala Val Ala Thr Ser Val
145                 150                 155                 160

Leu Gly Val Ser Tyr Pro Pro Ser Gln Gly Ala Phe Ser Glu Gly Ala
            165                 170                 175

Ser Pro Tyr Thr Ala Pro Ile Val Ala Tyr Leu Ala Ser Arg Gly Ala
        180                 185                 190

Pro Leu Leu Val Asn Val Tyr Pro Tyr Phe Ala Tyr Gly Ala Asp Pro
    195                 200                 205
```

-continued

```
Ser Ser Val Gln Leu Gly Tyr Ala Leu Leu Ser Gly Ser Gln Ser Ala
    210                 215                 220
Ser Val Thr Asp Gly Gly Val Thr Tyr Thr Asn Met Phe Asp Ala Ile
225                 230                 235                 240
Val Asp Ala Gly Tyr Ala Ala Val Glu Lys Ala Thr Gly Gly Gln Ala
                245                 250                 255
Val Glu Leu Val Val Ser Glu Thr Gly Trp Pro Ser Gly Gly Gly Gly
                260                 265                 270
Val Gly Ala Thr Val Glu Asn Ala Ala Ala Tyr Asn Asn Asn Leu Ile
                275                 280                 285
Arg His Val Ser Gly Gly Ala Gly Thr Pro Arg Arg Pro Gly Lys Pro
            290                 295                 300
Val Glu Thr Tyr Leu Phe Ala Met Phe Asn Glu Asn Gln Lys Pro Glu
305                 310                 315                 320
Gly Val Glu Gln His Phe Gly Leu Phe Gln Pro Asp Met Thr Glu Val
                325                 330                 335
Tyr His Val Asp
            340
```

(2) INFORMATION FOR SEQ ID NO:63:

(i) SEQUENCE CHARACTERISTICS:
        (A) LENGTH: 1131 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...1131
        (D) OTHER INFORMATION:

(xi) SEQUENCE DESCRIPTION: SEQ ID NO:63:

```
ATG GCT CTA CCC GGG GGC CTC CGC GCC CTC ATC CTC GCC GTT GCA TTG        48
Met Ala Leu Pro Gly Gly Leu Arg Ala Leu Ile Leu Ala Val Ala Leu
 1               5                  10                  15

CCG CTG CTC TTC CTG TCC GCT TCA GAG GCG GGC ACG GTG GGG ATC AAC        96
Pro Leu Leu Phe Leu Ser Ala Ser Glu Ala Gly Thr Val Gly Ile Asn
                20                  25                  30

TAT GGG AGG GTG GCG AAC GAC CTG CCC AAC CCG GCG GCG GTG GTG CAG       144
Tyr Gly Arg Val Ala Asn Asp Leu Pro Asn Pro Ala Ala Val Val Gln
            35                  40                  45

CTG ATG AAG CAG CAG GGC ATC GCG CAG GTG AAG CTG TAC GAC ACC GAG       192
Leu Met Lys Gln Gln Gly Ile Ala Gln Val Lys Leu Tyr Asp Thr Glu
         50                  55                  60

CCG ACC GTG CTG CGG GCG CTG GCC AAC ACC GGC ATC AAG GTG GTG GTC       240
Pro Thr Val Leu Arg Ala Leu Ala Asn Thr Gly Ile Lys Val Val Val
 65                  70                  75                  80

GCG CTG CCC AAC GAG CAG CTG CTC GCC GCG GCG TCG CGC CCG TCG TAC       288
Ala Leu Pro Asn Glu Gln Leu Leu Ala Ala Ala Ser Arg Pro Ser Tyr
                 85                  90                  95

GCG CTC GCC TGG GTG CGC CGC AAC GTC GCA GCG TAC TAC CCG GCC ACG       336
Ala Leu Ala Trp Val Arg Arg Asn Val Ala Ala Tyr Tyr Pro Ala Thr
                100                 105                 110

CAG ATC CAG GGC ATC GCC GTC GGG AAC GAG GTG TTC GCC TCG GCC AAG       384
Gln Ile Gln Gly Ile Ala Val Gly Asn Glu Val Phe Ala Ser Ala Lys
            115                 120                 125

AAC CTC ACG GCG CAG CTC GTC CCG GCG ATG ACC AAC GTG CAC GCC GCG       432
Asn Leu Thr Ala Gln Leu Val Pro Ala Met Thr Asn Val His Ala Ala
        130                 135                 140
```

```
CTG GCG AGG CTC AGC CTT GAC AAG CCC GTC AAG GTG TCG TCC CCC ATC      480
Leu Ala Arg Leu Ser Leu Asp Lys Pro Val Lys Val Ser Ser Pro Ile
145                 150                 155                 160

GCG CTC ACC GCG CTC GCC GGC TCG TAC CCG CCG TCG GCC GGC GTG TTC      528
Ala Leu Thr Ala Leu Ala Gly Ser Tyr Pro Pro Ser Ala Gly Val Phe
                165                 170                 175

CGG GAG GAC CTC GCC CAG GCG GTC ATG AAG CCC ATG CTC GAC TTC CTC      576
Arg Glu Asp Leu Ala Gln Ala Val Met Lys Pro Met Leu Asp Phe Leu
            180                 185                 190

GCG CAG ACC GGC TCG TAC CTC ATG GTG AAC GCG TAC CCG TTC TTC GCG      624
Ala Gln Thr Gly Ser Tyr Leu Met Val Asn Ala Tyr Pro Phe Phe Ala
        195                 200                 205

TAC TCT GGC AAT ACT GAC GTC ATC TCC CTC GAC TAC GCG CTG TTC CGC      672
Tyr Ser Gly Asn Thr Asp Val Ile Ser Leu Asp Tyr Ala Leu Phe Arg
    210                 215                 220

CCC AAC GCC GGC GTG CTC GAC TCC GGG AGC GGC CTC AAG TAC TAC AGC      720
Pro Asn Ala Gly Val Leu Asp Ser Gly Ser Gly Leu Lys Tyr Tyr Ser
225                 230                 235                 240

CTC CTC GAC GCC CAG CTC GAC GCC GTG TTC ACC GCG GTG AGC AAG CTT      768
Leu Leu Asp Ala Gln Leu Asp Ala Val Phe Thr Ala Val Ser Lys Leu
                245                 250                 255

GGG AAC TAC AAT GCC GTG CGC GTC GTG GTG TCG GAG ACC GGG TGG CCG      816
Gly Asn Tyr Asn Ala Val Arg Val Val Val Ser Glu Thr Gly Trp Pro
            260                 265                 270

TCC AAG GGT GAC GCC AAG GAG ACC GGC GCC GCG GCG GCC AAC GCC GCG      864
Ser Lys Gly Asp Ala Lys Glu Thr Gly Ala Ala Ala Ala Asn Ala Ala
        275                 280                 285

GCC TAC AAC GGC AAC CTG GTG CGC CGC GTC CTC TCC GGC AAC GCC AGA      912
Ala Tyr Asn Gly Asn Leu Val Arg Arg Val Leu Ser Gly Asn Ala Arg
    290                 295                 300

ACG CCG CGC CGC CCC GAC GCC GAC ATG GAC GTG TAC CTC TTC GCT CTC      960
Thr Pro Arg Arg Pro Asp Ala Asp Met Asp Val Tyr Leu Phe Ala Leu
305                 310                 315                 320

TTC AAC GAG AAC CAG AAA CCC GGA CCG ACC TCC GAG CGC AAC TAC GGC     1008
Phe Asn Glu Asn Gln Lys Pro Gly Pro Thr Ser Glu Arg Asn Tyr Gly
                325                 330                 335

GTG TTC TAC CCG AAC CAG CAG AAG GTC TAC GAC GTC GAG TTC GTC CTC     1056
Val Phe Tyr Pro Asn Gln Gln Lys Val Tyr Asp Val Glu Phe Val Leu
            340                 345                 350

GGC GGC AAC TCG CTG GCG GCG GCG GCA GCA GCG GCA AGG ACA ACG GCG     1104
Gly Gly Asn Ser Leu Ala Ala Ala Ala Ala Ala Arg Thr Thr Ala
        355                 360                 365

GGC TCG GCT GGC AGG ACA ACG GCG GGG                                 1131
Gly Ser Ala Gly Arg Thr Thr Ala Gly
    370                 375
```

(2) INFORMATION FOR SEQ ID NO:64:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:64:

```
Met Ala Leu Pro Gly Gly Leu Arg Ala Leu Ile Leu Ala Val Ala Leu
1               5                   10                  15
```

```
Pro Leu Leu Phe Leu Ser Ala Ser Glu Ala Gly Thr Val Gly Ile Asn
            20                  25                  30

Tyr Gly Arg Val Ala Asn Asp Leu Pro Asn Pro Ala Ala Val Val Gln
            35                  40                  45

Leu Met Lys Gln Gln Gly Ile Ala Gln Val Lys Leu Tyr Asp Thr Glu
 50                  55                  60

Pro Thr Val Leu Arg Ala Leu Ala Asn Thr Gly Ile Lys Val Val Val
 65                  70                  75                  80

Ala Leu Pro Asn Glu Gln Leu Leu Ala Ala Ser Arg Pro Ser Tyr
                85                  90                  95

Ala Leu Ala Trp Val Arg Arg Asn Val Ala Ala Tyr Tyr Pro Ala Thr
                100                 105                 110

Gln Ile Gln Gly Ile Ala Val Gly Asn Glu Val Phe Ala Ser Ala Lys
            115                 120                 125

Asn Leu Thr Ala Gln Leu Val Pro Ala Met Thr Asn Val His Ala Ala
            130                 135                 140

Leu Ala Arg Leu Ser Leu Asp Lys Pro Val Lys Val Ser Ser Pro Ile
145                 150                 155                 160

Ala Leu Thr Ala Leu Ala Gly Ser Tyr Pro Pro Ser Ala Gly Val Phe
                165                 170                 175

Arg Glu Asp Leu Ala Gln Ala Val Met Lys Pro Met Leu Asp Phe Leu
            180                 185                 190

Ala Gln Thr Gly Ser Tyr Leu Met Val Asn Ala Tyr Pro Phe Phe Ala
            195                 200                 205

Tyr Ser Gly Asn Thr Asp Val Ile Ser Leu Asp Tyr Ala Leu Phe Arg
        210                 215                 220

Pro Asn Ala Gly Val Leu Asp Ser Gly Ser Gly Leu Lys Tyr Tyr Ser
225                 230                 235                 240

Leu Leu Asp Ala Gln Leu Asp Ala Val Phe Thr Ala Val Ser Lys Leu
                245                 250                 255

Gly Asn Tyr Asn Ala Val Arg Val Val Val Ser Glu Thr Gly Trp Pro
            260                 265                 270

Ser Lys Gly Asp Ala Lys Glu Thr Gly Ala Ala Ala Asn Ala Ala
        275                 280                 285

Ala Tyr Asn Gly Asn Leu Val Arg Arg Val Leu Ser Gly Asn Ala Arg
 290                 295                 300

Thr Pro Arg Arg Pro Asp Ala Asp Met Asp Val Tyr Leu Phe Ala Leu
305                 310                 315                 320

Phe Asn Glu Asn Gln Lys Pro Gly Pro Thr Ser Glu Arg Asn Tyr Gly
                325                 330                 335

Val Phe Tyr Pro Asn Gln Gln Lys Val Tyr Asp Val Glu Phe Val Leu
            340                 345                 350

Gly Gly Asn Ser Leu Ala Ala Ala Ala Ala Ala Arg Thr Thr Ala
            355                 360                 365

Gly Ser Ala Gly Arg Thr Thr Ala Gly
    370                 375

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:65:
```

-continued

```
AATTCGGCGT GTGCTACGGC ATGA                                    24

(2) INFORMATION FOR SEQ ID NO:66:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:66:

TACAAGTTGC TCTTGGTCTT CTTAA                                   25
```

RICE β-GLUCANASE ENZYMES AND GENES

This application claims the priority of U.S. Provisional application No. 60/050,675, filed Jun. 25, 1997, which is incorporated by reference herein.

FIELD OF THE INVENTION

The present invention relates to novel rice β-glucanase enzymes and genes, and their uses in improved monocot plants.

REFERENCES

Akiyama, T., et al., *Biotech. Biochem.* 60:2078–2080 (1996a).
Akiyama, T., et al., *Plant Cell Physiol.* 37:702–705 (1996b).
Akiyama, T., et al., *Carbohydr. Res.* 297: 365–374 (1997).
Alber and Kawasaki, *Mol. and Appl. Genet.* 1:419–434 (1982).
Ausubel, F. M., et al., in CURRENT PROTOCOLS IN MOLECULAR BIOLOGY, John Wiley & Sons, Media, Pa. (1992).
Benhamou, N., *Trends in Plant Science* 233–240 (1996).
Bidney, et al., *Plant Mol. Biol.* 18:301–313 (1992).
Chen, Z., et al., *Proc. Natl. Acad. Sci USA* 92:4134–4137 (1995).
Depicker, et al., *Mol. Appl. Genet.* 1:561–573 (1982).
Dellaporta, S. L., et al. *Plant Biol Report* 1: 19–21 (1983).
Evans, et al., HANDBOOK OF PLANT CELL CULTURES Vol. 1, MacMillan Publishing Co. New York, N.Y. (1983).
Fincher, G. B., et al., *Proc. Natl. Acad. Sci. USA* 83:2081–2085 (1986).
Foolad, M. R., et al., *Plant Cell Reports* 12:293–297 (1993).
Fraley, et al., *Proc. Natl. Acad. Sci. USA* 79:1859–1863 (1982).
Fromm, et al., *Pro. Natl Acad. Sci. USA* 82:5824 (1985).
Gelvin, S. B., and Schilperoot, R. A., in PLANT MOLECULAR BIOLOGY (1988).
Gielen, et al., *EMBO J.* 3:835–846 (1984).
Hagio, et al., *Plant Cell Reports* 14:329 (1995).
Herrera-Estrella, et al., *Nature* 303:209–213 (1983).
Høj, P. B., et al., *Plant Mol. Biol.* 13:31–42 (1989).
Hrmova, M., et al., *Plant Mol. Biol.* 22:347 (1993).
Huang, N., et al., *Nuc. Acids Res.* 18:7007–7014 (1990).
Hubbard, S. C., and Ivatt, R. J., *Ann. Rev. Biochem.* 50:555–583 (1981).
Jensen, L. G., et al., *Proc. Natl. Acad. Sci. USA* 93:3487–3491 (1996).
Klein, et al., *Nature* 327:70–73 (1987).
Knudsen and Muller, *Planta* 185:330–336 (1991).
Li, L., et al., *Plant Cell Reports* 12:250 (1993).
Linthorst, H., *Crit. Rev. Plant Sci.* 10:123–150 (1991).
Litts, J. C., et al., *Eur. J. Biochem.* 194:831–838 (1990).
Malehorn, D. E., et al., *Plant Mol. Biol.* 22:347–360 (1993).
Mueller, M. J., et al., *Proc. Natl. Acad. Sci. USA* 90:7490–7494 (1993).
Mullis, K. B., et al., U.S. Pat. No. 4,683,195, issued Jul. 28, 1987.
Mullis, K. B., U.S. Pat. No. 4,683,202, issued Jul. 28, 1987.
Odell, et al., *Nature* 313:810–812 (1985).
Pearson, W. R. and Lipman, D. J., *PNAS* 85:2444–2448 (1988).
Pearson, W. R., *Methods in Enzymology* 183:63–98 (1990).
Ryu, D. D. Y., et al, Eds., in ADVANCES IN PLANT BIOTECHNOLOGY, Elsevier, Amsterdam, p.37 (1994).
Sambrook, et al., in MOLECULAR CLONING—A LABORATORY MANUAL, Cold Spring Harbor Laboratory, Cold Spring Harbor, N.Y. (1989)
Sela-Buurlage, M. B., et al., *Plant Physiol.* 101:857–863 (1993).
Simmons, C. R., et al., *Plant Mol. Biol.* 18:33–45 (1992).
Simmons, C. R., *Crit. Rev. Plant Sci.* 13:325–387 (1994).
Sivamani, E. et al., *Plant Cell Reports* 15:465 (1996).
Slakeski, N., et al., *Mol. Gen. Genet.* 224:437–449 (1990).
Thompson, J. A., et al., *Plant Science* 47:123 (1986).
van der Elzer, *Plant Mol. Biol.* 5:299–302 (1985).
Varghese, J. N., et al., *Proc. Natl. Acad. Sci. USA* 91:2785–2789 (1994).
Vasil, I. R. (Ed.), CELL CULTURE AND SOMATIC CELL GENETICS OF PLANTS, Acad. Press, Orlando, Vol. I, (1984) and Vol. III (1986).
Velten, et al., *EMBO J.* 3:2723–2730 (1984).
Wan, Y., et al., *Plant Physiol.* 104:47–48 (1994).
Wang, J., et al., *Eur. J. Biochem.* 209:103–109 (1992).
Wilmink and Dons, *Plant Mol. Biol. Reptr.* 11(2):165–185 (1991).
Wolf, N., *Plant Physiol.* 96:1382–1384 (1991).
Wu, S., et al., *Plant Physiol.* 106:1709–1710 (1994).
Xu, P., et al., *Gene* 120:157–165 (1992).
Yun, S., et al., *Plant Physiol.* 103:295–296 (1993).
Zhang, S., et al., *Plant Cell Reports* 15:465 (1996).

BACKGROUND OF THE INVENTION

The endo-1,3-β-glucanase gene family encodes isozymes that catalyze the hydrolysis of 1,3-β-D-glycosidic bonds in cell wall polymers of plants and fungi. The substrates for these glucanases include 1,3-β-glucans and 1,3;1,6-β-glucans. An N-terminal signal peptide directs all glucanase isozymes into the endoplasmic reticulum. Most glucanase isozymes are then secreted into the apoplast, but C-terminal peptides direct certain glucanase isozymes into the vacuole (Simmons, 1994).

This diversity of functions is matched by a multiplicity of 1,3-β-glucanase genes and isozymes. In the more exhaustively studied plant species, the number of genes or isozymes ranges from 5 to 14 (Simmons, 1994). The first β-glucanase gene characterized in rice was Gns1;1, which was predicted to encode a 1,3;1,4-β-glucanase based on homology to the EI gene of barley (Simmons, et al., 1992). Akiyama, et al. have recently characterized a glucanase isozyme from rice which has 1,3;1,4-β-glucanase activity and an acidic pI (Akiyama, et al., 1996a, 1996b); this isozyme may be encoded by the Gns1;1 gene. Akiyama, et al. have also recently characterized two 1,3-β-glucanase isozymes from rice (Akiyama, et al., 1996a, 1996b; Akiyama, et al., 1997).

Eight genes which encode novel rice β-glucanase isozymes Gns2–9 are discosed herein. The genes, the gene promoters, and nucleic acids encoding signal peptides, full-length proteins, and mature proteins, are useful in a variety of transgenic monocot plants, for example, in achieving increased plant resistance to fungal infection, improved growth characteristics, and high levels of expression of heterologous proteins in various tissues obtained from the plants.

SUMMARY OF THE INVENTION

The invention includes, in one aspect, an isolated DNA having a sequence of nucleotides which hybridizes under conditions of high stringency with a rice β-glucanase gene having one of the sequences: SEQ ID NO:1, SEQ ID NO:2, SEQ ID NO:3, SEQ ID NO:4, SEQ ID NO:5, SEQ ID NO:6, SEQ ID NO:7, and SEQ ID NO:8, corresponding to rice β-glucanase genes 2–9 (Gns2–Gns9), respectively.

In one embodiment, the isolated DNA has a sequence with at least 80% nucleotide sequence identity to one of the rice Gns2–9 gene sequences identified as SEQ ID NO:1, SEQ ID NO:2, SEQ ID NO:3, SEQ ID NO:4, SEQ ID NO:5, SEQ ID NO:6, SEQ ID NO: 7, and SEQ ID NO: 8, or to a portion of one of these sequences as set out below. In other embodiments, the isolated DNA sequence has at least 90% sequence identity or at least 95% sequence identity to one of SEQ ID NO:1–8 or a portion thereof as described below.

The DNA may include the promoter region from one of the genes whose promoter regions are identified by SEQ ID NO:9, SEQ ID NO:10, SEQ ID NO: 11, SEQ ID NO:12, SEQ ID NO: 13, SEQ ID NO:14, SEQ ID NO:15, or SEQ ID NO:16.

Alternatively, the DNA may include the signal-peptide coding sequence from one of the genes whose signal-peptide coding regions are identified by SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

Alternatively, the DNA may include the coding sequence for one of the mature β-glucanase enzymes, whose coding regions are identified by SEQ ID NO:33, SEQ ID NO:35, SEQ ID NO:37, SEQ ID NO:39, SEQ ID NO:41, SEQ ID NO:43, SEQ ID NO:45, or SEQ ID NO:47.

In another aspect, the invention includes a chimeric gene for use in producing a transgenic monocot plant. The gene has a transcriptional regulatory region inducible during seed germination and effective to hybridize under conditions of high stringency with a rice β-glucanase gene promoter having one of the sequences SEQ ID NO:9, SEQ ID NO:10, SEQ ID NO: 11, SEQ ID NO:12, SEQ ID NO: 13, SEQ ID NO:14, SEQ ID NO:15, or SEQ ID NO:16. Also included are a first DNA sequence heterologous to the regulatory region, and encoding a protein to be produced by the plant, and a second DNA sequence encoding a signal polypeptide. The second DNA sequence is operably linked to the transcriptional regulatory region and the first DNA sequence, and the signal polypeptide is in translation-frame with the protein and is effective to facilitate secretion of the protein across aleurone or scutellar epithelium layers into the endosperm of seeds obtained from the plant.

In one general embodiment, the second DNA sequence is a β-glucanase gene signal-peptide coding sequence having one of the sequences SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

For use in producing a heterologous protein in germinating seeds obtained from the transformed plant, the transcriptional regulatory region is preferably a promoter effective to hybridize under conditions of high stringency with a rice β-glucanase gene promoter identified by SEQ ID NO:11, SEQ ID NO:13, and SEQ ID NO: 14, more preferably SEQ ID NO:11.

For use in producing a heterologous protein in root tissue of the transformed plant, the transcriptional regulatory region is preferably a promoter effective to hybridize under conditions of high stringency with a rice β-glucanase gene promoter identified by SEQ ID NO:15.

For use in producing a heterologous protein in callus tissue of the transformed plant, the transcriptional regulatory region is preferably a promoter effective to hybridize under conditions of high stringency with a rice β-glucanase gene promoter identified by SEQ ID NO:16.

For use in producing a heterologous protein in leaf tissue of the transformed plant, the transcriptional regulatory region is preferably a promoter effective to hybridize under conditions of high stringency with a rice β-glucanase gene promoter identified by SEQ ID NO:13 or SEQ ID NO:14.

In one general embodiment, the first coding sequence encodes the sequence of a mature, non-plant heterologous protein.

In another general embodiment, for producing a plant with improved fungal resistance or improved plant growth and development characteristics, the first DNA coding sequence encodes a rice β-glucanase protein having a mature protein sequence identified by SEQ ID NO:34, SEQ ID NO:36, SEQ ID NO:38, SEQ ID NO:40, SEQ ID NO:42, SEQ ID NO:44, SEQ ID NO:46, or SEQ ID NO:48, corresponding to the coding sequences of mature rice β-glucanase 2–9 enzymes, respectively. Preferably, the first DNA coding sequence encodes a rice β-glucanase protein having a mature protein sequence identified by SEQ ID NO:49.

In a related aspect, the invention includes a chimeric gene for use in producing a transgenic monocot plant. The gene has a transcriptional regulatory region inducible during seed germination, a first DNA sequence heterologous to the regulatory region, and encoding a protein to be produced by the plant, and a second DNA sequence encoding a signal polypeptide having a sequence selected from the group consisting of SEQ ID NO:18, SEQ ID NO:20, SEQ ID NO:22, SEQ ID NO:24, SEQ ID NO:26, SEQ ID NO:28, SEQ ID NO:30 and SEQ ID NO:32. The second DNA sequence is operably linked to the transcriptional regulatory region and the first DNA sequence, and the signal polypeptide is in translation-frame with the protein and is effective to facilitate secretion of the protein across aleurone or scutellar epithelium layers into the endosperm of seeds obtained from the plant.

Also disclosed is a monocot plant stably transformed with one of the above chimeric genes. In a transformed plant having enhanced resistance to fungal infection, the first DNA coding sequence encodes a rice β-glucanase protein having a mature protein sequence identified by SEQ ID NO:34, SEQ ID NO:36, SEQ ID NO:38, SEQ ID NO:40, SEQ ID NO:42, SEQ ID NO:44, SEQ ID NO:46, or SEQ ID NO:48, corresponding to the coding sequences of mature rice β-glucanase 2–9 enzymes, respectively. Where the plant is intended to have enhanced seed resistance to fungal infection, the transcriptional regulatory region is preferably effective to hybridize under conditions of high stringency with a rice β-glucanase gene promoter identified by one of the promoter sequences SEQ ID NO:11, SEQ ID NO:13, and SEQ ID NO:14.

Where the plant is intended for use in seed production of foreign proteins, the first coding sequence encodes the sequence of a mature, non-plant heterologous protein, and the transcriptional regulatory region is preferably one effective to hybridize under conditions of high stringency with a rice β-glucanase gene promoter identified by SEQ ID NO:11, SEQ ID NO:13, or SEQ ID NO:14.

Also forming part of the invention are seeds obtained from the above transformed monocot plants.

In yet another aspect, the invention includes a method of enhancing the resistance of a monocot plant to fungal infection by stably transforming the plant with the above chimeric gene.

The invention also includes a method of producing a heterologous protein, by the steps of stably transforming a monocot plant with the above chimeric gene, obtaining seeds from the transformed plants, germinating the seeds, and obtaining the heterologous protein from endosperm tissue from the seeds.

Also disclosed is a novel rice β-glucanase enzyme having the characteristics of a rice β-glucanase enzyme whose primary sequence is identified by one of the sequences SEQ ID NO:34, SEQ ID NO:36, SEQ ID NO:38, SEQ ID NO:40, SEQ ID NO:42, SEQ ID NO:44, SEQ ID NO:46, and SEQ ID NO:48, corresponding to rice β-glucanase 2–9 enzymes.

These and other objects and features of the invention will be more fully understood when the following detailed description of the invention is read in conjunction with the accompanying drawings.

DETAILED DESCRIPTION OF THE INVENTION

I. Definitions

Figure 1:
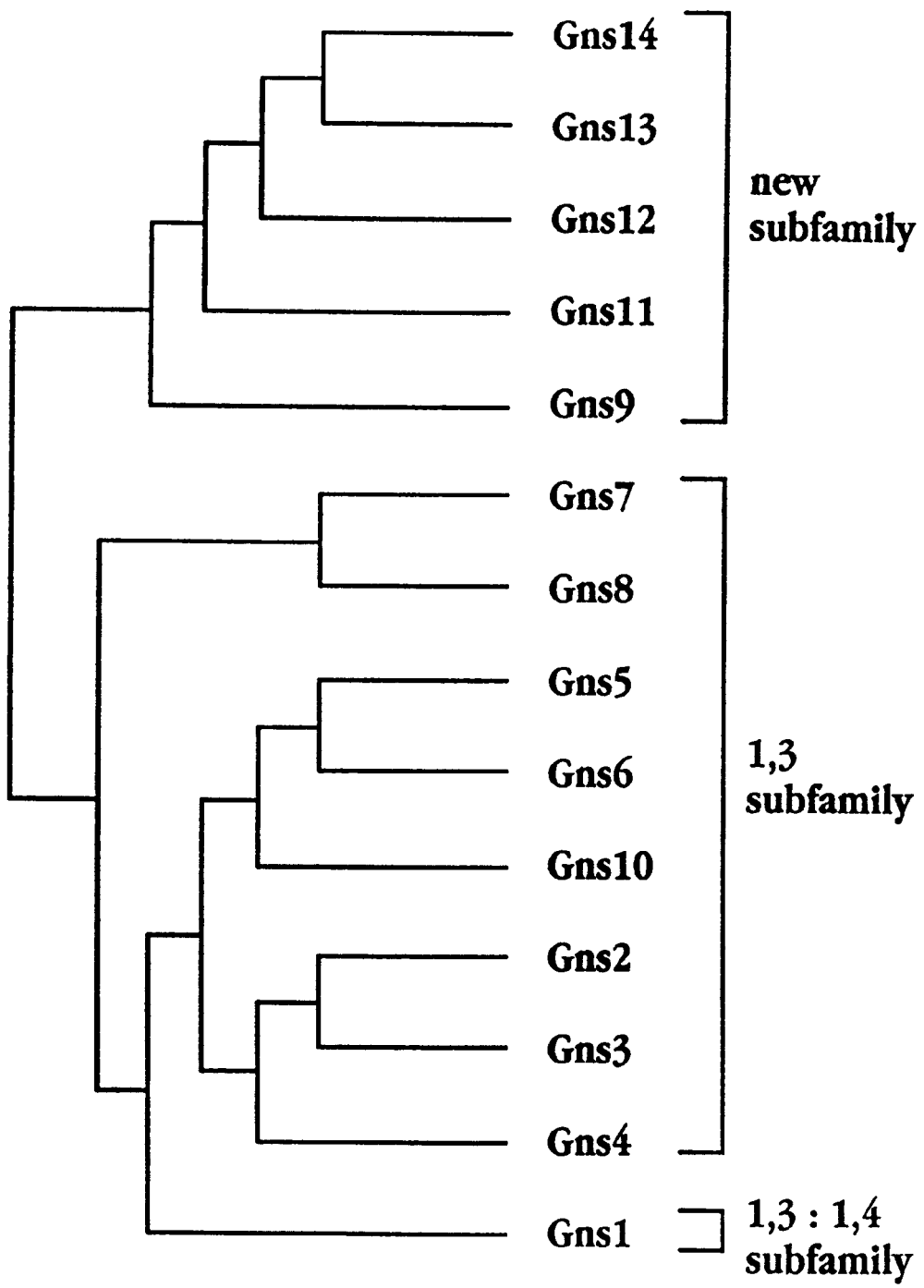
FIG. 1 shows a dendogram of the rice β-glucanase gene family.

The terms below have the following meaning, unless indicated otherwise in the specification.

A "regulatable" promoter is upregulated ("turned on" or "induced") or downregulated ("turned off") in response to a biochemical stimulus, such as the presence or absence of a small molecule, or in a particular tissue (e.g. callus tissue, root tissue, etc.) or at a particular stage in plant development (e.g., during seed maturation).

A "constitutive" promoter is a promoter which is absent of any regulation, i.e., is unregulated.

"Inducible" refers to a promoter that is upregulated by the presence or absence of a small molecule, or is upregulated in a particular tissue (e.g., callus tissue, or root tissue, etc.) or at a particular stage in plant development (e.g., during seed maturation).

"Inducible during germination" refers to a promoter which is upregulated significantly (greater than 25%) during seed germination.

"Small molecules", in the context of promoter induction, are typically small organic or bioorganic molecules less than about 1 kilodalton. Examples of such small molecules include sugars, sugar-derivatives (including phosphate derivatives), and plant hormones (such as, gibberellic or absissic acid).

"Heterologous DNA" or "foreign DNA" refers to DNA, and typically to a DNA coding sequence ("heterologous coding sequence"), which has been introduced into plant cells from another source—that is, a non-plant source or from another species of plants—or a same-species coding sequence which is placed under the control of a plant promoter that normally controls another coding sequence. An insulin coding sequence placed under the control of a plant promoter is an example of a heterologous DNA; likewise, a rice β-glucanase coding sequence placed under the control of a barley α-amylase promoter, or a rice Gns9 coding sequence placed under the control of a rice Gns4 promoter.

"Chimeric gene" refers to a gene construct containing a promoter sequence operably linked to a heterologous coding sequence, typically including a signal peptide sequence, where at least one of the components of the chimeric gene is derived from rice β-glucanase genes Gns2–Gns9.

A "transcription regulatory region" or "promoter" refers to nucleic acid sequences that influence and/or promote initiation of transcription. Promoters are typically considered to include regulatory regions, such as enhancer or inducer elements.

"Operably linked" refers to components of a chimeric gene or an expression cassette that function as a unit to express a heterologous protein. For example, a promoter operably linked to a heterologous DNA, which encodes a protein, promotes the production of functional mRNA corresponding to the heterologous DNA.

A DNA sequence is "derived from" a gene, such as a rice β-glucanase gene, if it corresponds in sequence to a segment or region of that gene. Segments of genes which may be derived from a gene include the promoter region, the 5' untranslated region, and the 3' untranslated region of the gene.

A "product" encoded by a DNA molecule includes, for example, RNA molecules and polypeptides.

"Substantially isolated", referring to a polynucleotide or polypeptide, refers to the at least partial purification of a polynucleotide or polypeptide away from unrelated or contaminating components.

"Stably transformed" refers to a cereal cell or plant that has foreign nucleic acid stably integrated into its genome which is transmitted through multiple generations.

"Cell culture" refers to cells and cell clusters, typically callus cells, growing on or suspended in a suitable growth medium.

"Germination" refers to the breaking of dormancy in a seed and the resumption of metabolic activity in the seed, including the production of enzymes effective to break down starches in the seed endosperm.

"Sequence identity" refers to the degree of identity between two sequences when those sequences are aligned using the "LALIGN" sequence alignment program (or analogous program) using default parameters. "LALIGN" is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

When a first polynucleotide fragment or polypeptide fragment is said to "correspond to" a second polynucleotide fragment or polypeptide fragment, respectively, it means that the fragments or regions are essentially co-extensive with one another when the sequences representing the fragments are aligned using a sequence alignment program, such as "LALIGN" or "MACVECTOR" (IBI, New Haven, Conn.). "Corresponding" polynucleotide or polypeptide fragments typically contain a similar, if not identical, number of residues. It will be understood, however, that corresponding fragments may contain insertions or deletions of residues with respect to one another, as well as some differences in their sequences.

A "complete coding sequence", or "CDS", refers to a DNA sequence which encodes a full-length protein or polypeptide. A CDS typically begins with a start codon ("ATG") and ends at (or one before) the first in-frame stop codon ("TAA", "TAG", or "TGA").

A "rice Gns2 CDS" is defined as a CDS which encodes the polypeptide represented by SEQ ID NO:50. An exemplary Gns2 CDS has the sequence SEQ ID NO:49.

A "rice Gns3 CDS" is defined as a CDS which encodes the polypeptide represented by SEQ ID NO:52. An exemplary Gns3 CDS has the sequence SEQ ID NO:51.

A "rice Gns4 CDS" is defined as a CDS which encodes the polypeptide represented by SEQ ID NO:54. An exemplary Gns4 CDS has the sequence SEQ ID NO:53.

A "rice Gns5 CDS" is defined as a CDS which encodes the polypeptide represented by SEQ ID NO:56. An exemplary Gns5 CDS has the sequence SEQ ID NO:55.

A "rice Gns6 CDS" is defined as a CDS which encodes the polypeptide represented by SEQ ID NO:58. An exemplary Gns6 CDS has the sequence SEQ ID NO:57.

A "rice Gns7 CDS" is defined as a CDS which encodes the polypeptide represented by SEQ ID NO:60. An exemplary Gns7 CDS has the sequence SEQ ID NO:59.

A "rice Gns8 CDS" is defined as a CDS which encodes the polypeptide represented by SEQ ID NO:62. An exemplary Gns8 CDS has the sequence SEQ ID NO:61.

A "rice Gns9 CDS" is defined as a CDS which encodes the polypeptide represented by SEQ ID NO:64. An exemplary Gns9 CDS has the sequence SEQ ID NO:63.

It will be understood that a coding sequence which encodes a polypeptide having minor amino acid substitutions, insertions, deletions, and the like, relative to a reference polypeptide, where such amino acid change(s) do not substantially alter the activity or functional properties of the altered polypeptide relative to the reference polypeptide, is considered to be an equivalent of the CDS encoding the reference polypeptide. Similarly, such an altered polypeptide, having substantially the same activity or functional properties as the reference polypeptide, is considered to be an equivalent of the reference polypeptide.

II. Rice β-Glucanase Genes Gns2–Gns9

A. Isolation of Gns2–9

Experiments performed in support of the present invention and detailed in Example 1, below, have led to the discovery of eight novel rice β-glucanase genes, termed Gns2, Gns3, Gns4, Gns5, Gns6, Gns7, Gns8, and Gns9. The genomic sequences of these genes are provided herein as SEQ ID NO:1, SEQ ID NO:2, SEQ ID NO:3, SEQ ID NO:4, SEQ ID NO:5, SEQ ID NO:6, SEQ ID NO:7, and SEQ ID NO:8, respectively.

The promoter regions for these genes are contained in the portions of these sequences upstream of the initiation ("ATG") codon. This initiation codon is located at the following positions in the eight genomic sequences referred to above: Gns2-nt 687; Gns3-nt 608; Gns4-nt 321; Gns5-nt 400; Gns6-nt 1027; Gns7-nt 846; Gns8-nt 494; and Gns9-nt 956. The sequences of the promoter-containing regions of Gns2, Gns3, Gns4, Gns5, Gns6, Gns7, Gns8, and Gns9 are provided herein as SEQ ID NO:9, SEQ ID NO:10, SEQ ID NO:11, SEQ ID NO:12, SEQ ID NO:13, SEQ ID NO:14, SEQ ID NO:15 and SEQ ID NO:16, respectively.

Sequence analyses of the Gns2–9 sequences indicated that the genes contain two exons and a single intron. The presence of the intron is supported by conserved splice junction sequences, and the similarity to the intron's location in other higher plant 1,3-β-glucanase genes, such as rice Gns1;1 (Simmons, 1992), barley EI (Slakeski, et al., 1990; Litts, et al., 1990), barley EII (Wolf, 1991), barley GIII (Wang, et al., 1992), and barley GVII (Malehorn, et al., 1993).

Further, all of the genes encode a putative N-terminal signal peptide having charged N- and C-termini, and a highly hydrophobic central core. The signal peptide directs the nascent glucanase polypeptide into the endoplasmic reticulum (Linthorst, 1991). The signal peptide coding regions were identified based on similarity to the β-glucanase signal peptides of other glucanase genes. In each case, the signal peptide is encoded by the entire first exon and a portion of the second exon. The signal peptide sequences can be obtained by splicing the genomic sequences as follows: Gns2-join (687 . . . 787,1294 . . . 1303); Gns3-join (608 . . . 686,1018 . . . 1028); Gns4-join (321 . . . 397,1395 . . . 1405); Gns5-join (400 . . . 469,909 919); Gns6-join (1027 . . . 1090,1235 . . . 1245); Gns7-join (846 . . . 909,1867 . . . 1877); Gns8 -join (494 . . . 563,1663 . . . 1673); and Gns9-join (956 . . . 1028, 1127 . . . 1137). The sequences encoding the predicted signal peptides of Gns2, Gns3, Gns4, Gns5, Gns6, Gns7, Gns8, and Gns9 are provided herein as SEQ ID NO:17, SEQ ID NO:19, SEQ ID NO:21, SEQ ID NO:23, SEQ ID NO:25, SEQ ID NO:27, SEQ ID NO:29, and SEQ ID NO:31, respectively. Amino acid sequences of the predicted signal peptides are provided as SEQ ID NO:18, SEQ ID NO:20, SEQ ID NO:22, SEQ ID NO:24, SEQ ID NO:26, SEQ ID NO:28, SEQ ID NO:30, and SEQ ID NO:32, respectively.

The mature proteins (i.e., the proteins without the signal peptides) of Gns2, Gns3, Gns4, Gns5, Gns6, Gns7, Gns8, and Gns9 are derived from the following regions of the genomic sequences: Gns2-1304 . . . 2227; Gns3-1029 . . . 1946; Gns4-1406 . . . 2314; Gns5-920 . . . 1831; Gns6-1246 . . . 2166; Gns7-1878 . . . 2810; Gns8-1674 . . . 2612; and Gns9-1138 . . . 2184. The polynucleotide sequences encoding the mature proteins of Gns2–9 are provided herein as SEQ ID NO:33, SEQ ID NO:35, SEQ ID NO:37, SEQ ID NO:39, SEQ ID NO:41, SEQ ID NO:43, SEQ ID NO:45, and SEQ ID NO:47, respectively. The amino acid sequences of the predicted mature proteins are provided as SEQ ID NO:34, SEQ ID NO:36, SEQ ID NO:38, SEQ ID NO:40, SEQ ID NO:42, SEQ ID NO:44, SEQ ID NO:46, and SEQ ID NO:48, respectively.

The genomic sequences described above are spliced as follows to generate the complete coding sequences (encoding both the signal peptide and mature protein portions) for Gns2–9: Gns2-join (687 . . . 787,1294 . . . 1303); Gns3-join (608 . . . 686,1018 . . . 1949); Gns4-join (321 . . . 396,1395 . . . 2314); Gns5-join (400 . . . 469,909 . . . 1834); Gns6-join (1027 . . . 1090,1235 . . . 2169); Gns7-join (846 . . . 909,1867 . . . 2813); Gns8-join (494 . . . 563,1663 . . . 2612); and Gns9-join (956 . . . 1028,1127 . . . 2187). The polynucleotide sequences encoding these "immature" proteins of Gns2, Gns3, Gns4, Gns5, Gns6, Gns7, Gns8, and Gns9 are provided herein as SEQ ID NO:49, SEQ ID NO:51, SEQ ID NO:53, SEQ ID NO:55, SEQ ID NO:57, SEQ ID NO:59, SEQ ID NO:61, and SEQ ID NO:63, respectively. The amino acid sequences of the predicted mature proteins are provided as SEQ ID NO:50, SEQ ID NO:52, SEQ ID NO:54, SEQ ID NO:56, SEQ ID NO:58, SEQ ID NO:60, SEQ ID NO:62, and SEQ ID NO:64, respectively.

B. Sequence Identity and Specific Hybridization

Nucleic acid hybridization, i.e. the ability of a particular nucleotide molecule to hybridize with a second nucleotide under defined conditions, may be used as a functional measure of sequence identity. "Hybridization" includes any process by which a strand of a nucleic acid joins with a complementary strand through base-pairing. Thus, strictly speaking, the term refers to the ability of the complement of the target sequence to bind to the test sequence, or vice-versa.

Polynucleotide sequences having a high degree of sequence similarity or identity to a target sequence can be isolated, e.g., from a selected cDNA or genomic library, by hybridization under high stringency conditions, such as defined below. As is known in the art, hybridization is typically performed by designing a polynucleotide probe derived from the target sequence, labeling the probe with reporter moieties, and using the reporter-labeled probe to visualize the presence of similar sequences immobilized on a solid support. The probe can be labeled using any of a variety of reporter molecules known in the art and detected accordingly: for example, radioactive isotopic labeling and chemiluminescent detection reporter systems (Tropix; Bedford, Mass.).

The labeled probes may be hybridized to samples being tested using standard hybridization procedures. Typically, polynucleotide samples (e.g., mRNA or a DNA library) are immobilized or "blotted" on nylon or nitrocellulose membranes (available, e.g., from Schleicher & Schuell, Keene, N.H.). Variations of such blots include filters lifted from media (e.g., agar) plates containing a library, Northern blots, dot blots and slot blots. Following any desired crosslinking/ immobilization steps, the membranes containing the immobilized polynucleotides are washed in a pre-hybridization solution and incubated at a controlled temperature in a hybridization solution containing the probe. Following hybridization, the membranes are washed under conditions effective to result in the desired degree of hybridization specificity following standard methods (e.g., Ausubel, et al., 1992; Sambrook, et al., 1989).

Hybridization conditions are based on the melting temperature (Tm) of the nucleic acid binding complex or probe and are typically classified by degree of "stringency" of the conditions under which hybridization is measured. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify sequences having strict identity or near-strict identity with the hybridization probe; while high stringency conditions are used to identify sequences having about 80% or more sequence identity with the probe.

Nucleic acid similarity may be determined through hybridization studies. Thus, for example, nucleic acids which hybridize under "high stringency" conditions to Gns2–9 genomic sequences provided herein as SEQ ID NO:1, SEQ ID NO:2, SEQ ID NO:3, SEQ ID NO:4, SEQ ID NO:5, SEQ ID NO:6, SEQ ID NO:7, and SEQ ID NO:8, respectively, or the complements thereof, or to the portions of the Gns genomes disclosed herein, are considered Gns2–9 nucleic acid sequences, and have at least 80%, preferably at least 90%, more preferably at least 95% sequence identity with the corresponding Gns sequence to which it hybridizes.

High stringency hybridization conditions are well known in the art (see, for example, Sambrook, et al. (1989) Chapters 9 and 11, and Ausubel, F. M., et al. (1992), Chapter 6). An example of high stringency conditions includes hybridization at about 65° C. in about 5×SSPE and washing conditions of about 65° C. in about 0.1×SSPE (where 1×SSPE =0.15 sodium chloride, 0.010 M sodium phosphate, and 0.001 M disodium EDTA).

III. Chimeric Genes with Gns2–Gns9 Sequences

The invention includes chimeric genes or polynucleotide fragments useful for producing a transgenic monocot plant. Such a chimeric gene typically contains at least three elements: (i) a transcriptional regulatory region, (ii) a first DNA sequence heterologous to the regulatory region and encoding a protein to be produced by the plant, and (iii) a second DNA sequence encoding a signal polypeptide.

A. Transcription Regulatory Region

The transcriptional regulatory region, or promoter, is preferably effective to hybridize under conditions of high stringency with a rice β-glucanase gene promoter having one of the sequences SEQ ID NO:9, SEQ ID NO:10, SEQ ID NO: 11, SEQ ID NO:12, SEQ ID NO: 13, SEQ ID NO:14, SEQ ID NO:15, or SEQ ID NO:16, more preferably SEQ ID NO:11, or SEQ ID NO:16. Exemplary transcription regulatory regions have sequences contained in one of the above-listed sequences.

Figure 2:
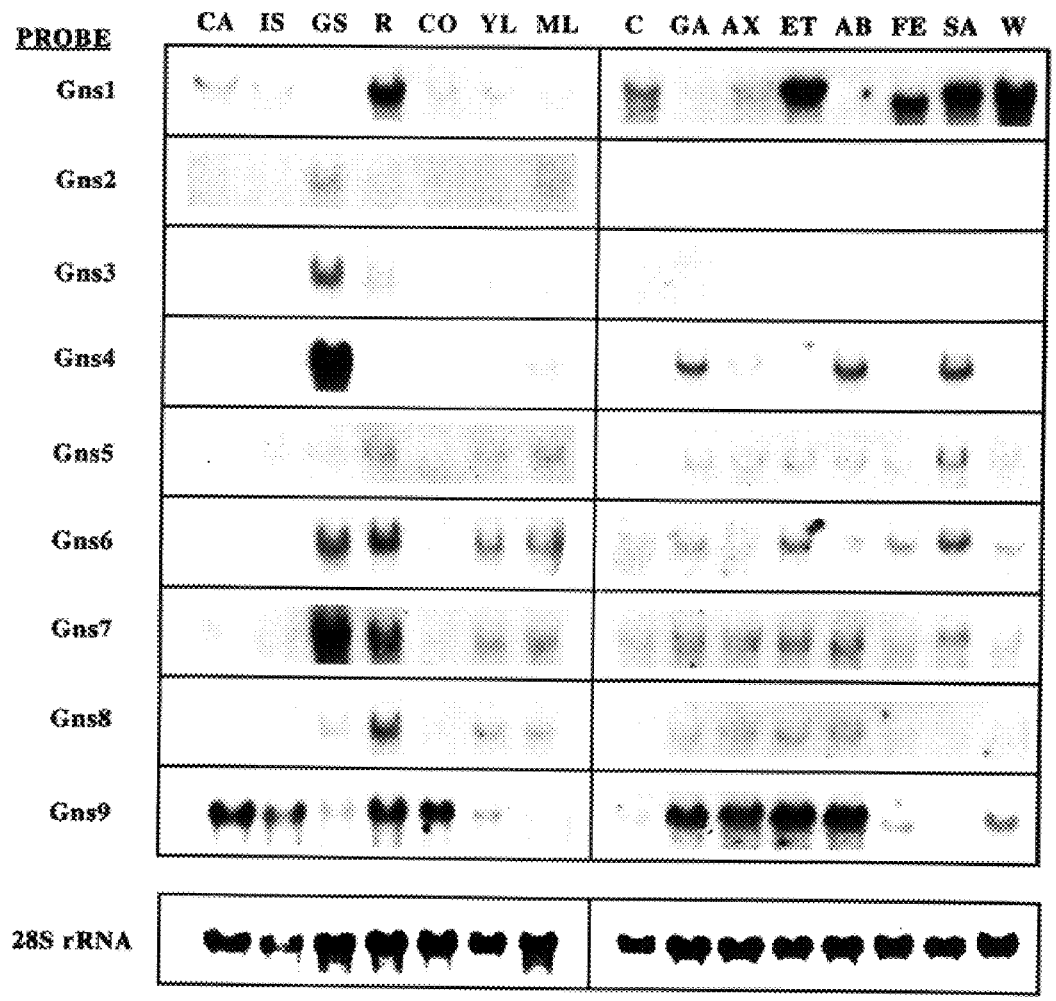
FIG. 2 shows a Northern hybridization analysis of the expression of rice β-glucanase genes Gns1–Gns9 in the indicated tissues.

Experiments detailed in Example 1, below, demonstrate how the transcriptional regulatory regions of rice β-glucanase genes Gns1–9 regulate the expression of these isozymes in various tissues and under different conditions. Exemplary results are shown in FIG. 2. It will be appreciated, for example, that the transcription regulatory regions of Gns3, Gns4, Gns6 and Gns7 result in substantial expression in germinating seeds (GS).

The Gns3 and Gns4 promoters, particularly Gns4, have particularly strong expression in GS, and have the additional advantage of being selectively expressed in the germinating seed. As such, these promoters are particularly suitable for use in chimeric genes that are used in transgenic plants to express preparative quantities of heterologous proteins in germinating seeds. Because expression of the heterologous protein is limited to the stage and tissue from which it will be harvested, it exerts only a minimal effect on the growth of the plant in general, and does not result in unnecessary expenditure of plant resources. Likewise, the Gns8 promoter shows selective expression in root tissue, and can thus be used to selectively express heterologous proteins in roots. The Gns9 promoter shows particularly strong expression in callus tissue (CA) and is particularly advantageous for expression of proteins in plant callus cell culture systems.

Alternatively, the transcriptional regulatory region may be derived from sources other than the Gns2–9 isozymes. Specifically, in applications where the encoded protein as described below is a Gns2–9 isozyme, the transcriptional regulatory region may be any suitable plant promoter that results in a desired level of expression of the Gns protein. For example, to achieve increased resistance of a particular monocot to fungal infection, the practitioner may select a constitutively-active promoter driving expression of a Gns4 coding sequence. For example, in various embodiments, the Gns4 coding sequence is under the control of the CaMV 35s promoter, the ubiquitin (ubi1) promoter, or the actin (act1) promoter.

Alternatively, the practitioner may elect to use a regulatable promoter, such as a monocot promoter inducible by addition or depletion of a small molecule, for the expression of a Gns2–9 coding sequence, or for the expression of any selected protein sequence as a fusion with a Gns2–9 signal peptide. Representative promoters include the promoters from the rice α-amylase RAmy1A, RAmy1B, RAmy2A, RAmy3A, RAmy3B, RAmy3C, RAmy3D, and RAmy3E genes, and from the pM/C, gKAmy141, gKAmy155, Amy32b, and HV18 barley α-amylase genes. These promoters are described, for example, in Ryu, et al. (1994), and references cited therein. Exemplary promoters include the RAmy3E and RAmy3D gene promoters, which are upregulated by sugar depletion in cell culture, and the RAmy1A gene promoter, which is upregulated during seed germination.

B. Encoded Protein

The chimeric gene further includes a first DNA sequence heterologous to the transcriptional regulatory region and encoding a protein to be produced by the transgenic plant. The protein may be, for example, a heterologous Gns chimeric gene, such as a Gns4 isozyme in combination with a Gns7 transcriptional regulatory region. The β-glucanase isozyme encoded by Gns4 is a member of the 1–3 β-glucanase subfamily of the rice β-glucanase genes. This enzyme activity is associated with inhibition of fungal hyphal growth in plants. By placing the Gns4 isozyme under the control of, for example, the Gns7 promoter, which is expressed germinating seeds, roots, and leaves, increased fungal protection may be achieved in those tissues. Alternatively, the Gns4 isozyme may be joined to another plant promoter that is strongly expressed in, e.g., maturing seeds. Using a suitable transformation method, (e.g., microprojectile bombardment, Agrobacteria, electroporation, etc.) this chimera can be stably integrated into the plant genome and expressed in the appropriate tissue and developmental stage using the transcriptional and translational machinery of the plant cell. Production of high levels of 1–3 β-glucanase activity in susceptible tissues of the plant may thus be used to confer resistance to fungal pathogens. Furthermore, one of the rice 1–3 β-glucanase genes may be cotransformed into a susceptible plant with another fungal defense gene such as chitinase, to achieve even higher and more durable levels of pathogen resistance.

Of course, proteins other than glucanase may be expressed according to the present invention. In particular, the encoded protein may be any commercially-important protein, such as an enzyme, therapeutic or diagnostic protein, or peptide. Examples of enzymes include, but are not limited to, chymosin, proteases, polymerases, saccharidases, dehydrogenases, nucleases, glucose oxidase, α-amylase, oxidoreductases (such as fungal peroxidases and laccases), xylanases, phytases, cellulases, hemicellulases, and lipases. More specifically, the invention can be used to produce enzymes such as, those used in detergents, rennin, horseradish peroxidase, amylases from other plants, soil remediation enzymes, and other such industrial proteins.

Other proteins of interest are mammalian proteins. Such proteins include, but are not limited to, blood proteins (e.g., serum albumin, Factor VII, Factor VIII (or modified Factor VIII), Factor IX, Factor X, tissue plasminogen factor, Protein C, von Willebrand factor, antithrombin III, and erythropoietin (EPO), urokinase, prourokinase, epoetin-α, colony stimulating factors (such as granulocyte colony-stimulating factor (G-CSF), macrophage colony-stimulating factor (M-CSF), and granulocyte macrophage colony-stimulating factor (GM-CSF)), cytokines (such as interleukins or interferons), integrins, addressins, selectins, homing receptors, surface membrane proteins (such as, surface membrane protein receptors), T cell receptor units, immunoglobulins, soluble major histocompatibility complex antigens, structural proteins (such as collagen, fibrin, elastin, tubulin, actin, and myosin), growth factor receptors, growth factors, growth hormone, cell cycle proteins, vaccines, fibrinogen, thrombin, cytokines, hyaluronic acid and antibodies. Coding sequences for these and other suitable proteins are known in the art.

Therapeutic proteins considered particularly suitable for expression using the methods and compositions of the invention include EPO, tissue plasminogen activator (t-PA), urokinase, prourokinase, growth hormones, cytokines, factor VIII, epoetin-α, and granulocyte colony stimulating factor.

C. Signal Sequence

The chimeric gene also includes a second DNA sequence encoding a signal polypeptide. This second DNA sequence is operably linked to the transcriptional regulatory region and the first DNA sequence, and the signal polypeptide is in translation-frame with the protein and is effective to facilitate secretion of the protein across aleurone or scutellar epithelium layers into the endosperm of seeds obtained from the plant. Further, the signal peptide may be used to facilitate secretion into the apoplast (intercellular space) of many plant tissues, including roots, shoots, leaves, stems of flowers and flower parts, and fruits. Secretion of the protein from the cells in which it is produced facilitates its isolation and purification.

Exemplary signal peptides include the N-terminal signal peptides of the Gns2–9 isozymes. The DNA sequences encoding these signal peptides are provided as SEQ ID NO:17, SEQ ID NO:19, SEQ ID NO:21, SEQ ID NO:23, SEQ ID NO:25, SEQ ID NO:27, SEQ IDNO:29, and SEQ IDNO:31. In a preferred embodiment, the DNA sequence encoding the signal peptide is positioned downstream of the transcriptional regulatory sequences and upstream of, and in translation frame with, the first DNA sequence.

D. Codon Optimization

In another embodiment of the invention, the coding region for the signal sequence, and/or the coding region for the encoded protein, may be codon-optimized for optimal expression in plant cells, e.g., rice cells. A codon-optimized sequence may be generated using the information in Table 1, below. To generate this table, the coding sequences from rice were analyzed for codon frequency for each amino acid, and the most frequent codon was selected for each amino acid. The optimal codons selected in this manner for rice are shown in Table 1.

TABLE 1

| Amino Acid | Rice Preferred Codon |
|---|---|
| Ala A | GCC |
| Arg R | CGC |
| Asn N | AAC |
| Asp D | GAC |
| Cys C | UGC |
| Gln Q | CAG |
| Glu E | GAG |
| Gly G | GGC |
| His H | CAC |
| Ile I | AUC |
| Leu L | CUC |
| Lys K | AAG |
| Phe F | UUC |
| Pro P | CCG |
| Ser S | AGC |
| Thr T | ACC |
| Tyr Y | UAC |
| Val V | GUC |
| stop | UAA |

E. 5' and 3' Untranslated Regions

The chimeric gene may further include, between the promoter and coding sequences, the 5' untranslated region (5' UTR) of an inducible monocot gene, such as the 5' UTR derived from one of the rice genes mentioned above. Further, the gene may include, downstream of the coding sequence, the 3' untranslated region (3' UTR) from an inducible monocot gene, such as one of the rice or barley genes mentioned above. Such sequences typically include non-coding sequence 5' to the polyadenylation site, the polyadenylation site and the transcription termination sequence. The transcriptional termination region may be selected particularly for stability of the mRNA to enhance expression. Illustrative transcriptional termination regions include the NOS terminator from Agrobacterium Ti plasmid and the rice α-amylase RAmy1A terminator.

Polyadenylation tails (Alber and Kawasaki, 1982) are also commonly added to optimize high levels of transcription and proper transcription termination, respectively. Polyadenylation sequences include but are not limited to the Agrobacterium octopine synthetase signal, Gielen, et al. (1984) or the nopaline synthase of the same species Depicker, et al. (1982).

It will be understood that such additional elements as the 5'UTR and 3'UTR may be incorporated as part of the chimeric gene, or as part of a vector used to deliver the chimeric gene to a plant host. Examples of suitable vectors are described below.

IV. Plant Transformation

A. Transformation Vector

For transformation of plants, the chimeric gene of the invention is placed in a suitable expression vector designed for operation in plants. The vector includes suitable elements of plasmid or viral origin that provide necessary characteristics to the vector to permit the vectors to move DNA from bacteria to the desired plant host. Suitable transformation vectors are described in related application PCT WO 95/14099, published May 25, 1995, which is incorporated by reference herein.

In addition to the chimeric genes described above, vectors constructed according to the present invention may contain sequences suitable for permitting integration of the coding sequences into the plant genome. These might include transposon sequences, and the like, for homologous recombination, as well as Ti sequences which permit random insertion of a heterologous expression cassette into a plant genome. The vectors may further include a selectable marker gene, such as antibiotic or herbicide resistance genes, including, for example, the nptII kanamycin resistance gene, for selection in kanamycin-containing media, or the phosphinothricin acetyltransferase gene, for selection in media containing phosphinothricin (PPT), or the hph hygromycin phosphotransferase gene, for selection in media containing hygromycin B.

The vectors may also include sequences that allow their selection and propagation in a secondary host, such as sequences containing an origin of replication and a selectable marker such as antibiotic or herbicide resistance genes expressable in the secondary host. Typical secondary hosts include bacteria and yeast. In one embodiment, the secondary host is *Escherichia coli*, the origin of replication is a colE1-type, and the selectable marker is a gene encoding ampicillin resistance. Such sequences are well known in the art and are commercially available (e.g., Clontech, Palo Alto, Calif.; Stratagene, La Jolla, Calif.).

For Agrobacterium transformations, vectors containing chimeric genes of the present invention may be modified to include T DNA sequences for Agrobacterium-mediated transfer to plant chromosomes. Further, the vectors of the invention may comprise a disarmed plant tumor inducing plasmid of *Agrobacterium tumefaciens*. Where the heterologous gene is not readily amenable to detection, the construct will preferably also have a selectable marker gene suitable for determining if a plant cell has been transformed. A general review of suitable markers for the members of the grass family is found in Wilmink and Dons, 1993, *Plant Mol. Biol. Reptr*, 11(2):165–185.

B. Transformation of Plant Cells

The plants used in the processes of the present invention are derived from monocots, particularly the members of the taxonomic family known as the Gramineae. This family includes all members of the grass family of which the edible varieties are known as cereals. The cereals include a wide variety of species such as wheat (Triticum sps.), rice (Oryza sps.) barley (Hordeum sps.) oats, (Avena sps.) rye (Secale sps.), corn (Zea sps.) and millet (Pennisettum sps.). In the present invention, preferred family members are rice and barley.

Plant cells or tissues derived from the members of the family are transformed with expression constructs (i.e., plasmid DNA into which the chimeric gene of the invention has been inserted) using a variety of standard techniques, including microparticle bombardment (Klein, et al., 1987; Knudsen and Muller, 1991), electroporation (Fromm, et al., 1985), and protoplast fusion (Fraley, et al., 1982). In the present invention, particle bombardment is the preferred transformation procedure. Various methods for direct or vectored transformation of plant cells, e.g., plant protoplast cells, have been described, e.g., in above-cited PCT application WO 95/14099.

In one embodiment, the embryo and endosperm of mature seeds are removed to exposed scutulum tissue cells. The cells may be transformed by DNA bombardment or injection, or by vectored transformation, e.g., by Agrobacterium infection after bombarding the scuteller cells with microparticles to make them susceptible to Agrobacterium infection (Bidney, et al., 1992).

One suitable transformation method follows the techniques detailed generally in Sivamani, et al. (1996); Zhang, et al. (1996); and Li, L., et al. (1993). Briefly, rice seeds are sterilized by standard methods, and callus induction from the seeds is carried out on NB media with 2,4D. During a first incubation period, callus tissue forms around the embryo of the seed. By the end of the incubation period, (e.g., 14 days at 28° C.) the calli are about 0.25 to 0.5 cm in diameter. Callus mass is then detached from the seed, and placed on fresh NB media, and incubated again for about 14 days at 28° C.. After the second incubation period, satellite calli develop around the original "mother" callus mass. These satellite calli are typically slightly smaller, more compact and defined than the original tissue, and are transferred to fresh media.

Calli to be bombarded are selected from 14 day old subcultures. The size, shape, color and density are all important in selecting calli in the optimal physiological condition for transformation. The calli should be between 0.8 and 1.1 mm in diameter. The calli should appear as spherical masses with a rough exterior.

Transformation is by particle bombardment, as detailed in the references cited above. After the transformation steps, the cells are typically grown under conditions that permit expression of the selectable marker gene, such as hph. It is preferred to culture the transformed cells under multiple rounds of selection to produce a uniformly stable transformed cell line.

V. Cell Culture Production of Heterologous Proteins

Transgenic cells, typically callus cells, are cultured under conditions that favor plant cell growth, until the cells reach a desired cell density, then under conditions that favor expression of the mature protein under the control of the given promoter. Preferred cell culture conditions are disclosed in Example 2. Purification of the mature protein secreted into the medium is by standard techniques known by those of skill in the art.

VI. Production of Heterologous Proteins in the Plant

To produce a selected heterologous protein in a monocot plant, the plant cells transformed as above are used to regenerate plants. Plant regeneration from cultured protoplasts or callus tissue is carried by standard methods, e.g., as described in Evans, et al. (1983); and Vasil (1984, 1986) and as described in PCT application WO 95/14099. The transgenic seeds obtained from the regenerated plants are harvested, and are either used to grow new plants or are germinated.

If the heterologous protein is to be isolated from germinating seeds, the seeds are prepared for germination by an initial steeping step, followed by malting, as detailed, for example, in the above-cited PCT application. The mature protein secreted from aleurone cells into the endosperm tissue of the seed can be isolated by standard methods. Typically, the seeds are mashed to disrupt tissues, the seed mash is suspended in a protein extraction buffer, and the protein is isolated from the buffer by conventional means.

It will be noted that the expression of the coding sequences contained in the chimeric genes of the invention is not necessarily restricted to seeds, particularly when promoters active in other tissues are employed. Accordingly, heterologous proteins encoded by such chimeric genes may also be expressed and harvested from whatever tissue is expressing them, for example, from roots, leaves, coleoptiles, or callus cells of the transgenic plant.

VII. Fusion Protein

In another aspect, the present invention relates to a fusion protein having an N-terminal region containing a rice β-glucanase signal sequence peptide from any of Gns2–9 and, immediately adjacent the C-terminal amino acid of said region, a heterologous protein other than a rice Gns2–9 β-glucanase isozyme. In an exemplary embodiment, the N-terminal region has a sequence selected from the group consisting of SEQ ID NO:18, SEQ ID NO:20, SEQ ID NO:22, SEQ ID NO:24, SEQ ID NO:26, SEQ ID NO:28, SEQ ID NO:30 and SEQ ID NO:32. The heterologous protein is preferably a commercial therapeutic protein or peptide such as erythropoietin (EPO), tissue plasminogen activator (t-PA), urokinase, prourokinase, a growth hormone, a cytokine, factor VIII, epoetin-α, or granulocyte colony stimulating factor.

VIII. Applications of Expressed Proteins

A. Gns Proteins

A1. Characteristics of Gns2–4 Proteins

The mature peptides Gns2, Gns3 and Gns4 are 304–309 amino acids long, with calculated molecular weights of 33.2–33.3 kD. The Gns2 and Gns3 mature peptides have predicted pIs in the acidic range, while that of Gns4 is basic. All three have a potential N-glycosylation site (Hubbard and Ivatt, 1981) located in the middle of the Gns2 isozyme, and close to the carboxyl terminus in both Gns3 and Gns4. The mature peptides have a mean of 77.1% similarity to each other, homology being highest between Gns3 and Gns4. Alignment of peptide sequences for the rice Gns2, Gns3 and Gns4 genes together with rice Gns1;1 (Simmons, 1992) and barley GII (Wolf, 1991) shows highly conserved regions at the N-terminal, third quarter and C-terminal regions of the protein.

The deduced protein sequences of the Gns2, Gns3 and Gns4 genes were compared to those of other β-glucanase genes: rice Gns1;1 (Simmons, 1992), barley EI (Slakeski, et al., 1990; Litts, et al., 1990), barley EII (Wolf, 1991), oat glucanase (Yun, et al., 1993), barley GI–GVI (Xu, et al., 1992), barley GVII (Abg2) (Malehorn, et al., 1993), barley Gns2;8, wheat glucanase and maize glucanase (Wu, et al., 1994). The rice Gns2, Gns3 and Gns4 DNA sequences were more similar to those of the 1,3-β-glucanase genes than to those of the 1,3;1,4-β-glucanase genes. In the Gns2, Gns3 and Gns4 deduced protein sequences the majority of the diagnostic amino acid residues (Varghese, et al., 1994) are either identical or similar to those found in the 1,3-β-glucanases.

A2. Effects of Gns Proteins on Cell Growth 1,3-β-Glucanases in the apoplast participate in many stages of plant growth and development including seed germination, coleoptile growth, microspore development, pollen tube growth, flower formation, cell division, and fruit ripening (Simmons, 1994). It is contemplated that plants transformed with a selected Gns2–9 isozyme, such as Gns4, under control of a heterologous promoter which expresses in a range of tissues (such as the CaMV 35s promoter, the ubiquitin (ubi1) promoter, or the actin (act1) promoter), have enhanced growth and development characteristics.

A3. Gns Proteins and Fungal Resistance

There is substantial evidence supporting functional roles for the 1,3-β-glucanases in plant defense and plant growth. When fungi invade the plant, the 1,3-β-glucanases in the apoplast release glucan oligosaccharide elicitors from the fungal cell wall through limited hydrolysis. On perceiving the elicitor signal, the plant induces expression of many defense-related genes via the octadecanoid signal pathway (Benhamou, 1996; Mueller, et al., 1993). Lysis of plant cells at the site of a fungal infection releases large amounts of vacuolar 1,3-β-glucanases and chitinases which may participate in lysis of the fungal cell (Sela-Buurlage, et al., 1993). According to the present invention, chimeric genes encoding a Gns2–9 isozyme may be used to generate transgenic plants having enhanced resistance to insects and microbial pathogens, particularly fungal pathogens, relative to untransfected plants.

B. Other Expressed Proteins

As described above, the chimeric genes of the invention can be used to express and produce, in transgenic monocots, a variety of useful therapeutic, diagnostic, nutritional or industrial proteins and/or peptides. For example, the regulatory DNA sequences (i.e., promoters) from Gns4, which is strongly expressed in germinating seeds, can be fused to a gene encoding a commercially important protein such as a hormone, vaccine, antibody, enzyme, enzyme inhibitor, etc. As described above, the chimera can be used to create transgenic plants that can be used to produce such protein or peptide products. Because the various rice β-glucanase genes are expressed in different tissues, at different stages of development and in response to different exogenous regulatory molecules, it is possible to express these commercial proteins in the roots, mature and germinated seeds, coleoptiles and/or callus cells of the transgenic plant.

The following examples are provided by way of illustration only and not by way of limitation. Those of skill will readily recognize a variety of noncritical parameters which could be changed or modified to yield essentially similar results.

Materials and Methods

Generally, the nomenclature and laboratory procedures with respect to standard recombinant DNA technology can be found in Sambrook, et al. (1989) and in Gelvin and Schilperoot (1988). Other general references are provided throughout this document. The procedures therein are known in the art and are provided for the convenience of the reader.

A. Genomic Library Screening

A genomic library constructed in λEMBL3 from rice cv. M202 was screened using hybridization methods described previously (Simmons, et al., 1992; Litts, et al., 1990). The probes included a 513-bp NarI fragment of barley endo-β-glucanase E1 gene (Hv29) (Litts, et al., 1990; Slakeski, et al., 1990) and a 2.5 kb EcoRI-SalI fragment of the HORvu;Gns2;8 gene (Hv34), a barley endo-β-glucanase gene. The lambda clones were plaque purified; then restriction fragments that hybridized to the probe were subcloned into pUC19 or pBlueScript plasmid vectors.

B. Polymerase Chain Reaction (PCR) Assay

Forward primer, oligonucleotide 528 (SEQ ID NO:65), anneals at position 13 to 33 in Gns1;1 exon 2. Reverse primer, oligonucleotide 529 (SEQ ID NO:66), anneals at position 838 to 858 in Gns1;1 exon 2. 10 ng DNA template was amplified via PCR (Mullis, 1987; Mullis, et al., 1987) in a 50 μl reaction solution composed as described previously (Foolad, et al., 1993). Amplification was performed in a TWINBLOCK thermal cycler (Ericomp, San Diego, Calif.) for 30 cycles of 2 min melting at 96° C., 1 min annealing at 45° C., and 2 min extension at 72° C. An aliquot of amplification product was fractionated in 1% agarose gel containing 60 µg/ml ethidium bromide. 30 µl of the product was also directly digested by 10 units of HincII, HinfI, NcoI, or MboI (New England Biolabs; Beverly, Mass.). The digestion products were separated on a 6% polyacrylamide gel at 300 volts for 4 hr, and visualized by ethidium bromide staining.

C. DNA Sequencing and Gene Nomenclature

The DNA sequences of β-glucanase gene clones were determined by primer-walk methods. Oligonucleotide primers were synthesized by Gibco-BRL or OnlyDNA. AMPLIFY software was used to check for dimer formation between primers. The sequences were confirmed by using both strands as template or running at least two passes on the same strand. Template DNA for sequencing was prepared using PREP8 columns (Qiagen; Chatsworth, Calif.). SEQUENASE version 2.0 (USB/Amersham Corporation; Arlington Heights, Ill.) was used for the chain extension and termination steps for manual sequencing. Automated sequencing was carried out on ABI Automated Sequencers.

Wisconsin Package Version 8 (Genetics Computer Group (GCG), Madison, Wis.) and MACVECTOR software (International Biotechnologies, Inc., New Haven Conn.) were used for analysis of DNA sequence data. LINE-UP software (GCG) was used to assemble sequence overlaps. MAP software (GCG) was used to locate open reading frames in the DNA sequence. PILEUP software (GCG) was used for alignment of related DNA and protein sequences. BESTFIT software (GCG) was used to calculate the similarities of the aligned sequences.

D. DNA and RNA Hybridization

Southern blots and dot blots were prepared with nylon membrane (HYBOND-N+; Amersham) according to the manufacturer's instructions. DNA slot blots were prepared using a slotblot apparatus (MINIFOLDII; Schleicher & Schuell). Northern blots were made on nylon membrane using the NORTHERNMAX kit (Ambion, Hialeah, Fla.). Total RNA was isolated from 1 gm of the indicated tissue as described (Huang, et al., 1990), or from 0.1 gm of tissue using RNEASY (Qiagen). RNA quality was checked by electrophoresis on a 1% agarose gel followed by ethidium bromide staining. The 28S and 18S rRNA bands showed little or no evidence of smearing.

Isozyme-specific probes were made from fragments at the 3' ends of the Gns genes either by PCR amplification or by isolation of restriction fragments. For example, the Gns1 probe was a PCR product including 84 bases at the end of exon 2 and 650 bases of the 3' flanking region; the Gns2 probe was a 600 base SalI-XbaI fragment; the Gns3 probe was a 500 base SmaI-XhoI fragment; and the Gns4 probe was a 600 base XbaI-EcoRI fragment.

DNA probe fragments were $^{32}$P-labeled to at least $10^8$ cpm/µg specific activity using a REDIPRIME kit (Amersham), purified through a P10 gel column (BioRad; Richmond, Calif.) and used at $10^6$ cpm/ml in prehybridization/hybridization solution (Ambion). Oligonucleotides were 32P-endlabeled by T7 polynucleotide kinase. Prehybridization was carried out for 30 min, and hybridization carried out overnight, both at 42° C. The blots were washed twice in 2% SDS, 0.1×SSC for 15 min at room temperature and twice in 0.1% SDS, 0.1×SSC for 1 hr at 55° C., and exposed to X-ray film (X-OMAT; Eastman Kodak, Rochester, N.Y.) at −70° C. for 1–4 days. The autoradiographs were scanned on an Epson scanner using PHOTO-SHOP ver. 2.5 software (Adobe Systems, Inc.; Mountain View, Calif.); densitometry of scanned images was carried out using MACBAS ver. 2.0 software (Fuji Photo Film Co., Ltd.).

E. Plant Materials and Treatments

Production of aseptic root and shoot material, application of treatments to shoot, and harvesting were as described previously (Simmons, et al., 1992). Coleoptiles of 2 to 5 cm in length were collected from seeds grown 5-cm deep in moist vermiculite for 3 days in the dark.

EXAMPLE 1

Isolation of Eight Novel Rice β-Glucanase Genes

A. Library Screen

Six genome equivalents of rice genomic library were screened to yield sixty glucanase candidate clones. A PCR assay was used to further identify lambda clones which contained glucanase genes. Conserved glucanase sequences were identified by alignment of the mature peptide coding regions of the barley EII (Fincher, et al., 1986), barley GII (Wolf, 1991), barley EI (Høj, et al., 1989), and rice Gns1;1 (Simmons, et al., 1992) genes. Two highly conserved domains were located near the 5' and 3' ends of exon 2. Forward primer oligonucleotide 528 (SEQ ID NO:65), and reverse primer oligonucleotide 529 (SEQ ID NO:66) were designed based on these conserved domains, and then used to screen putative β-glucanase genomic clones by PCR. The PCR products were then digested with HincII, HinfI, MboI, NcoI, or MboI. Sibling clones were identified based on similarity of fragment profiles. The profile analysis indicated that the clones fell into eight distinct groups, representatives of which were sequenced as described above and termed Gns2–9.

B. Sequence Analysis

The sequences of Gns2–9 were compared with the sequences of Gns1 and Gns10–14 using a phylogeny analysis program. The dendogram generated by the program is shown in FIG. 1. As can be appreciated from the figure, the genes Gns1–Gns8 & Gns10 form two subfamilies. Comparisons of these sequences to the glucanase sequences in barley and other cereals suggest that Gns1 (Simmons, et al., 1992) represents the 1,3;1,4-β-glucanase subfamily of rice, while Gns2–Gns8 and Gns10 represent the 1,3-β-glucanase subfamily. The comparisons further suggest that the cluster of Gns9 and Gns11–Gns14 is a novel and divergent group representing a novel glucanase subfamily.

Modeling of the 3D structure of the rice glucanase isozymes indicated that many of the sequence changes that distinguish Gns9 from Gns1 have little effect on the predicted 3D structures. One striking difference in structure is that α-helix a7 (Varghese, et al., 1994) adjacent to the catalytic domain (Chen, et al., 1995) is disrupted in the Gns9 isozyme, suggesting that the substrate specificity of this new Gns9 group may be distinct from that of the other glucanase subfamilies.

C. Genomic Southern Hybridization

Southern hybridization was done to estimate the size of the β-glucanase gene family in rice cultivar M202. Genomic DNA was isolated from fresh leaves of transgenic plants using the method of Dellaporta et al. (1983) digested using EcoRI, BamHI, SalI, SmaI, XbaI and XhoI and blotted as described above. Identical blots were probed with oligonucleotide 716 (a generic β-glucanase probe corresponding to the highly conserved 3' region encoding the catalytic domain of the mature β-glucanase enzyme; Varghese, et al., 1994) or with isozyme-specific oligonucleotide probes corresponding to the 3' flanking region of each gene. Probing with an oligonucleotide precluded hybridization to split target sequences that could otherwise have lead to an overestimation of copy number.

In experiments performed as described above, Southern hybridization using the oligonucleotide 716 probe showed eight intense bands in rice genomic DNA. The isozyme-specific probes in turn recognized genomic bands that correspond to each of the Gns gene clones.

The specificity of the isozyme-specific probes was independently verified by slot-blot analysis. Either 1 pg or 100 pg of each Gns genomic clone was blotted and probed using the isozyme-specific 3' flanking region probes described above. Very little cross-hybridization was observed among the gene clones.

D. Northern Hybridization Analysis

Northern hybridization was performed as described above to characterize expression of the Gns2–9 genes. Total RNA from various rice plant organs (untreated, or young leaves treated as described below) was hybridized with the isozyme-specific probes described above and visualized using autoradiography. Exemplary results are shown in FIG. 2. Abbreviations for tissue sources are as follows: CA—callus; IS—immature seed; GS—germinated seed; R—root; CO—coleoptile; YL—etiolated young leaf; ML—mature leaf. Treatments tested on young leaves are indicated as follows: C—young leaf control; GA—1 $\mu$M gibberellin A3; AX—auxin (10 $\mu$M 2,4-D); ET—ethephon (100 mg/ml Ethrel); AB—10 pM abscissic acid; FE—fungal elicitor (*Magnaporthe salvinii*); SA—10 mM salicylic acid; W—wounding. The lower panels of FIG. 2 (labeled "28S rRNA") show blots stained with methylene blue to show the integrity and loading of 28S rRNA.

The Gns genes showed differential expression across tissues and treatments. For example, Gns2 transcripts were observed only in germinated seed, root and mature leaf, where the weak hybridization signal was visible only after 6 days of autoradiography. Stronger signals were observed for Gns3 and Gns4 after only 2 days of autoradiography. Gns3 was expressed only in germinated seed and root, where expression of Gns3 was more than 10-fold higher than that of Gns2. Neither Gns2 nor Gns3 were induced by phytohormones or stress treatments applied to young leaf tissue. Gns4 was the most actively expressed of the three genes. Gns4 was expressed very abundantly in germinated seed, where it was expressed about 10-fold higher than the Gns3 transcript. The Gns4 transcript was detected at low levels in immature seed and mature leaf. There was little or no expression of Gns4 in callus, root, coleoptile, young etiolated leaf or green leaf. Gns4 also showed strong induction of gene expression in young green leaf tissues which were treated with GA, AB and salicylic acid, and weak induction in young green leaf tissues treated with auxin.

EXAMPLE 2

Production of α-Antitrypsin in Cell Culture and in Germinating Seeds

A. AAT-Expression and Selectable Marker Transformation Vectors

A plasmid containing a chimeric gene encoding a signal sequence-mature α-antitrypsin fusion protein under the control of the Gns4 promoter (for expression in germinating seed) or the Gns9 promoter (for expression in cell culture) is constructed in view of the guidance presented above according to the procedures outlined in PCT patent application US94/13179 (WO 95/14099), filed Nov. 14, 1994, which is incorporated herein by reference. A selectable marker vector containing nucleic acid encoding the bar gene product is constructed by similar methods.

The two vectors are mixed at a molar ratio of target gene to selectable marker gene 1–6:1. 5–20 ug of DNA is added to each tube and 20 $\mu$l of 0.1 M spermidine free base is added while vortexing. Slowly, in a dropwise fashion while vortexing, 50 $\mu$l of 2.5 M CaCl$_2$ is added. The solution is allowed to stand at room temperature for 10 minutes. The solution is centrifuged for 10 seconds and the supernatant is discarded. The particles are resuspended in 60 $\mu$l of 100% ethanol by gently flicking the end of the tube. 10 $\mu$l of the particles are loaded onto one microcarrier as evenly as possible.

B. Plant Transformation

Transformation is carried out as described in Jensen, et al., 1996, and in Wan, et al., 1994, and as described above, using immature barley embryos. Typical rates of transformation are about 1% transformants per isolated immature zygotic embryo. Selection of transformed barley callus cells is on the herbicide phosphinothricin (Bialophos).

C. AAT Induction in Cell Culture

After selection of transgenic barley callus, callus cells are suspended in liquid culture containing AA2 media (Thompson, et al., 1986), at 3% sucrose, pH 5.8. Thereafter, the cells are placed in multi-well tissue culture plates and shaken at 120 rpm in the dark for 48 hours. The supernatant is then removed and stored at –80° C. prior to Western blot analysis of AAT. This procedure is also employed to further select transgenic plant cells capable of producing the desired heterologous protein.

D. AAT Expression in Germinating Seeds

The transgenic callus material from above is used to produce regenerated plants, according to standard methods. Seeds from the plants are harvested, and prepared for germination by an initial steeping step, in which the seeds immersed in or sprayed with water to increase the moisture content of the seed to between 35–45%. Steeping and germination are carried out as described above.

E. Isolation of AAT from Germinating Seeds

After optimum germination and expression of the AAT gene, the seeds are mashed (for example, by gentle grinding) to disrupt tissues and remove the hulls from the seeds. The seed mash is suspended in a protein extraction buffer, as above.

Supernatant obtained from the seeds is subjected to various purification schemes used in the wet-milling industry (e.g., hydrocloning and ion exclusion chromatography) to remove un-wanted proteins and to concentrate AAT. Alternatively, ammonium sulfate precipitation can also be used to concentrate the AAT. Affinity- and ion-exchange chromatography can be used to purify the AAT away from other proteins in the supernatant. The presence of AAT in the various chromatographic fractions can be detected using standard photometric assays. Supernatants are concentrated using Centricon-10 filters (Amicon cat. #4207; Danvers, Mass.) and washed with induction media to remove substances interfering with electrophoretic migration. Samples are concentrated approximately 10 fold. Concentrated samples are treated with an effective concentration of 1 mM PMSF for 2–5 minutes to inactivate all serine protease activity.

Although the invention has been described with reference to particular embodiments, it will be appreciated that a variety of changes and modifications can be made without departing from the invention.

It is claimed:

1. An isolated polynucleotide comprising a sequence which encodes for a rice β-glucanase isozyme and which hybridizes under conditions of high stringency with a rice β-glucanase gene selected from the group of genes identified by SEQ ID NO:1, SEQ ID NO:2, SEQ ID NO:3, SEQ ID NO:4, SEQ ID NO:5, SEQ ID NO:6, SEQ ID NO:7, and SEQ ID NO:8.

2. The isolated polynucleotide of claim 1, wherein the polynucleotide hybridizes under conditions of high stringency with a rice β-glucanase gene promoter selected from the group of gene promoters identified by SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

3. A chimeric gene for use in producing a transgenic monocot plant comprising a DNA sequence having, operatively linked in sequence in a 5' to 3' direction, a transcriptional regulatory region from a rice β-glucanase isozyme gene and which hybridizes under conditions of high stringency with a rice β-glucanase gene promoter selected from the group of promoters identified by SEQ ID NO:9, SEQ ID NO:10, SEQ ID NO: 11, SEQ ID NO:12, SEQ ID NO: 13, SEQ ID NO:14, SEQ ID NO:15, and SEQ ID NO:16, a first DNA sequence heterologous to said regulatory region, and encoding a protein to be produced by said plant, and a second DNA sequence encoding a signal polypeptide, where said second DNA sequence is operably linked to said transcriptional regulatory region and to said first DNA sequence, and where said signal polypeptide is in translation-frame with said protein and is effective to facilitate secretion of said protein across aleurone or scutellar epithelium layers into the endosperm of seeds obtained from the plant.

4. The chimeric gene of claim 3, for use in producing a heterologous protein in germinating seeds obtained from the transformed plant, wherein the transcriptional regulatory region hybridizes under conditions of high stringency with a rice β-glucanase gene promoter having a sequence selected from the group of sequences identified by SEQ ID NO:10, SEQ ID NO:11, SEQ ID NO:13, and SEQ ID NO:14.

5. The chimeric gene of claim 4, wherein the transcriptional regulatory region hybridizes under conditions of high stringency with a rice β-glucanase gene promoter having the sequence identified by SEQ ID NO:11.

6. A method of producing a heterologous protein, comprising stably transforming a monocot plant with the chimeric gene of claim 4, obtaining seeds from the transformed plants, germinating the seeds, and obtaining the heterologous protein from endosperm tissue of the seeds.

7. The chimeric gene of claim 5, wherein the transcriptional regulatory region has the sequence identified by SEQ ID NO:11.

8. The chimeric gene of claim 3, wherein the first DNA sequence encodes a mature, non-plant heterologous protein.

9. A monocot plant stably transformed with the chimeric gene of claim 3.

10. Seeds obtained from the monocot plant of claim 9.

11. The monocot plant of claim 9, wherein the first coding sequence encodes the sequence of a mature, non-plant heterologous protein, the transcriptional regulatory region hybridizes under conditions of high stringency with a rice β-glucanase gene promoter having a sequence selected from the group of sequences identified by SEQ ID NO:11, SEQ ID NO:13, SEQ ID NO:14, and seeds obtained from the plant produce the heterologous protein during seed germination.

12. A chimeric gene for use in producing a transgenic monocot plant comprising a DNA sequence having, operatively linked in sequence in a 5' to 3' direction, a transcriptional regulatory region from a rice β-glucanase isozyme gene and which hybridizes under conditions of high stringency with a rice β-glucanase gene promoter selected from the group of promoters identified by SEQ ID NO:9, SEQ ID NO:10, SEQ ID NO: 11, SEQ ID NO:12, SEQ ID NO: 13, SEQ ID NO:14, SEQ ID NO:15, and SEQ ID NO:16, a first DNA sequence heterologous to said regulatory region, and encoding a protein to be produced by said plant, and a second DNA sequence encoding a signal polypeptide, where said second DNA sequence is operably linked to said transcriptional regulatory region and to said first DNA sequence, and where said signal polypeptide is in translation-frame with said protein and is effective to facilitate secretion of said protein into the apoplast of a plant tissue in which said protein is expressed.

13. The chimeric gene of claim 12, for use in producing a heterologous protein in root tissue of the transformed plant, wherein the transcriptional regulatory region hybridizes under conditions of high stringency with a rice β-glucanase gene promoter having the sequence identified by SEQ ID NO:15.

14. The chimeric gene of claim 12, for use in producing a heterologous protein in callus tissue of the transformed plant, wherein the transcriptional regulatory region hybridizes under conditions of high stringency with a rice β-glucanase gene promoter having the sequence identified by SEQ ID NO:16.

15. The chimeric gene of claim 14, wherein the transcriptional regulatory region has the sequence identified by SEQ ID NO:16.

16. The chimeric gene of claim 12, for use in producing a heterologous protein in leaf tissue of the transformed plant, wherein the transcriptional regulatory region hybridizes under conditions of high stringency with a rice β-glucanase gene promoter having a sequence selected from the group of sequences identified by SEQ ID NO:13 and SEQ ID NO:14.

* * * * *